United States Patent [19]

Suzuki et al.

[11] Patent Number: 5,670,452

[45] Date of Patent: Sep. 23, 1997

[54] INDAZOLESULFONYLUREA DERIVATIVE, ITS USE AND INTERMEDIATE FOR ITS PRODUCTION

[75] Inventors: Chiharu Suzuki; Katsumi Masuda; Masatoshi Tamaru; Masahito Inamori; Nobuo Takefuji; Katsutada Yanagisawa, all of Shizuoka; Yasunori Ogawa, Kakegawa, all of Japan

[73] Assignees: Kumiai Chemical Industry Co., Ltd.; Ihara Chemical Industry Co., Ltd., both of Tokyo, Japan

[21] Appl. No.: 630,092

[22] Filed: Apr. 9, 1996

Related U.S. Application Data

[62] Division of Ser. No. 373,273, filed as PCT/JP94/01016, Jun. 24, 1994, Pat. No. 5,534,481.

[30] Foreign Application Priority Data

Jun. 25, 1993 [JP] Japan .................... 5-180809
Jun. 25, 1993 [JP] Japan .................... 5-180810
Dec. 10, 1993 [JP] Japan .................... 5-341772

[51] Int. Cl.$^6$ .................... C07D 40/12; A01N 43/66
[52] U.S. Cl. .................... 504/213; 544/198; 544/207; 544/209; 544/212
[58] Field of Search .................... 504/213; 544/148, 544/207, 209, 212

[56] References Cited

U.S. PATENT DOCUMENTS 4,465,505  8/1984  Wolf .................... 504/213
4,622,062  11/1986  Wexler .................. 544/320

*Primary Examiner*—John M. Ford
*Attorney, Agent, or Firm*—Oblon, Spivak, McClelland, Maier & Neustadt, P.C.

[57] ABSTRACT

The present invention provides an indazolesulfonylurea derivative represented by the general formula:

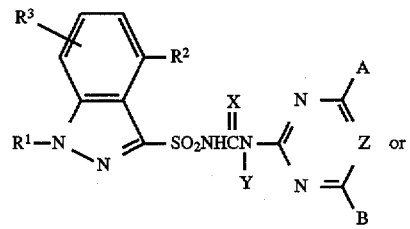

or

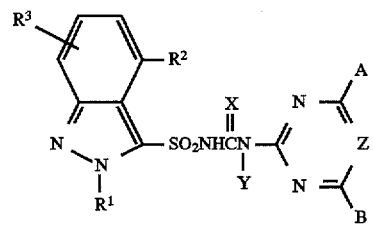

wherein $R^1$ is a hydrogen atom or an alkyl group, etc., $R^2$ and $R^3$ are the same or different and represent a hydrogen atom, a halogen atom, an alkyl group, the formula —COR$^4$ (wherein R$^4$ represents an alkoxy group, etc.), an alkoxy group, a haloalkoxy group or a cyano group, etc., X is an oxygen atom or a sulfur atom, Y is a hydrogen atom or an alkyl group, etc., A and B are the same or different and represent a halogen atom, an alkoxy group or an alkyl group, etc., and Z represents a nitrogen atom or a methine group, as well as a herbicide containing it as an active ingredient and an intermediate for its production.

The compound of the present invention exhibits excellent herbicidal effects over a wide range from the preemergence stage to the growing stage of various weeds which are problematic in agricultural fields. Further, it is capable of controlling weeds germinating in paddy fields.

4 Claims, No Drawings

INDAZOLESULFONYLUREA DERIVATIVE, ITS USE AND INTERMEDIATE FOR ITS PRODUCTION

This is a Division, of application Ser. No. 08/373,273, filed as PCT/JP94/01016, Jun. 24, 1994, now U.S. Pat. No. 5,534,481.

TECHNICAL FIELD

The present invention relates to a novel indazolesulfonylurea derivative (hereinafter referred to as a compound of the present invention), an intermediate for its production and a herbicide containing it as an active ingredient.

BACKGROUND ART

Heretofore, many sulfonylurea derivatives such as sulfometuron-methyl have been known as herbicides. Japanese Unexamined Patent Publication No. 95091/1992 discloses a herbicide containing an indazolesulfonylurea as an active ingredient. However, the compound of the present invention i.e. a sulfonylurea derivative having a sulfamoyl group substituted at the 3-position of an indazole ring, has not been known. Further, the intermediate for its production i.e. an indazolesulfonamide derivative, has also not been known.

It is known that sulfonylurea derivatives have herbicidal activities, but such compounds are not necessarily practically satisfactory, for example, in that their herbicidal effects are inadequate.

Under these circumstances, the present inventors have conducted various studies, and as a result, they have found that the compound of the present invention is an excellent herbicide having a high activity and has finally accomplished the present invention.

DISCLOSURE OF THE INVENTION

Namely, the present invention provides an indazolesulfonylurea derivative represented by the general formula:

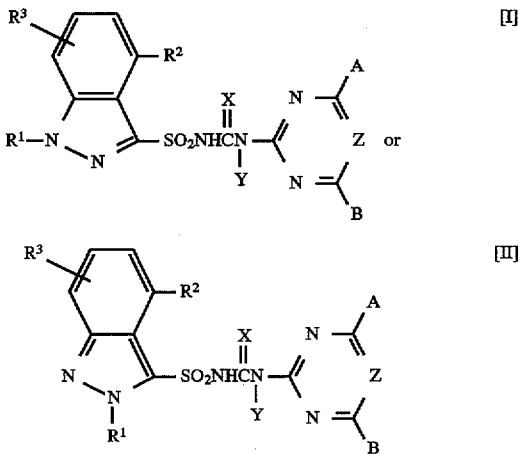

{wherein $R^1$ is a hydrogen atom, an alkyl group, a cycloalkyl group, a haloalkyl group, an alkoxyalkyl group, a benzyloxyalkyl group, a benzyl group, a phenyl group, a pyridyl group, a dialkylaminocarbonyl group, an alkoxycarbonyl group, an alkylsulfonyl group, a phenylsulfonyl group, a dialkylaminosulfonyl group, a haloalkylcarbonyl group, an alkylcarbonyl group, a benzoyl group or an alkenyl group, $R^2$ and $R^3$ are the same or different and represent a hydrogen atom, a halogen atom, an alkyl group, a cycloalkyl group, an alkenyl group, an alkoxycarbonylalkenyl group, an alkynyl group, a haloalkyl group, an alkoxyalkyl group, an alkoxycarbonylalkyl group, an alkylcarbonylalkyl group, a cycloalkylcarbonylalkyl group, a cyanoalkyl group, a dialkylaminocarbonylalkyl group, a dialkylaminoalkyl group, a dialkylaminosulfonylalkyl group, an azidoalkyl group, a benzyl group, a phenyl group, a nitro group, a cyano group, an azide group, an amino group, a monoalkylamino group, a dialkylamino group, a benzylamino group, an alkylcarbonylamino group which may be substituted by a halogen atom, a benzoylamino group, an alkoxycarbonylamino group, a phenoxycarbonylamino group, an alkylsulfonylamino group wherein the amino group may be substituted by an alkyl group, a phenylsulfonylamino group wherein the amino group may be substituted by an alkyl group, an alkylideneamino group, a benzylideneamino group, a tetrazolyl group which may be substituted, a group represented by the formula —$COR^4$ (wherein $R^4$ is a hydrogen atom, a hydroxyl group, an alkyl group, a cycloalkyl group, a haloalkyl group, an alkenyl group, an alkynyl group, a benzyl group, a phenyl group, an alkoxy group, a haloalkoxy group, an alkoxyalkoxy group, an alkenyloxy group, a haloalkenyloxy group, an alkynyloxy group, a benzyloxy group or a phenoxy group), a group represented by the formula —$C(O)NR^5R^6$ (wherein $R^5$ and $R^6$ are the same or different and represent a hydrogen atom, an alkyl group, an alkenyl group, an alkynyl group, a benzyl group, a phenyl group or an alkoxy group), a group represented by the formula —$SR^7$ (wherein $R^7$ is a hydrogen atom, an alkyl group or a haloalkyl group), a group represented by the formula —$SO_2NR^5R^6$ (wherein $R^5$ and $R^6$ have the same meanings as defined above), a group represented by the formula —$S(O)_nR^8$ (wherein n represents an integer of 1 or 2, and $R^8$ represents an alkyl group, an alkenyl group or a haloalkyl group), a group represented by the formula —$OR^9$ [wherein $R^9$ is a hydrogen atom, an alkyl group, a cycloalkylalkyl group, an alkenyl group, an alkynyl group, a benzyl group (said group may be substituted by a halogen atom, an alkyl group or an alkoxy group), a haloalkyl group, a haloalkenyl group, a phenyl group (said group may be substituted by a halogen atom, an alkyl group or an alkoxy group), an alkoxyalkyl group, an alkoxyalkoxyalkyl group, a haloalkoxyalkyl group, a benzyloxyalkyl group, a phenoxyalkyl group, an alkylthioalkyl group, a dialkylaminoalkyl group, an azidoalkyl group, an alkylcarbonyl group, a haloalkylcarbonyl group, a benzoyl group, a dialkylaminocarbonyl group, a cyanoalkyl group, an alkylideneamino group, a dialkylideneamino group, a benzylideneamino group or an alkoxycarbonylalkyl group], or the formula —$C(=NOR^{10})R^{11}$ (wherein $R^{10}$ represents a hydrogen atom, an alkyl group, an alkenyl group, an alkynyl group, a benzyl group, a haloalkyl group or a phenyl group, and $R^{11}$ represents a hydrogen atom, an alkyl group, a benzyl group, a haloalkyl group or a phenyl group), $R^2$ and $R^3$ may together form a ring with an alkyl group which may contain a hetero atom, A and B are the same or different and represent an alkyl group, a haloalkyl group, an alkoxy group, a monoalkylamino group, a dialkylamino group, a halogen atom or a haloalkoxy group, Z represents a methine group or a nitrogen atom, X represents an oxygen atom or a sulfur atom, and Y represents a hydrogen atom, an alkyl group or an alkoxyalkyl group, as well as its intermediate represented by an indazolesulfonamide derivative represented by the formula [I-a] or [II-a]:

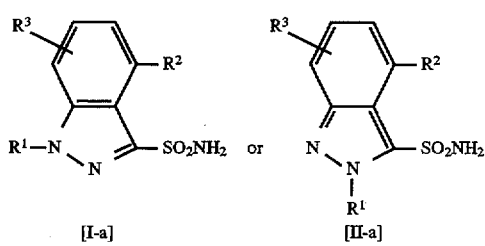

[I-a]       [II-a]

{wherein $R^1$ is a hydrogen atom, an alkyl group, a cycloalkyl group, a haloalkyl group, an alkoxyalkyl group, a benzyloxyalkyl group, a benzyl group, a phenyl group, a pyridyl group, a dialkylaminocarbonyl group, an alkoxycarbonyl group, an alkylsulfonyl group, a phenylsulfonyl group, a dialkylaminosulfonyl group, a haloalkylcarbonyl group, an alkylcarbonyl group, a benzoyl group or an alkenyl group, $R^2$ and $R^3$ are the same or different and represent a hydrogen atom, a halogen atom, an alkyl group, a cycloalkyl group, an alkenyl group, an alkoxycarbonylalkenyl group, an alkynyl group, a haloalkyl group, an alkoxyalkyl group, an alkoxycarbonylalkyl group, an alkylcarbonylalkyl group, a cycloalkylcarbonylalkyl group, a cyanoalkyl group, a dialkylaminocarbonylalkyl group, a dialkylaminoalkyl group, a dialkylaminosulfonylalkyl group, an azidoalkyl group, a benzyl group, a phenyl group, a nitro group, a cyano group, an azide group, an amino group, a monoalkylamino group, a dialkylamino group, a benzylamino group, an alkylcarbonylamino group which may be substituted by a halogen atom, a benzoylamino group, an alkoxycarbonylamino group, a phenoxycarbonylamino group, an alkylsulfonylamino group wherein the amino group may be substituted by an alkyl group, a phenylsulfonylamino group wherein the amino group may be substituted by an alkyl group, an alkylideneamino group, a benzylideneamino group, a tetrazolyl group which may be substituted, a group represented by the formula —$COR^4$ (wherein $R^4$ is a hydrogen atom, a hydroxyl group, an alkyl group, a cycloalkyl group, a haloalkyl group, an alkenyl group, an alkynyl group, a benzyl group, a phenyl group, an alkoxy group, a haloalkoxy group, an alkoxyalkoxy group, an alkenyloxy group, a haloalkenyloxy group, an alkynyloxy group, a benzyloxy group or a phenoxy group), a group represented by the formula —$C(O)NR^5R^6$ (wherein $R^5$ and $R^6$ are the same or different and represent a hydrogen atom, an alkyl group, an alkenyl group, an alkynyl group, a benzyl group, a phenyl group or an alkoxy group), a group represented by the formula —$SR^7$ (wherein $R^7$ is a hydrogen atom, an alkyl group or a haloalkyl group), a group represented by the formula —$SO_2NR^5R^6$ (wherein $R^5$ and $R^6$ have the same meanings as defined above), a group represented by the formula —$S(O)_nR^8$ (wherein n represents an integer of 1 or 2, and $R^8$ represents an alkyl group, an alkenyl group or a haloalkyl group), a group represented by the formula —$OR^9$ [wherein $R^9$ is a hydrogen atom, an alkyl group, a cycloalkylalkyl group, an alkenyl group, an alkynyl group, a benzyl group (said group may be substituted by a halogen atom, an alkyl group or an alkoxy group), a haloalkyl group, a haloalkenyl group, a phenyl group (said group may be substituted by a halogen atom, an alkyl group or an alkoxy group), an alkoxyalkyl group, an alkoxyalkoxyalkyl group, a haloalkoxyalkyl group, a benzyloxyalkyl group, a phenoxyalkyl group, an alkylthioalkyl group, a dialkylaminoalkyl group, an azidoalkyl group, an alkylcarbonyl group, a haloalkylcarbonyl group, a benzoyl group, a dialkylaminocarbonyl group, a cyanoalkyl group, an alkylideneamino group, a dialkylideneamino group, a benzylideneamino group or an alkoxycarbonylalkyl group], or the formula —$C(=NOR^{10})R^{11}$ (wherein $R^{10}$ represents a hydrogen atom, an alkyl group, an alkenyl group, an alkynyl group, a benzyl group, a haloalkyl group or a phenyl group, and $R^{11}$ represents a hydrogen atom, an alkyl group, a benzyl group, a haloalkyl group or a phenyl group), and $R^2$ and $R^3$ may form a ring with an alkyl group which may contain a hetero atom}, and a herbicide containing the indazolesulfonylurea as an active ingredient.

The compound of the present invention includes a tautomer, a geometrical isomer and an optical isomer thereof.

In the present invention, the alkyl group means a straight chain or branched chain alkyl group having from 1 to 30 carbon atoms and includes, for example, a methyl group, an ethyl group, a n-propyl group, an isopropyl group, a n-butyl group, an isobutyl group, a sec-butyl group, a t-butyl group, a n-pentyl group, an isoamyl group, a neopentyl group, a n-hexyl group, an isohexyl group, a 3,3-dimethylbutyl group, a n-heptyl group, a 5-methylhexyl group, a 4-methylhexyl group, a 3-methylhexyl group, a 4,4-dimethylpentyl group, a n-octyl group, a 6-methylheptyl group, a n-nonyl group, a 7-methyloctyl group, a n-decyl group, a 8-methylnonyl group, a n-undecyl group, a 9-methyldecyl group, a n-dodecyl group, a 10-methylundecyl group, a n-tridecyl group, a 11-methyldodecyl group, a n-tetradecyl group, a 12-methyltridecyl group, a n-pentadecyl group, a 13-methyltetradecyl group, a n-hexadecyl group, a n-heptadecyl group, a n-octadecyl group, a n-nonadecyl group, and a n-eicosyl group.

The alkoxy group and the alkylsulfonyl group mean an (alkyl)—O— group and and (alkyl)—$SO_2$— group, respectively, in which the alkyl moiety has the above-mentioned meaning.

The halogen atom includes fluorine, chlorine, bromine and iodine atoms.

The alkenyl group means a straight chain or branched chain alkenyl group having from 2 to 20 carbon atoms and includes, for example, a vinyl group, a propenyl group, an isopropenyl group, a butenyl group, a pentenyl group, a hexenyl group, a heptenyl group, an octenyl group, a 3-methyl-1-butenyl group, and a 4-methyl-1-pentenyl group.

The alkynyl group means a straight chain or branched chain alkynyl group having from 2 to 20 carbon atoms and includes, for example, an ethynyl group, a propynyl group, a butynyl group, a pentynyl group, a hexynyl group, a 3,3-dimethyl-1-butynyl group, a 4-methyl-1-pentynyl group, a 3-methyl-1-pentynyl group, a 5-methyl-1-hexynyl group, a 4-methyl-1-hexynyl group, a 3-methyl-1-hexynyl group, a heptynyl group, an octynyl group, a nonynyl group, a decynyl group, an undecynyl group, a dodecynyl group, a tridecynyl group, a tetradecynyl group, a pentadecynyl group, and a hexadecynyl group.

In the above formula [I] or [II], as a group of compounds showing preferred herbicidal effects, compounds may be mentioned wherein $R^1$ represents a hydrogen atom, a methyl group or an ethyl group, $R^2$ and $R^3$ are the same or different and represent a hydrogen atom, a halogen atom, an alkoxycarbonyl group, a dialkylaminocarbonyl group, an alkoxy group, a haloalkoxy group, an alkenyloxy group, a cyano group or a trifluoromethyl group, A and B are the same or different and represent a methoxy group, a methyl group or a haloalkoxy group, Z represents a methine group or a nitrogen atom, X represents an oxygen atom, and Y represents a hydrogen atom.

Now, typical specific examples of the compound of the present invention represented by the formula [I] or [II] will be exemplified in Tables 1 and 2. The compound numbers will be referred to in the subsequent description, and when $R^1$ represents a hydrogen atom, the compound may take tautomers represented by the formula [I] and [II].

The following symbols in the Tables in the present specification represent the following groups, respectively.

| | |
|---|---|
| Bn: | Benzyl group |
| Pen: | n-Pentyl group |
| Me: | Methyl group |
| Et: | Ethyl group |
| Pr: | n-Propyl group |
| Bu: | n-Butyl group |
| Ph: | Phenyl group |

TABLE 1

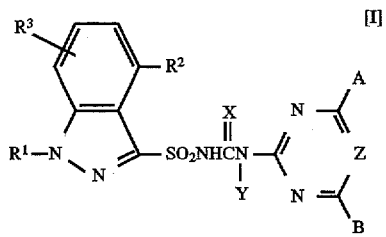

[I]

| Comp. NO. | $R^1$ | $R^2$ | $R^3$ | X | Y | A | B | Z | Mp. (°C.) |
|---|---|---|---|---|---|---|---|---|---|
| I-1 | Me | Ph | H | O | H | OMe | OMe | CH | |
| I-2 | Me | Bn | H | O | H | OMe | OMe | CH | |
| I-3 | Me | SH | H | O | H | OMe | OMe | CH | |
| I-4 | Me | SMe | H | O | H | OMe | OMe | CH | |
| I-5 | Me | SEt | H | O | H | OMe | OMe | CH | 189–190 |
| I-6 | Me | SPr | H | O | H | OMe | OMe | CH | 162–164 |
| I-7 | Me | SO$_2$Me | H | O | H | OMe | OMe | CH | |
| I-8 | Me | SO$_2$Et | H | O | H | OMe | OMe | CH | 157–160 |
| I-9 | Me | SOMe | H | O | H | OMe | OMe | CH | |
| I-10 | Me | SO$_2$NHMe | H | O | H | OMe | OMe | CH | |
| I-11 | Me | SO$_2$NHOMe | H | O | H | OMe | OMe | CH | |
| I-12 | Me | SO$_2$NMe$_2$ | H | O | H | OMe | OMe | CH | 214–216 |
| I-13 | Me | SO$_2$NHBn | H | O | H | OMe | OMe | CH | |
| I-14 | Me | SO$_2$NHPh | H | O | H | OMe | OMe | CH | |
| I-15 | Me | SO$_2$NHCH$_2$CH=CH$_2$ | H | O | H | OMe | OMe | CH | |
| I-16 | Me | SO$_2$NHCH$_2$C≡CH | H | O | H | OMe | OMe | CH | |
| I-17 | H | Cl | H | O | H | OMe | OMe | CH | 191–193 |
| I-18 | Me | Cl | H | O | H | Me | Me | CH | 195–198 |
| I-19 | Me | Cl | 5-Cl | O | H | OMe | OMe | CH | 210–213 |
| I-20 | Et | Cl | H | O | H | OMe | OMe | CH | 187–189 |
| I-21 | Ph | Cl | H | O | H | OMe | OMe | CH | |
| I-22 | Bn | Cl | H | O | H | OMe | OMe | CH | |
| I-23 | Me | H | H | O | H | OMe | OMe | CH | 181–183 |
| I-24 | Me | H | H | O | H | Me | Me | CH | |
| I-25 | Me | H | H | O | H | OMe | Me | N | 172–174 |
| I-26 | Me | F | H | O | H | OMe | OMe | CH | 205–209 |
| I-27 | Me | Br | H | O | H | OMe | OMe | CH | 276–279 |
| I-28 | Me | Me | H | O | H | OMe | OMe | CH | 178–180 |
| I-29 | Me | CN | H | O | H | OMe | OMe | CH | 267–269 |
| I-30 | Me | CF | H | O | H | OMe | OMe | CH | |
| I-31 | Me | Cl | H | O | H | OMe | Me | CH | 243–245 |
| I-32 | Me | Cl | H | O | H | OMe | Me | N | 266–267 |
| I-33 | Me | F | H | O | H | Me | Me | CH | 195–197 |
| I-34 | Me | F | H | O | H | OMe | Me | N | 197–200 |
| I-35 | Me | F | H | O | H | OMe | Me | CH | 180–185 |
| I-36 | Me | H | 5-Cl | O | H | OMe | OMe | CH | |
| I-37 | Me | H | 5-Cl | O | H | Me | Me | CH | |
| I-38 | Me | H | 5-Cl | O | H | OMe | Me | N | |
| I-39 | Me | H | 6-Cl | O | H | OMe | OMe | CH | |
| I-40 | Me | H | 6-Cl | O | H | Me | Me | CH | |
| I-41 | Me | H | 6-Cl | O | H | OMe | Me | N | |
| I-42 | Me | H | 7-Cl | O | H | OMe | OMe | CH | |
| I-43 | Me | H | 7-Cl | O | H | OMe | Me | N | |
| I-44 | Me | Cl | H | S | H | OMe | OMe | CH | |
| I-45 | Me | Cl | H | O | Me | OMe | OMe | CH | |
| 1-46 | Me | COH | H | O | H | OMe | OMe | CH | |
| I-47 | Me | COMe | H | O | H | OMe | OMe | CH | |
| I-48 | Me | COEt | H | O | H | OMe | OMe | CH | |
| I-49 | Me | COPh | H | O | H | OMe | OMe | CH | |
| I-50 | Me | COCH$_2$CH=CH$_2$ | H | O | H | OMe | OMe | CH | |
| I-51 | Me | COCH$_2$C≡CH | H | O | H | OMe | OMe | CH | |
| I-52 | Me | COBn | H | O | H | OMe | OMe | CH | |

TABLE 1-continued

[Structure I: R³ and R² substituted benzene fused to pyrazole with R¹-N, connected via SO₂NHCN(X)(Y) to pyrimidine ring with A, B, Z substituents]

| Comp. NO. | R¹ | R² | R³ | X | Y | A | B | Z | Mp. (°C.) |
|---|---|---|---|---|---|---|---|---|---|
| I-53 | Me | NO₂ | H | O | H | OMe | OMe | CH | 219–220 |
| I-54 | Me | NH₂ | H | O | H | OMe | OMe | CH | |
| I-55 | Me | NHMe | H | O | H | OMe | OMe | CH | |
| I-56 | Me | NMe₂ | H | O | H | OMe | OMe | CH | |
| I-57 | Me | NHCOMe | H | O | H | OMe | OMe | CH | |
| I-58 | Me | NHCOPh | H | O | H | OMe | OMe | CH | |
| I-59 | Me | NHCOCH₂Cl | H | O | H | OMe | OMe | CH | |
| I-60 | Me | NHSO₂CH₃ | H | O | H | OMe | OMe | CH | |
| I-61 | Me | NHSO₂Ph | H | O | H | OMe | OMe | CH | |
| I-62 | Me | CO₂H | H | O | H | OMe | OMe | CH | |
| I-63 | Me | CO₂Me | H | O | H | OMe | OMe | CH | 187–190 |
| I-64 | Me | CO₂Et | H | O | H | OMe | OMe | CH | 192–193 |
| I-65 | Me | CO₂Pr | H | O | H | OMe | OMe | CH | 195–197 |
| I-66 | Me | CO₂Pr-i | H | O | H | OMe | OMe | CH | 168–169 |
| I-67 | Me | CO₂Bu | H | O | H | OMe | OMe | CH | 169–172 |
| I-68 | Me | CO₂Pen | H | O | H | OMe | OMe | CH | |
| I-69 | Me | CO₂Bn | H | O | H | OMe | OMe | CH | |
| I-70 | Me | CO₂Ph | H | O | H | OMe | OMe | CH | |
| I-71 | Me | CO₂CH₂CH₂F | H | O | H | OMe | OMe | CH | |
| I-72 | Me | CO₂CH₂CH=CH₂ | H | O | H | OMe | OMe | CH | |
| I-73 | Me | CO₂CH₂C≡CH | H | O | H | OMe | OMe | CH | |
| I-74 | Me | CO₂Me | H | O | H | OCHF₂ | OCHF₂ | CH | |
| I-75 | Me | CO₂Et | H | O | H | OCHF₂ | OCHF₂ | CH | |
| I-76 | Me | CO₂Me | H | O | H | OMe | Cl | CH | |
| I-77 | Me | CO₂Me | H | O | H | OMe | Me | CH | |
| I-78 | Me | CO₂Me | H | O | H | OMe | Me | N | |
| I-79 | Me | CO₂Et | H | O | H. | OMe | Me | N | 193–196 |
| I-80 | Me | CO₂Me | H | O | H | OMe | OCHF₂ | CH | |
| I-81 | Me | CO₂Me | 5-F | O | H | OMe | OMe | CH | |
| I-82 | Et | CO₂Me | H | O | H | OMe | OMe | CH | 182–183 |
| I-83 | Bu | CO₂Me | H | O | H | OMe | OMe | CH | |
| I-84 | Bn | CO₂Me | H | O | H | OMe | OMe | CH | |
| I-85 | Ph | CO₂Me | H | O | H | OMe | OMe | CH | |
| I-86 | H | CO₂Et | H | O | H | OMe | OMe | CH | |
| I-87 | Me | CO₂Me | H | S | H | OMe | OMe | CH | |
| I-88 | Me | CO₂Et | H | S | H | OMe | OMe | CH | |
| I-89 | Me | CO₂Me | H | O | Me | OMe | OMe | CH | |
| I-90 | Me | OH | H | O | H | OMe | OMe | CH | |
| I-91 | Me | ONMe | H | O | H | OMe | OMe | CH | 265–267 |
| I-92 | Me | OEt | H | O | H | OMe | OMe | CH | 162–164 |
| I-93 | Me | OPr | H | O | H | OMe | OMe | CH | 134–136 |
| I-94 | Me | OPr-i | H | O | H | OMe | OMe | CH | 168–171 |
| I-95 | Me | OBu | H | O | H | OMe | OMe | CH | 198–200 |
| I-96 | Me | OBn | H | O | H | OMe | OMe | CH | |
| I-97 | Me | OBn(4-Cl) | H | O | H | OMe | OMe | CH | |
| I-98 | Me | OBn(3-OMe) | H | O | H | OMe | OMe | CH | |
| I-99 | Me | OBn(2-Me) | H | O | H | OMe | OMe | CH | |
| I-100 | Me | OPh | H | O | H | OMe | OMe | CH | |
| I-101 | Me | OPh(4-Cl) | H | O | H | OMe | OMe | CH | |
| 1-102 | Me | OPh(3-OMe) | H | O | H | OMe | OMe | CH | |
| I-103 | Me | OPh(2-Me) | H | O | H | OMe | OMe | CH | |
| I-104 | Me | OCH₂CH=CH₂ | H | O | H | OMe | OMe | CH | |
| I-105 | Me | OCH₂C≡CH | H | O | H | OMe | OMe | CH | |
| I-106 | Me | OCH₂CF₃ | H | O | H | OMe | OMe | CH | |
| I-107 | Me | OCH₂CH₂OMe | H | O | H | OMe | OMe | CH | |
| I-108 | Me | OCH₂CH₂OPh | H | O | H | OMe | OMe | CH | |
| I-109 | Me | OCOMe | H | O | H | OMe | OMe | CH | |
| I-110 | Me | OMe | H | O | H | OMe | Me | CH | |
| I-111 | Me | OMe | H | O | H | OMe | Me | N | 269–270 |
| I-112 | Me | OMe | H | O | H | Me | Me | CH | 267–268 |
| I-113 | Me | OEt | H | O | H | OMe | Cl | CH | 161–165 |
| I-114 | Me | OEt | H | O | H | OMe | Me | CH | 169–170 |
| I-115 | Me | OEt | H | O | H | Me | Me | CH | |
| I-116 | Me | CONH₂ | H | O | H | OMe | OMe | CH | |

TABLE 1-continued

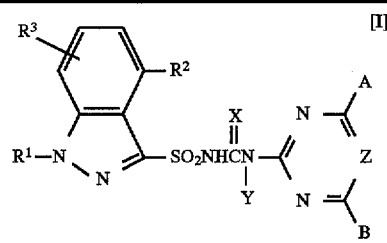

| Comp. NO. | R¹ | R² | R³ | X | Y | A | B | Z | Mp. (°C.) |
|---|---|---|---|---|---|---|---|---|---|
| I-117 | Me | CONHMe | H | O | H | OMe | OMe | CH | |
| I-118 | Me | CONHEt | H | O | H | OMe | OMe | CH | |
| I-119 | Me | CONHPr | H | O | H | OMe | OMe | CH | |
| I-120 | Me | CONMe₂ | H | O | H | OMe | OMe | CH | 205–207 |
| I-121 | Me | COMEt | H | O | H | OMe | OMe | CH | |
| I-122 | Me | CONHBn | H | O | H | OMe | OMe | CH | |
| I-123 | Me | CONHPh | H | O | H | OMe | OMe | CH | |
| I-124 | Me | CONHCH₂CH=CH₂ | H | O | H | OMe | OMe | CH | |
| I-125 | Me | CONHCH₂C≡CH | H | O | H | OMe | OMe | CH | |
| I-126 | Me | CONHOMe | H | O | H | OMe | OMe | CH | |
| I-127 | Me | H | 5-F | O | H | OMe | OMe | CH | |
| I-128 | Me | H | 5-F | O | H | Me | Me | CH | |
| I-129 | Me | H | 5-F | O | H | OMe | Me | CH | |
| I-130 | Me | H | 5-F | O | H | OMe | Me | N | |
| I-131 | H | COOMe | H | O | H | OMe | OMe | CH | 179–180 |
| I-132 | H | COOMe | H | O | H | OMe | Cl | CH | 193–194 |
| I-133 | H | Cl | H | O | H | OMe | Cl | CH | 178–181 |
| I-134 | Me | Cl | H | O | H | OMe | OMe | CH | 265–267 |
| I-135 | Me | SO₂₂NH₂ | H | O | H | OMe | OMe | CH | |
| I-136 | H | Br | H | O | H | OMe | OMe | CH | 190–193 |
| I-137 | Me | H | 5-Me | O | H | OMe | OMe | CH | |
| I-138 | Me | H | 5-OEt | O | H | OMe | OMe | CH | |
| I-139 | Me | H | 5-OPr | O | H | OMe | OMe | CH | |
| I-140 | Me | OCH(CF₃)Me | H | O | H | OMe | OMe | CH | |
| I-141 | Me | OCH₂CH₂Cl | H | O | H | OMe | OMe | CH | |
| I-142 | Me | OCH₂CH₂F | H | O | H | OMe | OMe | CH | |
| I-143 | Me | OCH₂CH₂OEt | H | O | H | OMe | OMe | CH | |
| I-144 | Me | OCH₂CH₂OPr-i | H | O | H | OMe | OMe | CH | |
| I-145 | Me | OCH₂CH₂OBu | H | O | H | OMe | OMe | CH | |
| I-146 | Me | OCH₂CH₂OBu-t | H | O | H | OMe | OMe | CH | |
| I-147 | Me | OCH₂COOEt | H | O | H | OMe | OMe | CH | |
| I-148 | Me | OCH₂CH₂NMe₂ | H | O | H | OMe | OMe | CH | |
| I-149 | Me | SBu | H | O | H | OMe | OMe | CH | 165–168 |
| I-150 | Me | SPr-i | H | O | H | OMe | OMe | CH | 178–180 |
| I-151 | Me | SO₂Pr | H | O | H | OMe | OMe | CH | 163–167 |
| I-152 | Me | SO₂Bu | H | O | H | OMe | OMe | CH | 187–189 |
| I-153 | Me | SO₂Pr-i | H | O | H | OMe | OMe | CH | 279–281 |
| I-154 | Me | NHBn | H | O | H | OMe | OMe | CH | |
| I-155 | Me | NEt₂ | H | O | H | OMe | OMe | CH | |
| I-156 | Me | OMe | 5-Cl | O | H | OMe | OMe | CH | |
| I-157 | Me | Br | H | O | H | OMe | Me | CH | 276–279 |
| I-158 | Et | Cl | H | O | H | OMe | Me | CH | 182–184 |
| I-159 | Ph | Cl | H | O | H | OMe | Me | CH | |
| I-160 | Me | OPr | H | O | H | OMe | Me | CH | 178–180 |
| I-161 | Me | OBu | H | O | H | OMe | Me | CH | 174–176 |
| I-162 | Me | OPr-i | H | O | H | OMe | Me | CH | 184–186 |
| I-163 | Me | H | 5-OMe | O | H | OMe | Me | CH | |
| I-164 | Me | H | 5-OEt | O | H | OMe | Me | CH | |
| I-165 | Me | H | 5-OPr | O | H | OMe | Me | CH | |
| I-166 | Me | OCH₂CF₃ | H | O | H | OMe | Me | CH | |
| I-167 | Me | OCH(CF₃)Me | H | O | H | OMe | Me | CH | |
| I-168 | Me | OCH₂CH₂OMe | H | O | H | OMe | Me | CH | |
| I-169 | Me | OCH₂CH₂OEt | H | O | H | OMe | Me | CH | |
| I-170 | Me | OCH₂CH₂OPr-i | H | O | H | OMe | Me | CH | |
| I-171 | Me | OCH₂CH₂OBu | H | O | H | OMe | Me | CH | |
| I-172 | Me | OCH₂CH₂OBu-t | H | O | H | OMe | Me | CH | |
| I-173 | Me | OCH₂CH₂NMe₂ | H | O | H | OMe | Me | CH | |
| I-174 | Me | SPr | H | O | H | OMe | Me | CH | 155–156 |
| I-175 | Me | CO₂Pr | H | O | H | OMe | Me | CH | 185–186 |
| I-176 | Me | CO₂Pr-i | H | O | H | OMe | He | CH | 158–160 |
| I-177 | Me | CO₂Bu | H | O | H | OMe | Me | CH | 174–175 |
| I-178 | Me | NO₂ | H | O | H | OMe | Me | CH | 212–214 |
| I-179 | Me | CN | H | O | H | OMe | Me | CH | 180–181 |
| I-180 | Me | Br | H | O | H | OMe | Me | N | 166–169 |
| I-181 | Et | Cl | H | O | H | OMe | Me | N | 141–142 |

TABLE 1-continued

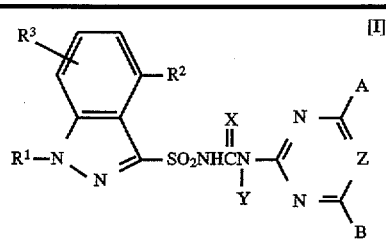

| Comp. NO. | R¹ | R² | R³ | X | Y | A | B | Z | Mp. (°C.) |
|---|---|---|---|---|---|---|---|---|---|
| I-182 | Me | OPr | H | O | H | OMe | Me | N | 210–213 |
| I-183 | Me | OBu | H | O | H | OMe | Me | N | 184–186 |
| I-184 | Me | OPr-i | H | O | H | OMe | Me | N | 157–159 |
| I-185 | Me | H | 5-OMe | O | H | OMe | Me | N | |
| I-186 | Me | H | 5-OEt | O | H | OMe | Me | N | |
| I-187 | Me | H | 5-OPr | O | H | OMe | Me | N | |
| I-188 | Me | OCH₂CF₃ | H | O | H | OMe | Me | N | |
| I-189 | Me | OCH₂CH₂OEt | H | O | H | OMe | Me | N | |
| I-190 | Me | OCH₂CH₂OPr-i | H | O | H | OMe | Me | N | |
| I-191 | Me | OCH₂CH₂OBu | H | O | H | OMe | Me | N | |
| I-192 | Me | OCH₂CH₂OBu-t | H | O | H | OMe | Me | N | |
| I-193 | Me | OCH₂CH₂NMe₂ | H | O | H | OMe | Me | N | |
| I-194 | Me | SEt | H | O | H | OMe | Me | N | 223–224 |
| I-195 | Me | SPr | H | O | H | OMe | Me | N | |
| I-196 | Me | NMe₂ | H | O | H | OMe | Me | N | |
| I-197 | Me | CO₂Pr-i | H | O | H | OMe | Me | N | |
| I-198 | Me | CO₂Bu | H | O | H | OMe | Me | N | 177–178 |
| I-199 | Me | CN | H | O | H | OMe | Me | N | 255–258 |
| I-200 | Me | OMe | 5-Cl | O | H | OMe | Me | N | |
| I-201 | Me | Cl | H | O | H | Cl | OMe | CH | |
| I-202 | Et | Cl | H | O | H | Cl | OMe | CH | |
| I-203 | Ph | Cl | H | O | H | Cl | OMe | CH | |
| I-204 | Me | OMe | H | O | H | Cl | OMe | CH | 268–269 |
| I-205 | Me | OPr | H | O | H | Cl | OMe | CH | 168–169 |
| I-206 | Me | OBu | H | O | H | Cl | OMe | CH | 171–173 |
| I-207 | Me | H | 5-OMe | O | H | Cl | OMe | CH | |
| I-208 | Me | OCH₂CF₃ | H | O | H | Cl | OMe | CH | |
| I-209 | Me | SPr | H | O | H | Cl | OMe | CH | 143–145 |
| I-210 | Me | SBu | H | O | H | Cl | OMe | CH | |
| I-211 | Me | SPr-i | H | O | H | Cl | OMe | CH | 228–230 |
| I-212 | Me | SO₂Pr-i | H | O | H | Cl | OMe | CH | 143–145 |
| I-213 | Me | NHBn | H | O | H | Cl | OMe | CH | |
| I-214 | Me | NMe₂ | H | O | H | Cl | OMe | CH | |
| I-215 | Et | Cl | H | O | H | Me | Me | CH | |
| I-216 | Me | OPr | H | O | H | Me | Me | CH | 149–150 |
| I-217 | Me | OBu | H | O | H | Me | Me | CH | 146–149 |
| I-218 | Me | OPr-i | H | O | H | Me | Me | CH | 174–176 |
| I-219 | Me | NMe₂ | H | O | H | Me | Me | CH | |
| I-220 | Me | OMe | H | O | H | OMe | OMe | N | |
| I-221 | Me | H | 5-OEt | O | H | OMe | OMe | N | |
| I-222 | Me | H | 5-OPr | O | H | OMe | OMe | N | |
| I-223 | Me | OCH₂CH₂OBu | H | O | H | OMe | OMe | N | |
| I-224 | Me | OCH₂CH₂OBu-t | H | O | H | OMe | OMe | N | |
| I-225 | Me | NHMe | H | O | H | OMe | Me | CH | |
| I-226 | Me | NHMe | H | O | H | OMe | Me | N | |
| I-227 | Me | OMe | H | O | H | OMe | Me | CH | |
| I-228 | Me | OMe | 5-OMe | O | H | OMe | Me | CH | |
| I-229 | Me | OCHF₂ | H | O | H | OMe | OMe | CH | 198–200 |
| I-230 | Me | OCHF₂ | H | O | H | Me | OMe | CH | 177–179 |
| I-231 | Me | OCHF₂ | H | O | H | Me | OMe | N | 165–167 |
| I-232 | Me | OCH₂CHF₂ | H | O | H | OMe | OMe | CH | |
| I-233 | Me | OCH₂CHF₂ | H | O | H | Me | OMe | CH | |
| I-234 | Me | OCH₂CHF₂ | H | O | H | Me | OMe | N | |
| I-235 | Me | OCH₂CH₂CF₃ | H | O | H | OMe | OMe | CH | |
| I-236 | Me | OCH₂CH₂CF₃ | H | O | H | Me | OMe | CH | |
| I-237 | Me | OCH₂CH₂CF₃ | H | O | H | Me | OMe | N | |
| I-238 | Me | OCH(CF₂CF₃)Me | H | O | H | OMe | OMe | CH | |
| I-239 | Me | OCH(CF₂CF₃)Me | H | O | H | Me | OMe | CH | |
| I-240 | Me | OCH(CF₂CF₃)Me | H | O | H | Me | OMe | N | |
| I-241 | Me | OCH₂CF₂CHF₂ | H | O | H | OMe | OMe | CH | |
| I-242 | Me | OCH₂CF₂CHF₂ | H | O | H | Me | OMe | CH | |
| I-243 | Me | OCH₂CF₂CHF₂ | H | O | H | Me | OMe | N | |
| I-244 | Me | OCH₂CF₂CF₃ | H | O | H | OMe | OMe | CH | |
| I-245 | Me | OCH₂CF₂CF₃ | H | O | H | Me | OMe | CH | |
| I-246 | Me | OCH₂CF₂CF₃ | H | O | H | Me | OMe | N | |
| I-247 | Me | OCH₂CHCl₂ | H | O | H | OMe | OMe | CH | |

TABLE 1-continued

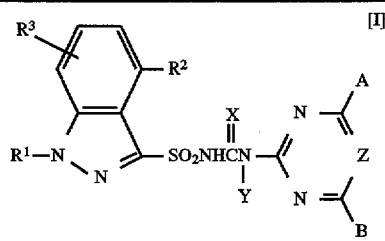

| Comp. NO. | R¹ | R² | R³ | X | Y | A | B | Z | Mp. (°C.) |
|---|---|---|---|---|---|---|---|---|---|
| I-248 | Me | OCH$_2$CHCl$_2$ | H | O | H | Me | OMe | CH | |
| I-249 | Me | OCH$_2$CHCl$_2$ | H | O | H | Me | OMe | N | |
| I-250 | Me | OCF$_2$CH$_2$Cl | H | O | H | OMe | OMe | CH | |
| I-251 | Me | OCF$_2$CH$_2$Cl | H | O | H | Me | OMe | CH | |
| I-252 | Me | OCF$_2$CH$_2$Cl | H | O | H | Me | OMe | N | |
| I-253 | Me | OCF$_2$CHFCl | H | O | H | OMe | OMe | CH | |
| I-254 | Me | OCF$_2$CHFCl | H | O | H | Me | OMe | CH | |
| I-255 | Me | OCF$_2$CHFCl | H | O | H | Me | OMe | N | |
| I-256 | Me | OCF$_3$ | H | O | H | OMe | OMe | CH | |
| I-257 | Me | OCF$_3$ | H | O | H | Me | OMe | CH | |
| I-258 | Me | OCF$_3$ | H | O | H | Me | OMe | N | |
| I-259 | Me | OCH$_2$CH=CH—Cl | H | O | H | OMe | OMe | CH | |
| I-260 | Me | OCH$_2$CH=CH—Cl | H | O | H | Me | OMe | CH | |
| I-261 | Me | OCH$_2$CH=CH—Cl | H | O | H | Me | OMe | N | |
| I-262 | Me | OCH$_2$CH=CCl$_2$ | H | O | H | OMe | OMe | CH | |
| I-263 | Me | OCH$_2$CH=CCl$_2$ | H | O | H | Me | OMe | CH | |
| I-264 | Me | OCH$_2$CH=CCl$_2$ | H | O | H | Me | OMe | N | |
| I-265 | Me | OCH$_2$C(Cl)=CH$_2$ | H | O | H | OMe | OMe | CH | |
| I-266 | Me | OCH$_2$C(Cl)=CH$_2$ | H | O | H | Me | OMe | CH | |
| I-267 | Me | OCH$_2$C(Cl)=CH$_2$ | H | O | H | Me | OMe | N | |
| I-268 | Me | OCH$_2$C(Me)=CH$_2$ | H | O | H | OMe | OMe | CH | |
| I-269 | Me | OCH$_2$C(Me)=CH$_2$ | H | O | H | Me | OMe | CH | |
| I-270 | Me | OCH$_2$C(Me)=CH$_2$ | H | O | H | Me | OMe | N | |
| I-271 | Me | OCH$_2$CH=CHMe | H | O | H | OMe | OMe | CH | |
| I-272 | Me | OCH$_2$CH=CHMe | H | O | H | Me | OMe | CH | |
| I-273 | Me | OCH$_2$CH=CHMe | H | O | H | Me | OMe | N | |
| I-274 | Me | OCH$_2$CH$_2$N$_3$ | H | O | H | OMe | OMe | CH | |
| I-275 | Me | OCH$_2$CH$_2$N$_3$ | H | O | H | Me | OMe | CH | |
| I-276 | Me | OCH$_2$CH$_2$N$_3$ | H | O | H | Me | OMe | N | |
| I-277 | Me | OCH$_2$OMe | H | O | H | OMe | OMe | CH | |
| I-278 | Me | OCH$_2$OMe | H | O | H | Me | OMe | CH | |
| I-279 | Me | OCH$_2$OMe | H | O | H | Me | OMe | N | |
| I-280 | Me | OCH$_2$OEt | H | O | H | OMe | OMe | CH | |
| I-281 | Me | OCH$_2$OEt | H | O | H | Me | OMe | CH | |
| I-282 | Me | OCH$_2$OEt | H | O | H | Me | OMe | N | |
| I-283 | Me | OCH$_2$OBn | H | O | H | OMe | OMe | CH | |
| I-284 | Me | OCH$_2$OBn | H | O | H | Me | OMe | CH | |
| I-285 | Me | OCH$_2$OBn | H | O | H | Me | OMe | N | |
| I-286 | Me | OCH$_2$OCH$_2$CF$_3$ | H | O | H | OMe | OMe | CH | |
| I-287 | Me | OCH$_2$OCH$_2$CF$_3$ | H | O | H | Me | OMe | CH | |
| I-288 | Me | OCH$_2$OCH$_2$CF$_3$ | H | O | H | Me | OMe | N | |
| I-289 | Me | OCH$_2$OBu-t | H | O | H | OMe | OMe | CH | |
| I-290 | Me | OCH$_2$OBu-t | H | O | H | Me | OMe | CH | |
| I-291 | Me | OCH$_2$OBu-t | H | O | H | Me | OMe | N | |
| I-292 | Me | OCH$_2$OCH$_2$CH$_2$OMe | H | O | H | OMe | OMe | CH | |
| I-293 | Me | OCH$_2$OCH$_2$CH$_2$OMe | H | O | H | Me | OMe | CH | |
| I-294 | Me | OCH$_2$OCH$_2$CH$_2$OMe | H | O | H | Me | OMe | N | |
| I-295 | Me | OCH$_2$CN | H | O | H | OMe | OMe | CH | |
| I-296 | Me | OCH$_2$CN | H | O | H | Me | OMe | CH | |
| I-297 | Me | OCH$_2$CN | H | O | H | Me | OMe | N | |
| I-298 | Me | OCH$_2$COOMe | H | O | H | OMe | OMe | CH | |
| I-299 | Me | OCH$_2$COOMe | H | O | H | Me | OMe | CH | |
| I-300 | Me | OCH$_2$COOMe | H | O | H | Me | OMe | N | |
| I-301 | Me | OCH$_2$COOPr | H | O | H | OMe | OMe | CH | |
| I-302 | Me | OCH$_2$COOPr | H | O | H | Me | OMe | CH | |
| I-303 | Me | OCH$_2$COOPr | H | O | H | Me | OMe | N | |
| I-304 | Me | OCH$_2$COOPr-i | H | O | H | OMe | OMe | CH | |
| I-305 | Me | OCH$_2$COOPr-i | H | O | H | Me | OMe | CH | |
| I-306 | Me | OCH$_2$COOPr-i | H | O | H | Me | OMe | N | |
| I-307 | Me | OCH$_2$SMe | H | O | H | OMe | OMe | CH | |
| I-308 | Me | OCH$_2$SMe | H | O | H | Me | OMe | CH | |
| I-309 | Me | OCH$_2$SMe | H | O | H | Me | OMe | N | |
| I-310 | Me | OCH$_2$CH$_2$SMe | H | O | H | OMe | OMe | CH | |
| I-311 | Me | OCH$_2$CH$_2$SMe | H | O | H | Me | OMe | CH | |
| I-312 | Me | OCH$_2$CH$_2$SMe | H | O | H | Me | OMe | N | |
| I-313 | Me | SCF$_3$ | H | O | H | OMe | OMe | CH | |

TABLE 1-continued

| Comp. NO. | R¹ | R² | R³ | X | Y | A | B | Z | Mp. (°C.) |
|---|---|---|---|---|---|---|---|---|---|
| I-314 | Me | SCF₃ | H | O | H | Me | OMe | CH | |
| I-315 | Me | SCF₃ | H | O | H | Me | OMe | N | |
| I-316 | Me | SCH₂CH₂Cl | H | O | H | OMe | OMe | CH | |
| I-317 | Me | SCH₂CH₂Cl | H | O | H | Me | OMe | CH | |
| I-318 | Me | SCH₂CH₂Cl | H | O | H | Me | OMe | N | |
| I-319 | Me | SCH₂CH₂F | H | O | H | OMe | OMe | CH | |
| I-320 | Me | SCH₂CH₂F | H | O | H | Me | OMe | CH | |
| I-321 | Me | SCH₂CH₂F | H | O | H | Me | OMe | N | |
| I-322 | Me | SOEt | H | O | H | OMe | OMe | CH | 185–187 |
| I-323 | Me | SOEt | H | O | H | Me | OMe | CH | |
| I-324 | Me | SOEt | H | O | H | Me | OMe | N | 136–137 (decomposed) |
| I-325 | Me | SO₂NHOEt | H | O | H | OMe | OMe | CH | |
| I-326 | Me | SO₂NHOEt | H | O | H | Me | OMe | CH | |
| I-327 | Me | SO₂NHOEt | H | O | H | Me | OMe | N | |
| I-328 | Me | SO₂CH₂CH=CH₂ | H | O | H | OMe | OMe | CH | |
| I-329 | Me | SO₂CH₂CH=CH₂ | H | O | H | Me | OMe | CH | |
| I-330 | Me | SO₂CH₂CH=CH₂ | H | O | H | Me | OMe | N | |
| I-331 | Me | SO₂NEt₂ | H | O | H | OMe | OMe | CH | |
| I-332 | Me | SO₂NEt₂ | H | O | H | Me | OMe | CH | |
| I-333 | Me | SO₂NEt₂ | H | O | H | Me | OMe | N | |
| I-334 | Me | Et | H | O | H | OMe | OMe | CH | 174–176 |
| I-335 | Me | Et | H | O | H | Me | OMe | CH | |
| I-336 | Me | Et | H | O | H | Me | OMe | N | |
| I-337 | Me | Pr | H | O | H | OMe | OMe | CH | 168–171 |
| I-338 | Me | Pr | H | O | H | Me | OMe | CH | |
| I-339 | Me | Pr | H | O | H | Me | OMe | N | |
| I-340 | Me | Pr-i | H | O | H | OMe | OMe | CH | |
| I-341 | Me | Pr-i | H | O | H | Me | OMe | CH | |
| I-342 | Me | Pr-i | H | O | H | Me | OMe | N | |
| I-343 | Me | Bu | H | O | H | OMe | OMe | CH | |
| I-344 | Me | Bu | H | O | H | Me | OMe | CH | |
| I-345 | Me | Bu | H | O | H | Me | OMe | N | |
| I-346 | He | Bu-t | H | O | H | OMe | OMe | CH | |
| I-347 | Me | Bu-t | H | O | H | Me | OMe | CH | |
| I-348 | Me | Bu-t | H | O | H | Me | OMe | N | |
| I-349 | Me | CH₂Cl | H | O | H | OMe | OMe | CH | |
| I-350 | Me | CH₂Cl | H | O | H | Me | OMe | CH | |
| I-351 | Me | CH₂Cl | H | O | H | Me | OMe | N | |
| I-352 | Me | CH₂F | H | O | H | OMe | OMe | CH | |
| I-353 | Me | CH₂F | H | O | H | Me | OMe | H | |
| I-354 | Me | CH₂F | H | O | H | Me | OMe | N | |
| I-355 | Me | CH₂OMe | H | O | H | OMe | OMe | CH | |
| I-356 | Me | CH₂OMe | H | O | H | Me | OMe | CH | |
| I-357 | Me | CH₂OMe | H | O | H | Me | OMe | N | |
| I-358 | Me | CH₂CF₃ | H | O | H | OMe | OMe | CH | |
| I-359 | Me | CH₂CF₃ | H | O | H | Me | OMe | CH | |
| I-360 | Me | CH₂CF₃ | H | O | H | Me | OMe | N | |
| I-361 | Me |  | H | O | H | OMe | OMe | CH | |
| I-362 | Me |  | H | O | H | Me | OMe | CH | |
| I-363 | Me |  | H | O | H | Me | OMe | N | |
| I-364 | Me | CH₂CH₂CF₃ | H | O | H | OMe | OMe | CH | |
| I-365 | Me | CH₂CH₂CF₃ | H | O | H | Me | OMe | CH | |
| I-366 | Me | CH₂CH₂CF₃ | H | O | H | Me | OMe | N | |
| I-367 | Me | CH₂CH=CH₂ | H | O | H | OMe | OMe | CH | |
| I-368 | Me | CH₂CH=CH₂ | H | O | H | Me | OMe | CH | |
| I-369 | Me | CH₂CH=CH₂ | H | O | H | Me | OMe | N | |

TABLE 1-continued

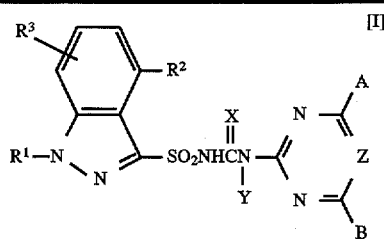

| Comp. NO. | R¹ | R² | R³ | X | Y | A | B | Z | Mp. (°C.) |
|---|---|---|---|---|---|---|---|---|---|
| I-370 | Me | CH₂C≡CH | H | O | H | OMe | OMe | CH | |
| I-371 | Me | CH₂C≡CH | H | O | H | Me | OMe | CH | |
| I-372 | Me | CH₂C≡CH | H | O | H | Me | OMe | N | |
| I-373 | Me | CH₂COOMe | H | O | H | OMe | OMe | CH | |
| I-374 | Me | CH₂COOMe | H | O | H | Me | OMe | CH | |
| I-375 | Me | CH₂COOMe | H | O | H | Me | OMe | N | |
| I-376 | Me | CH₂COOEt | H | O | H | OMe | OMe | CH | |
| I-377 | Me | CH₂COOEt | H | O | H | Me | OMe | CH | |
| I-378 | Me | CH₂COOEt | H | O | H | Me | OMe | N | |
| I-379 | Me | CH₂CN | H | O | H | OMe | OMe | CH | |
| I-380 | Me | CH₂CN | H | O | H | Me | OMe | CH | |
| I-381 | Me | CH₂CN | H | O | H | Me | OMe | N | |
| I-382 | Me | CH₂CONMe₂ | H | O | H | OMe | OMe | CH | |
| I-383 | Me | CH₂CONMe₂ | H | O | H | Me | OMe | CH | |
| I-384 | Me | CH₂CONMe₂ | H | O | H | Me | OMe | N | |
| I-385 | Me | CH₂SO₂NMe₂ | H | O | H | OMe | OMe | CH | |
| I-386 | Me | CH₂SO₂NMe₂ | H | O | H | Me | OMe | CH | |
| I-387 | Me | CH₂SO₂NMe₂ | H | O | H | Me | OMe | N | |
| I-388 | Me | CH₂NMe₂ | H | O | H | OMe | OMe | CH | |
| I-389 | Me | CH₂NMe₂ | H | O | H | Me | OMe | CH | |
| I-390 | Me | CH₂NMe₂ | H | O | H | Me | OMe | N | |
| I-391 | Me | CH=CH₂ | H | O | H | OMe | OMe | CH | |
| I-392 | Me | CH=CH₂ | H | O | H | Me | OMe | CH | |
| I-393 | Me | CH=CH₂ | H | O | H | Me | OMe | N | |
| I-394 | Me | CH=CHMe | H | O | H | OMe | OMe | CH | |
| I-395 | Me | CH=CHMe | H | O | H | Me | OMe | CH | |
| I-396 | Me | CH=CHMe | H | O | H | Me | OMe | N | |
| I-397 | Me | C≡CH | H | O | H | OMe | OMe | CH | |
| I-398 | Me | C≡CH | H | O | H | Me | OMe | CH | |
| I-399 | Me | C≡CH | H | O | H | Me | OMe | N | |
| I-400 | Me | C≡CMe | H | O | H | OMe | OMe | CH | |
| I-401 | Me | C≡CMe | H | O | H | Me | OMe | CH | |
| I-402 | Me | C≡CMe | H | O | H | Me | OMe | N | |
| I-403 | Me | CH=CH—COOMe | H | O | H | OMe | OMe | CH | |
| I-404 | Me | CH=CH—COOMe | H | O | H | Me | OMe | CH | |
| I-405 | Me | CH=CH—COOMe | H | O | H | Me | OMe | N | |
| I-406 | Me | CH(Me)COMe | H | O | H | OMe | OMe | CH | |
| I-407 | Me | CH(Me)COMe | H | O | H | Me | OMe | CH | |
| I-408 | Me | CH(Me)COMe | H | O | H | Me | OMe | N | |
| I-409 | Me | CH(Me)COEt | H | O | H | OMe | OMe | CH | |
| I-410 | Me | CH(Me)COEt | H | O | H | Me | OMe | CH | |
| I-411 | Me | CH(Me)COEt | H | O | H | Me | OMe | N | |
| I-412 | Me | CH(Et)COMe | H | O | H | OMe | OMe | CH | |
| I-413 | Me | CH(Et)COMe | H | O | H | Me | OMe | CH | |
| I-414 | Me | CH(Et)COMe | H | O | H | Me | OMe | N | |
| I-415 | Me | CH(Et)COEt | H | O | H | OMe | OMe | CH | |
| I-416 | Me | CH(Et)COEt | H | O | H | Me | OMe | CH | |
| I-417 | Me | CH(Et)COEt | H | O | H | Me | OMe | N | |
| I-418 | Me | CO—◁ | H | O | H | OMe | OMe | CH | |
| I-419 | Me | CO—◁ | H | O | H | Me | OMe | CH | |
| I-420 | Me | CO—◁ | H | O | H | Me | OMe | N | |

TABLE 1-continued

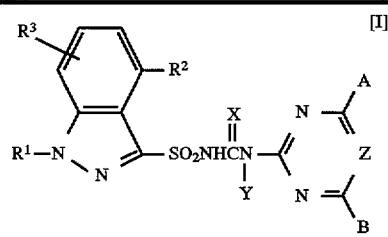

| Comp. NO. | R¹ | R² | R³ | X | Y | A | B | Z | Mp. (°C.) |
|---|---|---|---|---|---|---|---|---|---|
| I-421 | Me | COPr | H | O | H | OMe | OMe | CH | |
| I-422 | Me | COPr | H | O | H | Me | OMe | CH | |
| I-423 | Me | COPr | H | O | H | Me | OMe | N | |
| I-424 | Me | COPr-i | H | O | H | OMe | OMe | CH | |
| I-425 | Me | COPr-i | H | O | H | Me | OMe | CH | |
| I-426 | Me | COPr-i | H | O | H | Me | OMe | N | |
| I-427 | Me | CH=NOMe | H | O | H | OMe | OMe | CH | |
| I-428 | Me | CH=NOMe | H | O | H | Me | OMe | CH | |
| I-429 | Me | CH=NOMe | H | O | H | Me | OMe | N | |
| I-430 | Me | CH=NOEt | H | O | H | OMe | OMe | CH | |
| I-431 | Me | CH=NOEt | H | O | H | Me | OMe | CH | |
| I-432 | Me | CH=NOEt | H | O | H | Me | OMe | N | |
| I-433 | Me | C(Me)=NOMe | H | O | H | OMe | OMe | CH | |
| I-434 | Me | C(Me)=NOMe | H | O | H | Me | OMe | CH | |
| I-435 | Me | C(Me)=NOMe | H | O | H | Me | OMe | N | |
| I-436 | Me | C(Me)=NOEt | H | O | H | OMe | OMe | CH | |
| I-437 | Me | C(Me)=NOEt | H | O | H | Me | OMe | CH | |
| I-438 | Me | C(Me)=NOEt | H | O | H | Me | OMe | N | |
| I-439 | Me | C(Me)=NOPr | H | O | H | OMe | OMe | CH | |
| I-440 | Me | C(Me)=NOPr | H | O | H | Me | OMe | CH | |
| I-441 | Me | C(Me)=NOPr | H | O | H | Me | OMe | N | |
| I-442 | Me | C(Me)=NOCH$_2$CH$_2$Cl | H | O | H | OMe | OMe | CH | |
| I-443 | Me | C(Me)=NOCH$_2$CH$_2$Cl | H | O | H | Me | OMe | CH | |
| I-444 | Me | C(Me)=NOCH$_2$CH$_2$Cl | H | O | H | Me | OMe | N | |
| I-445 | Me | C(Me)=NOCH$_2$CH$_2$F | H | O | H | OMe | OMe | CH | |
| I-446 | Me | C(Me)=NOCH$_2$CH$_2$F | H | O | H | Me | OMe | CH | |
| I-447 | Me | C(Me)=NOCH$_2$CH$_2$F | H | O | H | Me | OMe | N | |
| I-448 | Me | NHEt | H | O | H | OMe | OMe | CH | |
| I-449 | Me | NHEt | H | O | H | Me | OMe | CH | |
| I-450 | Me | NHEt | H | O | H | Me | OMe | N | |
| I-451 | Me | NHPr | H | O | H | OMe | OMe | CH | |
| I-452 | Me | NHPr | H | O | H | Me | OMe | CH | |
| I-453 | Me | NHPr | H | O | H | Me | OMe | N | |
| I-454 | Me | NHCOOMe | H | O | H | OMe | OMe | CH | |
| I-455 | Me | NHCOOMe | H | O | H | Me | OMe | CH | |
| I-456 | Me | NHCOOMe | H | O | H | Me | OMe | N | |
| I-457 | Me | NHCOOEt | H | O | H | OMe | OMe | CH | |
| I-458 | Me | NHCOOEt | H | O | H | Me | OMe | CH | |
| I-459 | Me | NHCOOEt | H | O | H | Me | OMe | N | |
| I-460 | Me | NHCOOPh | H | O | H | OMe | OMe | CH | |
| I-461 | Me | NHCOOPh | H | O | H | Me | OMe | CH | |
| I-462 | Me | NHCOOPh | H | O | H | Me | OMe | N | |
| I-463 | Me | N(Me)SO$_2$Me | H | O | H | OMe | OMe | CH | |
| I-464 | Me | N(Me)SO$_2$Me | H | O | H | Me | OMe | CH | |
| I-465 | Me | N(Me)SO$_2$Me | H | O | H | Me | OMe | N | |
| I-466 | Me | N(Et)SO$_2$Me | H | O | H | OMe | OMe | CH | |
| I-467 | Me | N(Et)SO$_2$Me | H | O | H | Me | OMe | CH | |
| I-468 | Me | N(Et)SO$_2$Me | H | O | H | Me | OMe | N | |
| I-469 | Me | N(Me)SO$_2$Et | H | O | H | OMe | OMe | CH | |
| I-470 | Me | N(Me)SO$_2$Et | H | O | H | Me | OMe | CH | |
| I-471 | Me | N(Me)SO$_2$Et | H | O | H | Me | OMe | N | |
| I-472 | Me | N(Et)SO$_2$Et | H | O | H | OMe | OMe | CH | |
| I-473 | Me | N(Et)SO$_2$Et | H | O | H | Me | OMe | CH | |
| I-474 | Me | N(Et)SO$_2$Et | H | O | H | Me | OMe | N | |
| I-475 | Me | NHCOEt | H | O | H | OMe | OMe | CH | |
| I-476 | Me | NHCOEt | H | O | H | Me | OMe | CH | |
| I-477 | Me | NHCOEt | H | O | H | Me | OMe | N | |
| I-478 | Me | NHCOCF$_3$ | H | O | H | OMe | OMe | CH | |
| I-479 | Me | NHCOCF$_3$ | H | O | H | Me | OMe | CH | |
| I-480 | Me | NHCOCF$_3$ | H | O | H | Me | OMe | N | |
| I-481 | Me | N=CHMe | H | O | H | OMe | OMe | CH | |
| I-482 | Me | N=CHMe | H | O | H | Me | OMe | CH | |
| I-483 | Me | N=CHMe | H | O | H | Me | OMe | N | |
| I-484 | Me | N=CH—Ph | H | O | H | OMe | OMe | CH | |
| I-485 | Me | N=CH—Ph | H | O | H | Me | OMe | CH | |

TABLE 1-continued

[Structure I: R³-substituted phenyl with R², R¹-N-N pyrazole-SO₂NHCN(X)(Y)-C(=N-A)(Z)-C(=N-B), formula I]

| Comp. NO. | R¹ | R² | R³ | X | Y | A | B | Z | Mp. (°C.) |
|---|---|---|---|---|---|---|---|---|---|
| I-486 | Me | N=CH—Ph | H | O | H | Me | OMe | N | |
| I-487 | Me | N₃ | H | O | H | OMe | OMe | CH | |
| I-488 | Me | N₃ | H | O | H | Me | OMe | CH | |
| I-489 | Me | N₃ | H | O | H | Me | OMe | N | |
| I-490 | Me | I | H | O | H | OMe | OMe | CH | |
| I-491 | Me | I | H | O | H | Me | OMe | CH | |
| I-492 | Me | I | H | O | H | Me | OMe | N | |
| I-493 | Me | OCOEt | H | O | H | OMe | OMe | CH | |
| I-494 | Me | OCOEt | H | O | H | Me | OMe | CH | |
| I-495 | Me | OCOEt | H | O | H | Me | OMe | N | |
| I-496 | Me | OCOPr | H | O | H | OMe | OMe | CH | |
| I-497 | Me | OCOPr | H | O | H | Me | OMe | CH | |
| I-498 | Me | OCOPr | H | O | H | Me | OMe | N | |
| I-499 | Me | OCOPh | H | O | H | OMe | OMe | CH | |
| I-500 | Me | OCOPh | H | O | H | Me | OMe | CH | |
| I-501 | Me | OCOPh | H | O | H | Me | OMe | N | |
| I-502 | Me | OCONMe₂ | H | O | H | OMe | OMe | CH | |
| I-503 | Me | OCONMe₂ | H | O | H | Me | OMe | CH | |
| I-504 | Me | OCONMe₂ | H | O | H | Me | OMe | N | |
| I-505 | Me | Cl | H | O | H | CF₃ | OMe | CH | |
| I-506 | Me | OPr-i | H | O | H | Cl | OMe | CH | 163–165 |
| I-507 | Me | SEt | H | O | H | Me | OMe | CH | 225–227 |
| I-508 | Me | SEt | H | O | H | Cl | OMe | CH | 185–187 |
| I-509 | Me | SEt | H | O | H | Me | Me | CH | 220–222 |
| I-510 | Me | SEt | H | O | H | OMe | OMe | N | 173–175 |
| I-511 | Me | SBu | H | O | H | OMe | Me | CH | 157–160 |
| I-512 | Me | SBu | H | O | H | OMe | Me | N | 155–157 |
| I-513 | Me | SPr-i | H | O | H | OMe | Me | CH | 185–187 |
| I-514 | Me | SPr-i | H | O | H | OMe | Me | N | 228–229 |
| I-515 | Me | SOEt | H | O | H | OMe | OMe | N | 180–182 |
| I-516 | Me | SO₂Et | H | O | H | OMe | Me | CH | 270–272 |
| I-517 | Me | SO₂Et | H | O | H | OMe | Me | N | 165–168 |
| I-518 | Me | SO₂Et | H | O | H | OMe | Cl | CH | 272–275 |
| I-519 | Me | SO₂Pr | H | O | H | OMe | Me | CH | 265–267 |
| I-520 | Me | SO₂Pr | H | O | H | OMe | Me | N | 132–135 |
| I-521 | Me | SO₂Pr | H | O | H | OMe | Cl | CH | 142–145 |
| I-522 | Me | SO₂Bu | H | O | H | OMe | Me | CH | 243–246 |
| I-523 | Me | SO₂Bu | H | O | H | OMe | Me | N | 241–243 |
| I-524 | Me | SO₂Bu | H | O | H | OMe | Cl | CH | 245–247 |
| I-525 | Me | SO₂Pr-i | H | O | H | OMe | Me | CH | 135–139 |
| I-526 | Me | SO₂Pr-i | H | O | H | OMe | Me | N | 281–282 |
| I-527 | Me | COOPr | H | O | H | OMe | Me | N | 187–189 |
| I-528 | Me | NO₂ | H | O | H | OMe | Cl | CH | 204–206 |
| I-529 | Me | CONMe₂ | H | O | H | OMe | Me | CH | 161–164 |
| I-530 | Me | Br | H | O | H | OMe | Cl | CH | 276–279 |
| I-531 | Me | OCH₂-cyclopropyl | H | O | H | OMe | OMe | CH | |
| I-532 | Me | OCH₂—Bu-t | H | O | H | OMe | OMe | CH | |
| I-533 | Me | OCH₂—Bu-t | H | O | H | Me | OMe | CH | |
| I-534 | Me | OCH₂CH=CMe₂ | H | O | H | OMe | OMe | CH | |
| I-535 | Me | OCH₂CH₂CH₂F | H | O | H | OMe | OMe | CH | |
| I-536 | Me | OCH₂CH₂CH₂F | H | O | H | Me | OMe | CH | |
| I-537 | Me | OCH₂CH₂CH₂F | H | O | H | Me | OMe | N | |
| I-538 | Me | CH₂CH₂N₃ | H | O | H | OMe | OMe | CH | |
| I-539 | Me | CH₂CO-cyclopropyl | H | O | H | OMe | OMe | CH | |
| I-540 | Me | COCF₃ | H | O | H | OMe | OMe | CH | |
| I-541 | Me | COOCH₂CH=CHCl | H | O | H | OMe | OMe | CH | |
| I-542 | Me | SO₂CF₃ | H | O | H | OMe | OMe | CH | |
| I-543 | Me | OCOCF₃ | H | O | H | OMe | OMe | CH | |
| I-544 | Me | OCH₂OPh | H | O | H | OMe | OMe | CH | |

TABLE 1-continued

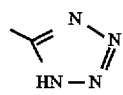

| Comp. NO. | R¹ | R² | R³ | X | Y | A | B | Z | Mp. (°C.) |
|---|---|---|---|---|---|---|---|---|---|
| I-545 | Me | CH=NOH | H | O | H | OMe | OMe | CH | |
| I-546 | Me | CH=NOCH$_2$CH=CH$_2$ | H | O | H | OMe | OMe | CH | |
| I-547 | Me | CH=NOCH$_2$C≡CH | H | O | H | OMe | OMe | CH | |
| I-548 | Me | C(Me)=NOBn | H | O | H | OMe | OMe | CH | |
| I-549 | Me | C(Me)=NOPh | H | O | H | OMe | OMe | CH | |
| I-550 | Me | C(Bn)=NOMe | H | O | H | OMe | OMe | CH | |
| I-551 | Me | C(Ph)=NOMe | H | O | H | OMe | OMe | CH | |
| I-552 | Me | C(CF$_3$)=NOMe | H | O | H | OMe | OMe | CH | |
| I-553 | Me | COOCH$_2$CH$_2$Cl | H | O | H | OMe | OMe | CH | |
| I-554 | Me | COOCH$_2$CF$_3$ | H | O | H | OMe | OMe | CH | |
| I-555 | Me | Cl | 5-Cl | O | H | OMe | Me | N | 182–184 |
| I-556 | Me | Cl | 5-OMe | O | H | OMe | OMe | CH | |
| I-557 | Me | Cl | 5-F | O | H | OMe | OMe | CH | |
| I-558 | Me | F | 5-Cl | O | H | OMe | OMe | CH | |
| I-559 | Me | F | 5-F | O | H | OMe | OMe | CH | |
| I-560 | Me | COOMe | 5-Cl | O | H | OMe | OMe | CH | |
| I-561 | Me | COOEt | 5-Cl | O | H | OMe | OMe | CH | |
| I-562 | Me | COOPr | 5-Cl | O | H | OMe | OMe | CH | |
| I-563 | Me | COOPr-i | 5-Cl | O | H | OMe | OMe | CH | |
| I-564 | Me | OMe | 5-COOMe | O | H | OMe | OMe | CH | |
| I-565 | Me | COOMe | 5-OMe | O | H | OMe | OMe | CH | |
| I-566 | Me | H | 5-CN | O | H | OMe | OMe | CH | |
| I-567 | Me | H | 5-CF | O | H | OMe | OMe | CH | |
| I-568 | Me | H | 5-COOMe | O | H | OMe | OMe | CH | 235–236 |
| I-569 | Me | H | 5-COOEt | O | H | OMe | OMe | CH | |
| I-570 | Me | H | 5-COOPr | O | H | OMe | OMe | CH | |
| I-571 | Me | H | 5-COOPr-i | O | H | OMe | OMe | CH | |
| I-572 | Me | H | 5-COOCH$_2$CH$_2$Cl | O | H | OMe | OMe | CH | |
| I-573 | Me | H | 5-COOCH$_2$CH$_2$F | O | H | OMe | OMe | CH | |
| I-574 | Me | H | 5-COOCH$_2$CF$_3$ | O | H | OMe | OMe | CH | |
| I-575 | Me | H | 5-COOCH$_2$OMe | O | H | OMe | OMe | CH | |
| I-576 | Me | H | 5-CONMe$_2$ | O | H | OMe | OMe | CH | |
| I-577 | Me | H | 5-OCH$_2$CH$_2$F | O | H | OMe | OMe | CH | |
| I-578 | Me | H | 5-OCHF$_2$ | O | H | OMe | OMe | CH | |
| I-579 | Me | H | 5-OCH$_2$CF$_3$ | O | H | OMe | OMe | CH | |
| I-580 | Me | H | 5-OCH$_2$CH$_2$CH$_2$F | O | H | OMe | OMe | CH | |
| I-581 | Me | H | 5-OCH$_2$CH=CH$_2$ | O | H | OMe | OMe | CH | |
| I-582 | Me | H | 5-OCH$_2$C≡CH | O | H | OMe | OMe | CH | |
| I-583 | Me | H | 5-NO$_2$ | O | H | OMe | OMe | CH | |
| I-584 | Me | H | 5-SMe | O | H | OMe | OMe | CH | |
| I-585 | Me | H | 5-SEt | O | H | OMe | OMe | CH | |
| I-586 | Me | H | 5-SPr | O | H | OMe | OMe | CH | |
| I-587 | Me | H | 5-SPr-i | O | H | OMe | OMe | CH | |
| I-588 | Me | H | 5-SO$_2$Et | O | H | OMe | OMe | CH | |
| I-589 | Me | H | 5-SO$_2$Pr | O | H | OMe | OMe | CH | |
| I-590 | Me | H | 5-SO$_2$Pr-i | O | H | OMe | OMe | CH | |
| I-591 | Me | H | 5-SOEt | O | H | OMe | OMe | CH | |
| I-592 | Me | H | 5-Me | O | H | OMe | OMe | CH | |
| I-593 | Me | H | 5-Et | O | H | OMe | OMe | CH | |
| I-594 | Me | H | 5-Pr | O | H | OMe | OMe | CH | |
| I-595 | Me | H | 5-SO$_2$NMe$_2$ | O | H | OMe | OMe | CH | |
| I-596 | Me | H | 5-OCF$_3$ | O | H | OMe | OMe | CH | |
| I-597 | Me | H | 5-CH$_2$CF$_3$ | O | H | OMe | OMe | CH | |
| I-598 | Me | H | 5-CH$_2$CH=CH$_2$ | O | H | OMe | OMe | CH | |
| I-599 | Me | H | 5-COOMe | O | H | OMe | Me | CH | 134–135 |
| I-600 | Me | H | 5-COOMe | O | H | OMe | Me | N | 143–144 |
| I-601 | Me | H | 5-COOMe | O | H | OMe | OMe | N | 148–150 |
| I-602 | Me | =) | H | O | H | OMe | OMe | CH | |

TABLE 1-continued

[Structure I: R³ and R² substituted benzene fused to pyrazole with R¹-N, connected via SO₂NHC(X)N(Y) to a pyrimidine ring with A, B, Z]

| Comp. NO. | R¹ | R² | R³ | X | Y | A | B | Z | Mp. (°C.) |
|---|---|---|---|---|---|---|---|---|---|
| I-603 | Me | (1H-tetrazol-5-yl, HN—N) | H | O | H | Me | OMe | CH | |
| I-604 | Me | (1H-tetrazol-5-yl, HN—N) | H | O | H | Me | OMe | N | |
| I-605 | Me | (2-Me-tetrazol-5-yl, Me—N—N) | H | O | H | OMe | OMe | CH | |
| I-606 | Me | (2-Me-tetrazol-5-yl, Me—N—N) | H | O | H | Me | OMe | CH | |
| I-607 | Me | (2-Me-tetrazol-5-yl, Me—N—N) | H | O | H | Me | OMe | N | |
| I-608 | Me | (N-Me-triazolyl, N=N) | H | O | H | OMe | OMe | CH | |
| I-609 | Me | (N-Me-triazolyl, N=N) | H | O | H | Me | OMe | CH | |
| I-610 | Me | (N-Me-triazolyl, N=N) | H | O | H | Me | OMe | N | |
| I-611 | Me | —O—C₂H₄—O—* | | O | H | OMe | OMe | CH | |
| I-612 | Me | —O—C₂H₄—O—* | | O | H | Me | OMe | CH | |
| I-613 | Me | —O—C₂H₄—O—* | | O | H | Me | OMe | N | |
| I-614 | Me | —S—C₂H₄—S—* | | O | H | OMe | OMe | CH | |
| I-615 | Me | —S—C₂H₄—S—* | | O | H | Me | OMe | CH | |
| I-616 | Me | —S—C₂H₄—S—* | | O | H | Me | OMe | N | |
| I-617 | Me | —O—CH₂—O—* | | O | H | OMe | OMe | CH | |
| I-618 | (2-pyridyl) | Cl | H | O | H | OMe | OMe | CH | |
| I-619 | (3-pyridyl) | Cl | H | O | H | OMe | OMe | CH | |
| I-620 | (4-pyridyl) | Cl | H | O | H | OMe | OMe | CH | |
| I-621 | COMe | Cl | H | O | H | OMe | OMe | CH | |
| I-622 | COEt | Cl | H | O | H | OMe | OMe | CH | |
| I-623 | COPr | Cl | H | O | H | OMe | OMe | CH | |

TABLE 1-continued

| Comp. NO. | R¹ | R² | R³ | X | Y | A | B | Z | Mp. (°C.) |
|---|---|---|---|---|---|---|---|---|---|
| I-624 | COPr-i | Cl | H | O | H | OMe | OMe | CH | |
| I-625 | COPh | Cl | H | O | H | OMe | OMe | CH | |
| I-626 | SO$_2$Me | Cl | H | O | H | OMe | OMe | CH | |
| I-627 | SO$_2$Et | Cl | H | O | H | OMe | OMe | CH | |
| I-628 | SO$_2$Ph | Cl | H | O | H | OMe | OMe | CH | |
| I-629 | COOMe | Cl | H | O | H | OMe | OMe | CH | |
| I-630 | COOEt | Cl | H | O | H | OMe | OMe | CH | |
| I-631 | COOPh | Cl | H | O | H | OMe | OMe | CH | |
| I-632 | CONMe$_2$ | Cl | H | O | H | OMe | OMe | CH | |
| I-633 | SO$_2$NMe$_2$ | Cl | H | O | H | OMe | OMe | CH | |
| I-634 | Ph | Cl | H | O | H | Me | OMe | N | |
| I-635 | CH$_2$OMe | Cl | H | O | H | OMe | OMe | CH | |
| I-636 | CH$_2$OBn | Cl | H | O | H | OMe | OMe | CH | |
| I-637 | CH$_2$CH$_2$F | Cl | H | O | H | OMe | OMe | CH | |
| I-638 | CH$_2$CH$_2$Cl | Cl | H | O | H | OMe | OMe | CH | |
| I-639 | CF$_3$ | Cl | H | O | H | OMe | OMe | CH | |
| I-640 | CH$_2$F | Cl | H | O | H | OMe | OMe | CH | |
| I-641 | CH$_2$CH=CH$_2$ | OMe | H | O | H | OMe | OMe | CH | 221–223 |
| I-642 | COCF$_3$ | Cl | H | O | H | OMe | OMe | CH | |
| I-643 | ◁ | Cl | H | O | H | OMe | OMe | CH | |
| I-644 | H | Bn | H | O | H | Ome | OMe | CH | |
| I-645 | H | Br | H | O | H | OMe | Me | CH | 183–184 |
| I-646 | H | Br | H | O | H | OMe | Me | N | 154–155 |
| I-647 | H | Br | H | O | H | Ome | OMe | CH | |
| I-648 | H | Bu | H | O | H | Me | OMe | CH | |
| I-649 | H | Bu | H | O | H | Me | OMe | N | |
| I-650 | H | Bu | H | O | H | OMe | OMe | CH | |
| I-651 | H | Bu-t | H | O | H | Me | OMe | CH | |
| I-652 | H | Bu-t | H | O | H | Me | OMe | N | |
| I-653 | H | Bu-t | H | O | H | OMe | OMe | CH | |
| I-654 | H | C(Me)=NOCH$_2$CH$_2$Cl | H | O | H | Me | OMe | CH | |
| I-655 | H | C(Me)=NOCH$_2$CH$_2$Cl | H | O | H | Me | OMe | N | |
| I-656 | H | C(Me)=NOCH$_2$CH$_2$Cl | H | O | H | OMe | OMe | CH | |
| I-657 | H | C(Me)=NOCH$_2$CH$_2$F | H | O | H | Me | OMe | CH | |
| I-658 | H | C(Me)=NOCH$_2$CH$_2$F | H | O | H | Me | OMe | N | |
| I-659 | H | C(Me)=NOCH$_2$CH$_2$F | H | O | H | OMe | OMe | CH | |
| I-660 | H | C(Me)=NOEt | H | O | H | Me | OMe | CH | |
| I-661 | H | C(Me)=NOEt | H | O | H | Me | OMe | N | |
| I-662 | H | C(Me)=NOEt | H | O | H | OMe | OMe | CH | |
| I-663 | H | C(Me)=NOMe | H | O | H | Me | OMe | CH | |
| I-664 | H | C(Me)=NOMe | H | O | H | Me | OMe | N | |
| I-665 | H | C(Me)=NOMe | H | O | H | OMe | OMe | CH | |
| I-666 | H | C(Me)=NOPr | H | O | H | Me | OMe | CH | |
| I-667 | H | C(Me)=NOPr | H | O | H | Me | OMe | N | |
| I-668 | H | C(Me)=NOPr | H | O | H | OMe | OMe | CH | |
| I-669 | H | C≡CH | H | O | H | Me | OMe | CH | |
| I-670 | H | C≡CH | H | O | H | Me | OMe | N | |
| I-671 | H | C≡CH | H | O | H | OMe | OMe | CH | |
| I-672 | H | C≡CMe | H | O | H | Me | OMe | CH | |
| I-673 | H | C≡CMe | H | O | H | Me | OMe | N | |
| I-674 | H | C≡CMe | H | O | H | OMe | OMe | CH | |
| I-675 | H | CF$_3$ | H | O | H | OMe | OMe | CH | |
| I-676 | H | CH(Et)COEt | H | O | H | Me | OMe | CH | |
| I-677 | H | CH(Et)COEt | H | O | H | Me | OMe | N | |
| I-678 | H | CH(Et)COEt | H | O | H | OMe | OMe | CH | |
| I-679 | H | CH(Et)COMe | H | O | H | Me | OMe | CH | |
| I-680 | H | CH(Et)COMe | H | O | H | Me | OMe | N | |

TABLE 1-continued

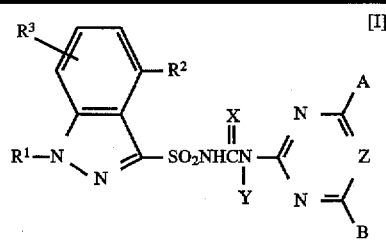

| Comp. NO. | R¹ | R² | R³ | X | Y | A | B | Z | Mp. (°C.) |
|---|---|---|---|---|---|---|---|---|---|
| I-681 | H | CH(Et)COMe | H | O | H | OMe | OMe | CH | |
| I-682 | H | CH(Me)COEt | H | O | H | Me | OMe | CH | |
| I-683 | H | CH(Me)COEt | H | O | H | Me | OMe | N | |
| I-684 | H | CH(Me)COEt | H | O | H | OMe | OMe | CH | |
| I-685 | H | CH(Me)COMe | H | O | H | Me | OMe | CH | |
| I-686 | H | CH(Me)COMe | H | O | H | Me | OMe | N | |
| I-687 | H | CH(Me)COMe | H | O | H | OMe | OMe | CH | |
| I-688 | H | CH=CH—COOMe | H | O | H | Me | OMe | CH | |
| I-689 | H | CH=CH—COOMe | H | O | H | Me | OMe | N | |
| I-690 | H | CH=CH—COOMe | H | O | H | OMe | OMe | CH | |
| I-691 | H | CH=CH$_2$ | H | O | H | Me | OMe | CH | |
| I-692 | H | CH=CH$_2$ | H | O | H | Me | OMe | N | |
| I-693 | H | CH=CH$_2$ | H | O | H | OMe | OMe | CH | |
| I-694 | H | CH=CHMe | H | O | H | Me | OMe | CH | |
| I-695 | H | CH=CHMe | H | O | H | Me | OMe | N | |
| I-696 | H | CH=CHMe | H | O | H | OMe | OMe | CH | |
| I-697 | H | CH=NOEt | H | O | H | Me | OMe | CH | |
| I-698 | H | CH=NOEt | H | O | H | Me | OMe | N | |
| I-699 | H | CH=NOEt | H | O | H | OMe | OMe | CH | |
| I-700 | H | CH=NOMe | H | O | H | Me | OMe | CH | |
| I-701 | H | CH=NOMe | H | O | H | Me | OMe | N | |
| I-702 | H | CH=NOMe | H | O | H | OMe | OMe | CH | |
| I-703 | H | CH$_2$C≡CH | H | O | H | Me | OMe | CH | |
| I-704 | H | CH$_2$C≡CH | H | O | H | Me | OMe | N | |
| I-705 | H | CH$_2$C≡CH | H | O | H | OMe | OMe | CH | |
| I-706 | H | CH$_2$CF$_3$ | H | O | H | Me | OMe | CH | |
| I-707 | H | CH$_2$CF$_3$ | H | O | H | Me | OMe | N | |
| I-708 | H | CH$_2$CF$_3$ | H | O | H | OMe | OMe | CH | |
| I-709 | H | CH$_2$CH=CH$_2$ | H | O | H | Me | OMe | CH | |
| I-710 | H | CH$_2$CH=CH$_2$ | H | O | H | Me | OMe | N | |
| I-711 | H | CH$_2$CH=CH$_2$ | H | O | H | OMe | OMe | CH | |
| I-712 | H | CH$_2$CH$_2$CF$_3$ | H | O | H | Me | OMe | CH | |
| I-713 | H | CH$_2$CH$_2$CF$_3$ | H | O | H | Me | OMe | N | |
| I-714 | H | CH$_2$CH$_2$CF$_3$ | H | O | H | OMe | OMe | CH | |
| I-715 | H | CH$_2$CN | H | O | H | Me | OMe | CH | |
| I-716 | H | CH$_2$CN | H | O | H | Me | OMe | N | |
| I-717 | H | CH$_2$CN | H | O | H | OMe | OMe | CH | |
| I-718 | H | CH$_2$CONMe$_2$ | H | O | H | Me | OMe | CH | |
| I-719 | H | CH$_2$CONMe$_2$ | H | O | H | Me | OMe | N | |
| I-720 | H | CH$_2$CONMe$_2$ | H | O | H | OMe | OMe | CH | |
| I-721 | H | CH$_2$COOEt | H | O | H | Me | OMe | CH | |
| I-722 | H | CH$_2$COOEt | H | O | H | Me | OMe | N | |
| I-723 | H | CH$_2$COOEt | H | O | H | OMe | OMe | CH | |
| I-724 | H | CH$_2$COOMe | H | O | H | Me | OMe | CH | |
| I-725 | H | CH$_2$COOMe | H | O | H | Me | OMe | N | |
| I-726 | H | CH$_2$COOMe | H | O | H | OMe | OMe | CH | |
| I-727 | H | CH$_2$Cl | H | O | H | Me | OMe | CH | |
| I-728 | H | CH$_2$Cl | H | O | H | Me | OMe | N | |
| I-729 | H | CH$_2$Cl | H | O | H | OMe | OMe | CH | |
| I-730 | H | CH$_2$F | H | O | H | Me | OMe | CH | |
| I-731 | H | CH$_2$F | H | O | H | Me | OMe | N | |
| I-732 | H | CH$_2$F | H | O | H | OMe | OMe | CH | |
| I-733 | H | CH$_2$NMe$_2$ | H | O | H | Me | OMe | CH | |
| I-734 | H | CH$_2$NMe$_2$ | H | O | H | Me | OMe | N | |
| I-735 | H | CH$_2$NMe$_2$ | H | O | H | OMe | OMe | CH | |
| I-736 | H | CH$_2$OMe | H | O | H | Me | OMe | CH | |
| I-737 | H | CH$_2$OMe | H | O | H | Me | OMe | N | |
| I-738 | H | CH$_2$OMe | H | O | H | OMe | OMe | CH | |
| I-739 | H | CH$_2$SO$_2$NMe$_2$ | H | O | H | Me | OMe | CH | |
| I-740 | H | CH$_2$SO$_2$NMe$_2$ | H | O | H | Me | OMe | N | |
| I-741 | H | CH$_2$SO$_2$NMe$_2$ | H | O | H | OMe | OMe | CH | |
| I-742 | H | CN | H | O | H | OMe | Me | CH | |
| I-743 | H | CN | H | O | H | OMe | Me | N | |

TABLE 1-continued

[Structure I: pyrazole-benzene-SO2NHC(=X)N(Y)-pyrimidine/triazine with substituents R1, R2, R3, A, B, Z]

| Comp. NO. | R¹ | R² | R³ | X | Y | A | B | Z | Mp. (°C.) |
|---|---|---|---|---|---|---|---|---|---|
| I-744 | H | CN | H | O | H | OMe | OMe | CH | |
| I-745 | H | CO—◁ | H | O | H | Me | OMe | CH | |
| I-746 | H | CO—◁ | H | O | H | Me | OMe | N | |
| I-747 | H | CO—◁ | H | O | H | OMe | OMe | CH | |
| I-748 | H | CO₂Bn | H | O | H | OMe | OMe | CH | |
| I-749 | H | CO₂Bu | H | O | H | OMe | Me | CH | |
| I-750 | H | CO₂Bu | H | O | H | OMe | Me | N | |
| I-751 | H | CO₂Bu | H | O | H | OMe | OMe | CH | |
| I-752 | H | CO₂CH₂C≡CH | H | O | H | OMe | OMe | CH | |
| I-753 | H | CO₂CH₂CH=CH₂ | H | O | H | OMe | OMe | CH | |
| I-754 | H | CO₂CH₂CH₂F | H | O | H | OMe | OMe | CH | |
| I-755 | H | CO₂Et | H | O | H | OCHF₂ | OCHF₂ | CH | |
| I-756 | H | CO₂Et | H | O | H | OMe | Me | N | |
| I-757 | H | CO₂Et | H | S | H | OMe | OMe | CH | |
| I-758 | H | CO₂H | H | O | H | OMe | OMe | CH | |
| I-759 | H | CO₂Me | 5-F | O | H | OMe | OMe | CH | |
| I-760 | H | CO₂Me | H | O | H | OCHF₂ | OCHF₂ | CH | |
| I-761 | H | CO₂Me | H | O | H | OMe | Me | CH | 202–205 |
| I-762 | H | CO₂Me | H | O | H | OMe | Me | N | 169–170 |
| I-763 | H | CO₂Me | H | O | H | OMe | OCHF₂ | CH | |
| I-764 | H | CO₂Me | H | O | Me | OMe | OMe | CH | |
| I-765 | H | CO₂Me | H | S | H | OMe | OMe | CH | |
| I-766 | H | CO₂Pen | H | O | H | OMe | OMe | CH | |
| I-767 | H | CO₂Ph | H | O | H | OMe | OMe | CH | |
| I-768 | H | CO₂Pr | H | O | H | OMe | Me | CH | |
| I-769 | H | CO₂Pr | H | O | H | OMe | OMe | CH | |
| I-770 | H | CO₂Pr-i | H | O | H | OMe | Me | CH | |
| I-771 | H | CO₂Pr-i | H | O | H | OMe | Me | N | |
| I-772 | H | CO₂Pr-i | H | O | H | OMe | OMe | CH | |
| I-773 | H | COBn | H | O | H | OMe | OMe | CH | |
| I-774 | H | COCH₂C≡CH | H | O | H | OMe | OMe | CH | |
| I-775 | H | COCH₂CH=CH₂ | H | O | H | OMe | OMe | CH | |
| I-776 | H | COEt | H | O | H | OMe | OMe | CH | |
| I-777 | H | COH | H | O | H | OMe | OMe | CH | |
| I-778 | H | COMe | H | O | H | OMe | OMe | CH | |
| I-779 | H | CON(Et)₂ | H | O | H | OMe | OMe | CH | |
| I-780 | H | CON(Me)₂ | H | O | H | OMe | OMe | CH | |
| I-781 | H | CONH₂ | H | O | H | OMe | OMe | CH | |
| I-782 | H | CONHBn | H | O | H | OMe | OMe | CH | |
| I-783 | H | CONHCH₂C≡CH | H | O | H | OMe | OMe | CH | |
| I-784 | H | CONHCH₂CH=CH₂ | H | O | H | OMe | OMe | CH | |
| I-785 | H | CONHEt | H | O | H | OMe | OMe | CH | |
| I-786 | H | CONHMe | H | O | H | OMe | OMe | CH | |
| I-787 | H | CONHOMe | H | O | H | OMe | OMe | CH | |
| I-788 | H | CONHPh | H | O | H | OMe | OMe | CH | |
| I-789 | H | CONHPr | H | O | H | OMe | OMe | CH | |
| I-790 | H | COOMe | H | O | H | OMe | Me | CH | |
| I-791 | H | COOMe | H | O | H | Me | OMe | N | |
| I-792 | H | COPh | H | O | H | OMe | OMe | CH | |
| I-793 | H | COPr | H | O | H | Me | OMe | CH | |
| I-794 | H | COPr | H | O | H | Me | OMe | N | |
| I-795 | H | COPr | H | O | H | OMe | OMe | CH | |
| I-796 | H | COPr-i | H | O | H | Me | OMe | CH | |
| I-797 | H | COPr-i | H | O | H | Me | OMe | N | |
| I-798 | H | COPr-i | H | O | H | OMe | OMe | CH | |

TABLE 1-continued

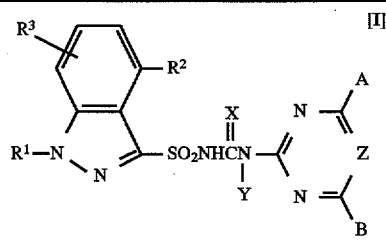

| Comp. NO. | R¹ | R² | R³ | X | Y | A | B | Z | Mp. (°C.) |
|---|---|---|---|---|---|---|---|---|---|
| I-799 | H | Cl | 5-Cl | O | H | OMe | OMe | CH | |
| I-800 | H | Cl | H | S | H | Cl | OMe | CH | |
| I-801 | H | Cl | H | O | H | Me | Me | CH | |
| I-802 | H | Cl | H | O | H | OMe | Me | CH | |
| I-803 | H | Cl | H | O | H | OMe | He | N | |
| I-804 | H | Cl | H | S | H | Me | Me | CH | |
| I-805 | H | Cl | H | S | H | OMe | Me | CH | |
| I-806 | H | Cl | H | S | H | OMe | Me | N | |
| I-807 | H | Cl | H | O | Me | OMe | OMe | CH | |
| I-808 | H | Cl | H | S | H | OMe | OMe | CH | |
| I-809 | H | Et | H | O | H | Me | OMe | CH | |
| I-810 | H | Et | H | O | H | Me | OMe | N | |
| I-811 | H | Et | H | O | H | OMe | OMe | CH | |
| I-812 | H | F | H | O | H | Me | Me | CH | |
| I-813 | H | F | H | O | H | OMe | Me | CH | |
| I-814 | H | F | H | O | H | OMe | Me | N | |
| I-815 | H | F | H | O | H | OMe | OMe | CH | |
| I-816 | H | H | 5-Cl | O | H | Me | Me | CH | |
| I-817 | H | H | 5-Cl | O | H | OMe | Me | N | |
| I-818 | H | H | 5-Cl | O | H | OMe | OMe | CH | |
| I-819 | H | H | 5-F | O | H | Me | Me | CH | |
| I-820 | H | H | 5-F | O | H | OMe | Me | CH | |
| I-821 | H | H | 5-F | O | H | OMe | Me | N | |
| I-822 | H | H | 5-F | O | H | OMe | OMe | CH | |
| I-823 | H | H | 5-OEt | O | H | OMe | Me | CH | |
| I-824 | H | H | 5-OEt | O | H | OMe | Me | N | |
| I-825 | H | H | 5-OEt | O | H | OMe | OMe | CH | |
| I-826 | H | H | 5-OEt | O | H | OMe | OMe | N | |
| I-827 | H | H | 5-OMe | O | H | Cl | OMe | CH | |
| I-828 | H | H | 5-OMe | O | H | OMe | Me | CH | |
| I-829 | H | H | 5-OMe | O | H | OMe | Me | N | |
| I-830 | H | H | 5-OMe | O | H | OMe | OMe | CH | |
| I-831 | H | H | 5-OPr | O | H | OMe | Me | CH | |
| I-832 | H | H | 5-OPr | O | H | OMe | Me | N | |
| I-833 | H | H | 5-OPr | O | H | OMe | OMe | CH | |
| I-834 | H | H | 5-OPr | O | H | OMe | OMe | N | |
| I-835 | H | H | 6-Cl | O | H | Me | Me | CH | |
| I-836 | H | H | 6-Cl | O | H | OMe | Me | N | |
| I-837 | H | H | 6-Cl | O | H | OMe | OMe | CH | |
| I-838 | H | H | 7-Cl | O | H | OMe | Me | N | |
| I-839 | H | H | 7-Cl | O | H | OMe | OMe | CH | |
| I-840 | H | H | H | O | H | Me | Me | CH | |
| I-841 | H | H | H | O | H | OMe | Me | N | |
| I-842 | H | H | H | O | H | OMe | OMe | CH | |
| I-843 | H | I | H | O | H | Me | OMe | CH | |
| I-844 | H | I | H | O | H | Me | OMe | N | |
| I-845 | H | I | H | O | H | OMe | OMe | CH | |
| I-846 | H | Me | H | O | H | OMe | OMe | CH | |
| I-847 | H | N(Et)SO₂Et | H | O | H | Me | OMe | CH | |
| I-848 | H | N(Et)SO₂Et | H | O | H | Me | OMe | N | |
| I-849 | H | N(Et)SO₂Et | H | O | H | OMe | OMe | CH | |
| I-850 | H | N(Et)SO₂Me | H | O | H | Me | OMe | CH | |
| I-851 | H | N(Et)SO₂Me | H | O | H | Me | OMe | N | |
| I-852 | H | N(Et)SO₂He | H | O | H | OMe | OMe | CH | |
| I-853 | H | N(Me)₂ | H | O | H | OMe | OMe | CH | |
| I-854 | H | N(Me)SO₂Et | H | O | H | Me | OMe | CH | |
| I-855 | H | N(Me)SO₂Et | H | O | H | Me | OMe | N | |
| I-856 | H | N(Me)SO₂Et | H | O | H | OMe | OMe | CH | |
| I-857 | H | N(Me)SO₂Me | H | O | H | Me | OMe | CH | |
| I-858 | H | N(Me)SO₂Me | H | O | H | Me | OMe | N | |
| I-859 | H | N(Me)SO₂Me | H | O | H | OMe | OMe | CH | |
| I-860 | H | N=CH—Ph | H | O | H | Me | OMe | CH | |
| I-861 | H | N=CH—Ph | H | O | H | Me | OMe | N | |
| I-862 | H | N=CH—Ph | H | O | H | OMe | OMe | CH | |
| I-863 | H | N=CHMe | H | O | H | Me | OMe | CH | |
| I-864 | H | N=CHME | H | O | H | He | OMe | N | |

TABLE 1-continued

| Comp. NO. | R¹ | R² | R³ | X | Y | A | B | Z | Mp. (°C.) |
|---|---|---|---|---|---|---|---|---|---|
| I-865 | H | N=CHMe | H | O | H | OMe | OMe | CH | |
| I-866 | H | N₃ | H | O | H | Me | OMe | CH | |
| I-867 | H | N₃ | H | O | H | Me | OMe | N | |
| I-868 | H | N₃ | H | O | H | OMe | OMe | CH | |
| I-869 | H | NEt₂ | H | O | H | OMe | OMe | CH | |
| I-870 | H | NH₂ | H | O | H | OMe | OMe | CH | |
| I-871 | H | NHBn | H | O | H | Cl | OMe | CH | |
| I-872 | H | NHBn | H | O | H | OMe | OMe | CH | |
| I-873 | H | NHCOCF₃ | H | O | H | Me | OMe | CH | |
| I-874 | H | NHCOCF₃ | H | O | H | Me | OMe | N | |
| I-875 | H | NHCOCF₃ | H | O | H | OMe | OMe | CH | |
| I-876 | H | NHCOCH₂Cl | H | O | H | OMe | OMe | CH | |
| I-877 | H | NHCOEt | H | O | H | Me | OMe | CH | |
| I-878 | H | NHCOEt | H | O | H | Me | OMe | N | |
| I-879 | H | NHCOEt | H | O | H | OMe | OMe | CH | |
| I-880 | H | NHCOMe | H | O | H | OMe | OMe | CH | |
| I-881 | H | NHCOOEt | H | O | H | Me | OMe | CH | |
| I-882 | H | NHCOOEt | H | O | H | Me | OMe | N | |
| I-883 | H | NHCOOEt | H | O | H | OMe | OMe | CH | |
| I-884 | H | NHCOOMe | H | O | H | Me | OMe | CH | |
| I-885 | H | NHCOOMe | H | O | H | Me | OMe | N | |
| I-886 | H | NHCOOMe | H | O | H | OMe | OMe | CH | |
| I-887 | H | NHCOOPh | H | O | H | Me | OMe | CH | |
| I-888 | H | NHCOOPh | H | O | H | Me | OMe | N | |
| I-889 | H | NHCOOPh | H | O | H | OMe | OMe | CH | |
| I-890 | H | NHCOPh | H | O | H | OMe | OMe | CH | |
| I-891 | H | NHEt | H | O | H | Me | OMe | CH | |
| I-892 | H | NHEt | H | O | H | Me | OMe | N | |
| I-893 | H | NHEt | H | O | H | OMe | OMe | CH | |
| I-894 | H | NHMe | H | O | H | OMe | Me | CH | |
| I-895 | H | NHMe | H | O | H | OMe | Me | N | |
| I-896 | H | NHMe | H | O | H | OMe | OMe | CH | |
| I-897 | H | NHPr | H | O | H | Me | OMe | CH | |
| I-898 | H | NHPr | H | O | H | Me | OMe | N | |
| I-899 | H | NHPr | H | O | H | OMe | OMe | CH | |
| I-900 | H | NHSO₂CH₃ | H | O | H | OMe | OMe | CH | |
| I-901 | H | NHSO₂Ph | H | O | H | OMe | OMe | CH | |
| I-902 | H | NMe₂ | H | O | H | Cl | OMe | CH | |
| I-903 | H | NMe₂ | H | O | H | Me | Me | CH | |
| I-904 | H | NMe₂ | H | O | H | OMe | Me | N | |
| I-905 | H | NO₂ | H | O | H | OMe | Me | CH | 208–210 |
| I-906 | H | NO₂ | H | O | H | OMe | OMe | CH | 184–186 |
| I-907 | H | OBn | H | O | H | OMe | OMe | CH | |
| I-908 | H | OBn(2-Me) | H | O | H | OMe | OMe | CH | |
| I-909 | H | OBn(3-OMe) | H | O | H | OMe | OMe | CH | |
| I-910 | H | OBn(4-Cl) | H | O | H | OMe | OMe | CH | |
| I-911 | H | OBu | H | O | H | Cl | OMe | CH | |
| I-912 | H | OBu | H | O | H | Me | Me | CH | |
| I-913 | H | OBu | H | O | H | OMe | Me | CH | |
| I-914 | H | OBu | H | O | H | OMe | Me | N | |
| I-915 | H | OBu | H | O | H | OMe | OMe | CH | |
| I-916 | H | OCF₂CH₂Cl | H | O | H | Me | OMe | CH | |
| I-917 | H | OCF₂CH₂Cl | H | O | H | Me | OMe | N | |
| I-918 | H | OCF₂CH₂Cl | H | O | H | OMe | OMe | CH | |
| I-919 | H | OCF₂CHFCl | H | O | H | Me | OMe | CH | |
| I-920 | H | OCF₂CHFCl | H | O | H | Me | OMe | N | |
| I-921 | H | OCF₂CHFCl | H | O | H | OMe | OMe | CH | |
| I-922 | H | OCF₃ | H | O | H | Me | OMe | CH | |
| I-923 | H | OCF₃ | H | O | H | Me | OMe | N | |
| I-924 | H | OCF₃ | H | O | H | OMe | OMe | CH | |
| I-925 | H | OCH(CF₂CF₃)Me | H | O | H | Me | OMe | CH | |
| I-926 | H | OCH(CF₂CF₃)Me | H | O | H | Me | OMe | N | |
| I-927 | H | OCH(CF₂CF₃)Me | H | O | H | OMe | OMe | CH | |
| I-928 | H | OCH(CF₃)Me | H | O | H | OMe | Me | CH | |
| I-929 | H | OCH(CF₃)Me | H | O | H | OMe | OMe | CH | |
| I-930 | H | OCH₂C(Cl)=CH₂ | H | O | H | Me | OMe | CH | |

TABLE 1-continued

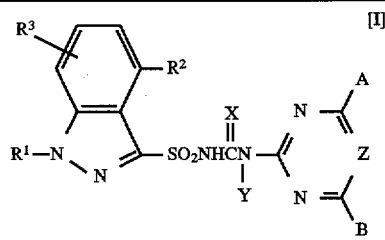

| Comp. NO. | R¹ | R² | R³ | X | Y | A | B | Z | Mp. (°C.) |
|---|---|---|---|---|---|---|---|---|---|
| I-931 | H | OCH₂C(Cl)=CH₂ | H | O | H | Me | OMe | N | |
| I-932 | H | OCH₂C(Cl)=CH₂ | H | O | H | OMe | OMe | CH | |
| I-933 | H | OCH₂C(Me)=CH₂ | H | O | H | Me | OMe | CH | |
| I-934 | H | OCH₂C(Me)=CH₂ | H | O | H | Me | OMe | N | |
| I-935 | H | OCH₂C(Me)=CH₂ | H | O | H | OMe | OMe | CH | |
| I-936 | H | OCH₂C≡CH | H | O | H | OMe | OMe | CH | |
| I-937 | H | OCH₂CF₂CF₃ | H | O | H | Me | OMe | CH | |
| I-938 | H | OCH₂CF₂CF₃ | H | O | H | Me | OMe | N | |
| I-939 | H | OCH₂CF₂CF₃ | H | O | H | OMe | OMe | CH | |
| I-940 | H | OCH₂CF₂CHF₂ | H | O | H | Me | OMe | CH | |
| I-941 | H | OCH₂CF₂CHF₂ | H | O | H | Me | OMe | N | |
| I-942 | H | OCH₂CF₂CHF₂ | H | O | H | OMe | OMe | CH | |
| I-943 | H | OCH₂CF₃ | H | O | H | Cl | OMe | CH | |
| I-944 | H | OCH₂CF₃ | H | O | H | OMe | Me | CH | |
| I-945 | H | OCH₂CF₃ | H | O | H | OMe | Me | N | |
| I-946 | H | OCH₂CF₃ | H | O | H | OMe | OMe | CH | |
| I-947 | H | OCH₂CH=CCl₂ | H | O | H | Me | OMe | CH | |
| I-948 | H | OCH₂CH=CCl₂ | H | O | H | Me | OMe | N | |
| I-949 | H | OCH₂CH=CCl₂ | H | O | H | OMe | OMe | CH | |
| I-950 | H | OCH₂CH=CH−Cl | H | O | H | Me | OMe | CH | |
| I-951 | H | OCH₂CH=CH−Cl | H | O | H | Me | OMe | N | |
| I-952 | H | OCH₂CH=CH−Cl | H | O | H | OMe | OMe | CH | |
| I-953 | H | OCH₂CH=CH₂ | H | O | H | OMe | OMe | H | |
| I-954 | H | OCH₂CH=CHMe | H | O | H | Me | OMe | CH | |
| I-955 | H | OCH₂CH=CHMe | H | O | H | Me | OMe | N | |
| I-956 | H | OCH₂CH=CHMe | H | O | H | OMe | OMe | CH | |
| I-957 | H | OCH₂CH₂CF₃ | H | O | H | Me | OMe | CH | |
| I-958 | H | OCH₂CH₂CF₃ | H | O | H | Me | OMe | N | |
| I-959 | H | OCH₂CH₂CF₃ | H | O | H | OMe | OMe | CH | |
| I-960 | H | OCH₂CH₂Cl | H | O | H | OMe | OMe | CH | |
| I-961 | H | OCH₂CH₂F | H | O | H | OMe | OMe | CH | |
| I-962 | H | OCH₂CH₂N₃ | H | O | H | Me | OMe | CH | |
| I-963 | H | OCH₂CH₂N₃ | H | O | H | He | OMe | N | |
| I-964 | H | OCH₂CH₂N₃ | H | O | H | OMe | OMe | CH | |
| I-965 | H | OCH₂CH₂NMe₂ | H | O | H | OMe | Me | CH | |
| I-966 | H | OCH₂CH₂NMe₂ | H | O | H | OMe | Me | N | |
| I-967 | H | OCH₂CH₂NMe₂ | H | O | H | OMe | OMe | CH | |
| I-968 | H | OCH₂CH₂OBu | H | O | H | OMe | Me | CH | |
| I-969 | H | OCH₂CH₂OBu | H | O | H | OMe | Me | N | |
| I-970 | H | OCH₂CH₂OBu | H | O | H | OMe | OMe | CH | |
| I-971 | H | OCH₂CH₂OBu | H | O | H | OMe | OMe | N | |
| I-972 | H | OCH₂CH₂OBu-t | H | O | H | OMe | Me | CH | |
| I-973 | H | OCH₂CH₂OBu-t | H | O | H | OMe | Me | N | |
| I-974 | H | OCH₂CH₂OBu-t | H | O | H | OMe | OMe | CH | |
| I-975 | H | OCH₂CH₂OBu-t | H | O | H | OMe | OMe | N | |
| I-976 | H | OCH₂CH₂OEt | H | O | H | OMe | Me | CH | |
| I-977 | H | OCH₂CH₂OEt | H | O | H | OMe | Me | N | |
| I-978 | H | OCH₂CH₂OEt | H | O | H | OMe | OMe | CH | |
| I-979 | H | OCH₂CH₂OMe | H | O | H | OMe | Me | CH | |
| I-980 | H | OCH₂CH₂OMe | H | O | H | OMe | OMe | CH | |
| I-981 | H | OCH₂CH₂OPh | H | O | H | OMe | OMe | CH | |
| I-982 | H | OCH₂CH₂OPr-i | H | O | H | OMe | Me | CH | |
| I-983 | H | OCH₂CH₂OPr-i | H | O | H | OMe | Me | N | |
| I-984 | H | OCH₂CH₂OPr-i | H | O | H | OMe | OMe | CH | |
| I-985 | H | OCH₂CH₂SMe | H | O | H | Me | OMe | CH | |
| I-986 | H | OCH₂CH₂SMe | H | O | H | Me | OMe | N | |
| I-987 | H | OCH₂CH₂SMe | H | O | H | OMe | OMe | CH | |
| I-988 | H | OCH₂CHCl₂ | H | O | H | Me | OMe | CH | |
| I-989 | H | OCH₂CHCl₂ | H | O | H | Me | OMe | N | |
| I-990 | H | OCH₂CHCl₂ | H | O | H | OMe | OMe | CH | |
| I-991 | H | OCH₂CHF₂ | H | O | H | Me | OMe | CH | |
| I-992 | H | OCH₂CHF₂ | H | O | H | Me | OMe | N | |
| I-993 | H | OCH₂CHF₂ | H | O | H | OMe | OMe | CH | |
| I-994 | H | OCH₂CN | H | O | H | Me | OMe | CH | |
| I-995 | H | OCH₂CN | H | O | H | Me | OMe | N | |

TABLE 1-continued

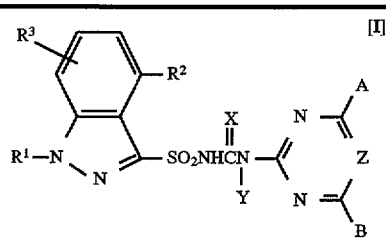

| Comp. NO. | R¹ | R² | R³ | X | Y | A | B | Z | Mp. (°C.) |
|---|---|---|---|---|---|---|---|---|---|
| I-996 | H | OCH$_2$CN | H | O | H | OMe | OMe | CH | |
| I-997 | H | OCH$_2$COOEt | H | O | H | OMe | OMe | CH | |
| I-998 | H | OCH$_2$COOMe | H | O | H | Me | OMe | CH | |
| I-999 | H | OCH$_2$COOMe | H | O | H | Me | OMe | N | |
| I-1000 | H | OCH$_2$COOMe | H | O | H | OMe | OMe | CH | |
| I-1001 | H | OCH$_2$COOPr | H | O | H | Me | OMe | CH | |
| I-1002 | H | OCH$_2$COOPr | H | O | H | Me | OMe | N | |
| I-1003 | H | OCH$_2$COOPr | H | O | H | OMe | OMe | CH | |
| I-1004 | H | OCH$_2$COOPr-i | H | O | H | Me | OMe | CH | |
| I-1005 | H | OCH$_2$COOPr-i | H | O | H | Me | OMe | N | |
| I-1006 | H | OCH$_2$COOPr-i | H | O | H | OMe | OMe | CH | |
| I-1007 | H | OCH$_2$OBn | H | O | H | Me | OMe | CH | |
| I-1008 | H | OCH$_2$OBn | H | O | H | Me | OMe | N | |
| I-1009 | H | OCH$_2$OBn | H | O | H | OMe | OMe | CH | |
| I-1010 | H | OCH$_2$OBu-t | H | O | H | Me | OMe | CH | |
| I-1011 | H | OCH$_2$OBu-t | H | O | H | Me | OMe | N | |
| I-1012 | H | OCH$_2$OBu-t | H | O | H | OMe | OMe | CH | |
| I-1013 | H | OCH$_2$OCH$_2$CF$_3$ | H | O | H | Me | OMe | CH | |
| I-1014 | H | OCH$_2$OCH$_2$CF$_3$ | H | O | H | Me | OMe | N | |
| I-1015 | H | OCH$_2$OCH$_2$CF$_3$ | H | O | H | OMe | OMe | CH | |
| I-1016 | H | OCH$_2$OCH$_2$CH$_2$OMe | H | O | H | Me | OMe | CH | |
| I-1017 | H | OCH$_2$OCH$_2$CH$_2$OMe | H | O | H | Me | OMe | N | |
| I-1018 | H | OCH$_2$OCH$_2$CH$_2$OMe | H | O | H | OMe | OMe | CH | |
| I-1019 | H | OCH$_2$OEt | H | O | H | Me | OMe | CH | |
| I-1020 | H | OCH$_2$OEt | H | O | H | Me | OMe | N | |
| I-1021 | H | OCH$_2$OEt | H | O | H | OMe | OMe | CH | |
| I-1022 | H | OCH$_2$OMe | H | O | H | Me | OMe | CH | |
| I-1023 | H | OCH$_2$OMe | H | O | H | Me | OMe | N | |
| I-1024 | H | OCH$_2$OMe | H | O | H | OMe | OMe | CH | |
| I-1025 | H | OCH$_2$SMe | H | O | H | Me | OMe | CH | |
| I-1026 | H | OCH$_2$SMe | H | O | H | Me | OMe | N | |
| I-1027 | H | OCH$_2$SMe | H | O | H | OMe | OMe | CH | |
| I-1028 | H | OCHF$_2$ | H | O | H | Me | OMe | CH | |
| I-1029 | H | OCHF$_2$ | H | O | H | Me | OMe | N | |
| I-1030 | H | OCHF$_2$ | H | O | H | OMe | OMe | CH | |
| I-1031 | H | OCOEt | H | O | H | Me | OMe | CH | |
| I-1032 | H | OCOEt | H | O | H | Me | OMe | N | |
| I-1033 | H | OCOEt | H | O | H | OMe | OMe | CH | |
| I-1034 | H | OCOMe | H | O | H | OMe | OMe | CH | |
| I-1035 | H | OCONMe$_2$ | H | O | H | Me | OMe | CH | |
| I-1036 | H | OCONMe$_2$ | H | O | H | Me | OMe | N | |
| I-1037 | H | OCONMe$_2$ | H | O | H | OMe | OMe | CH | |
| I-1038 | H | OCOPh | H | O | H | Me | OMe | CH | |
| I-1039 | H | OCOPh | H | O | H | Me | OMe | N | |
| I-1040 | H | OCOPh | H | O | H | OMe | OMe | CH | |
| I-1041 | H | OCOPr | H | O | H | Me | OMe | CH | |
| I-1042 | H | OCOPr | H | O | H | Me | OMe | N | |
| I-1043 | H | OCOPr | H | O | H | OMe | OMe | CH | |
| I-1044 | H | OEt | H | O | H | Me | Me | CH | |
| I-1045 | H | OEt | H | O | H | OMe | Me | CH | |
| I-1046 | H | OEt | H | O | H | OMe | Me | N | |
| I-1047 | H | OEt | H | O | H | OMe | OMe | CH | |
| I-1048 | H | OH | H | O | H | OMe | OMe | CH | |
| I-1049 | H | OMe | 5-Cl | O | H | OMe | Me | N | |
| I-1050 | H | OMe | 5-Cl | O | H | OMe | OMe | CH | |
| I-1051 | H | OMe | 5-OMe | O | H | OMe | Me | CH | |
| I-1052 | H | OMe | H | O | H | Cl | OMe | CH | |
| I-1053 | H | OMe | H | O | H | OMe | Me | CH | |
| I-1054 | H | OMe | H | O | H | OMe | OMe | N | |
| I-1055 | H | OMe | H | O | H | Me | Me | CH | |
| I-1056 | H | OMe | H | O | H | OMe | Me | N | |
| I-1057 | H | OMe | H | O | H | OMe | OMe | CH | |
| I-1058 | H | OPh | H | O | H | OMe | OMe | CH | |
| I-1059 | H | OPh(2-Me) | H | O | H | OMe | OMe | CH | |
| I-1060 | H | OPh(3-OMe) | H | O | H | OMe | OMe | CH | |
| I-1061 | H | OPh(4-Cl) | H | O | H | OMe | OMe | CH | |

TABLE 1-continued

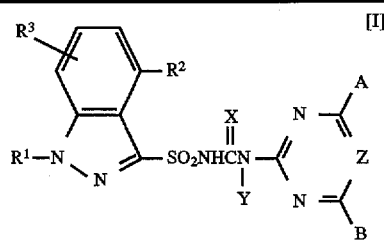

| Comp. NO. | R¹ | R² | R³ | X | Y | A | B | Z | Mp. (°C.) |
|---|---|---|---|---|---|---|---|---|---|
| I-1062 | H | OPr | H | O | H | Cl | OMe | CH | |
| I-1063 | H | OPr | H | O | H | Me | Me | CH | |
| I-1064 | H | OPr | H | O | H | OMe | Me | CH | |
| I-1065 | H | OPr | H | O | H | OMe | Me | N | |
| I-1066 | H | OPr | H | O | H | OMe | OMe | CH | |
| I-1067 | H | OPr-i | H | O | H | Me | Me | CH | |
| I-1068 | H | OPr-i | H | O | H | OMe | Me | CH | |
| I-1069 | H | OPr-i | H | O | H | OMe | Me | N | |
| I-1070 | H | OPr-i | H | O | H | OMe | OMe | CH | |
| I-1071 | H | Ph | H | O | H | OMe | OMe | CH | |
| I-1072 | H | Pr | H | O | H | Me | OMe | CH | |
| I-1073 | H | Pr | H | O | H | Me | OMe | N | |
| I-1074 | H | Pr | H | O | H | OMe | OMe | CH | |
| I-1075 | H | Pr-i | H | O | H | Me | OMe | CH | |
| I-1076 | H | Pr-i | H | O | H | Me | OMe | N | |
| I-1077 | H | Pr-i | H | O | H | OMe | OMe | CH | |
| I-1078 | H | SBu | H | O | H | Cl | OMe | CH | |
| I-1079 | H | SBu | H | O | H | OMe | OMe | CH | |
| I-1080 | H | SCF₃ | H | O | H | Me | OMe | CH | |
| I-1081 | H | SCF₃ | H | O | H | Me | OMe | N | |
| I-1082 | H | SCF₃ | H | O | H | OMe | OMe | CH | |
| I-1083 | H | SCH₂CH₂Cl | H | O | H | Me | OMe | CH | |
| I-1084 | H | SCH₂CH₂Cl | H | O | H | Me | OMe | N | |
| I-1085 | H | SCH₂CH₂Cl | H | O | H | OMe | OMe | CH | |
| I-1086 | H | SCH₂CH₂F | H | O | H | Me | OMe | CH | |
| I-1087 | H | SCH₂CH₂F | H | O | H | Me | OMe | N | |
| I-1088 | H | SCH₂CH₂F | H | O | H | OMe | OMe | CH | |
| I-1089 | H | SEt | H | O | H | OMe | Me | N | |
| I-1090 | H | SEt | H | O | H | OMe | OMe | CH | |
| I-1091 | H | SH | H | O | H | OMe | OMe | CH | |
| I-1092 | H | SMe | H | O | H | OMe | OMe | CH | |
| I-1093 | H | SO₂Bu | H | O | H | OMe | OMe | CH | |
| I-1094 | H | SO₂CH₂CH=CH₂ | H | O | H | Me | OMe | CH | |
| I-1095 | H | SO₂CH₂CH=CH₂ | H | O | H | Me | OMe | N | |
| I-1096 | H | SO₂CH₂CH=CH₂ | H | O | H | OMe | OMe | CH | |
| I-1097 | H | SO₂Et | H | O | H | OMe | OMe | CH | |
| I-1098 | H | SO₂Me | H | O | H | OMe | OMe | CH | |
| I-1099 | H | SO₂NMe₂ | H | O | H | OMe | OMe | CH | |
| I-1100 | H | SO₂NEt₂ | H | O | H | Me | OMe | CH | |
| I-1101 | H | SO₂NEt₂ | H | O | H | Me | OMe | N | |
| I-1102 | H | SO₂NEt₂ | H | O | H | OMe | OMe | CH | |
| I-1103 | H | SO₂NH₂ | H | O | H | OMe | OMe | CH | |
| I-1104 | H | SO₂NHBn | H | O | H | OMe | OMe | CH | |
| I-1105 | H | SO₂NHCH₂C≡CH | H | O | H | OMe | OMe | CH | |
| I-1106 | H | SO₂NHCH₂CH=CH₂ | H | O | H | OMe | OMe | CH | |
| I-1107 | H | SO₂NHMe | H | O | H | OMe | OMe | CH | |
| I-1108 | H | SO₂NHOEt | H | O | H | Me | OMe | CH | |
| I-1109 | H | SO₂NHOEt | H | O | H | Me | OMe | N | |
| I-1110 | H | SO₂NHOEt | H | O | H | OMe | OMe | CH | |
| I-1111 | H | SO₂NHOMe | H | O | H | OMe | OMe | CH | |
| I-1112 | H | SO₂NHPh | H | O | H | OMe | OMe | CH | |
| I-1113 | H | SO₂Pr | H | O | H | OMe | OMe | CH | |
| I-1114 | H | SO₂Pr-i | H | O | H | Cl | OMe | CH | |
| I-1115 | H | SO₂Pr-i | H | O | H | OMe | OMe | CH | |
| I-1116 | H | SOEt | H | O | H | Me | OMe | CH | |
| I-1117 | H | SOEt | H | O | H | Me | OMe | N | |
| I-1118 | H | SOEt | H | O | H | OMe | OMe | CH | |
| I-1119 | H | SOMe | H | O | H | OMe | OMe | CH | |
| I-1120 | H | SPr | H | O | H | Cl | OMe | CH | |
| I-1121 | H | SPr | H | O | H | OMe | Me | CH | |
| I-1122 | H | SPr | H | O | H | OMe | Me | N | |
| I-1123 | H | SPr | H | O | H | OMe | OMe | CH | |
| I-1124 | H | SPr-i | H | O | H | Cl | OMe | CH | |
| I-1125 | H | SPr-i | H | O | H | OMe | OMe | CH | |
| I-1126 | H | NO₂ | H | O | H | Me | OMe | N | 182–184 |

TABLE 1-continued

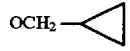

| Comp. NO. | R¹ | R² | R³ | X | Y | A | B | Z | Mp. (°C.) |
|---|---|---|---|---|---|---|---|---|---|
| I-1127 | H | SEt | H | O | H | Cl | OMe | CH | |
| I-1128 | H | SEt | H | O | H | Me | Me | CH | |
| I-1129 | H | SBu | H | O | H | OMe | OMe | N | |
| I-1130 | H | SBu | H | O | H | OMe | Me | CH | |
| I-1131 | H | SBu | H | O | H | OMe | Me | N | |
| I-1132 | H | SPr-i | H | O | H | OMe | Me | CH | |
| I-1133 | H | SPr-i | H | O | H | OMe | Me | N | |
| I-1134 | H | SOEt | H | O | H | OMe | OMe | N | |
| I-1135 | H | SO₂Et | H | O | H | OMe | Me | CH | |
| I-1136 | H | SO₂Et | H | O | H | OMe | Me | N | |
| I-1137 | H | SO₂Et | H | O | H | OMe | Cl | CH | |
| I-1138 | H | SO₂Pr | H | O | H | OMe | Me | CH | |
| I-1139 | H | SO₂Pr | H | O | H | OMe | Me | N | |
| I-1140 | H | SO₂Pr | H | O | H | OMe | Cl | CH | |
| I-1141 | H | SO₂Bu | H | O | H | OMe | Me | CH | |
| I-1142 | H | SO₂Bu | H | O | H | OMe | Me | N | |
| I-1143 | H | SO₂Bu | H | O | H | OMe | Cl | CH | |
| I-1144 | H | SO₂Pr-i | H | O | H | OMe | Me | CH | |
| I-1145 | H | SO₂Pr-i | H | O | H | OMe | Me | N | |
| I-1146 | H | COOPr | H | O | H | OMe | Me | N | |
| I-1147 | H | NO₂ | H | O | H | OMe | Cl | CH | |
| I-1148 | H | CONMe₂ | H | O | H | OMe | Me | CH | |
| I-1149 | H | Br | H | O | H | OMe | Cl | CH | |
| I-1150 | H | OCH₂—△ | H | O | H | OMe | OMe | CH | |
| I-1151 | H | OCH₂—Bu-t | H | O | H | OMe | OMe | CH | |
| I-1152 | H | OCH₂—Bu-t | H | O | H | Me | OMe | CH | |
| I-1153 | H | OCH₂CH=CMe₂ | H | O | H | OMe | OMe | CH | |
| I-1154 | H | OCH₂CH₂CH₂F | H | O | H | OMe | OMe | CH | |
| I-1155 | H | OCH₂CH₂CH₂F | H | O | H | Me | OMe | CH | |
| I-1156 | H | OCH₂CH₂CH₂F | H | O | H | Me | OMe | N | |
| I-1157 | H | CH₂CH₂N₃ | H | O | H | OMe | OMe | CH | |
| I-1158 | H | CH₂CO—△ | H | O | H | OMe | OMe | CH | |
| I-1159 | H | COCF₃ | H | O | H | OMe | OMe | CH | |
| I-1160 | H | COOCH₂CH=CHCl | H | O | H | OMe | OMe | CH | |
| I-1161 | H | SO₂CF₃ | H | O | H | OMe | OMe | CH | |
| I-1162 | H | OCOCF₃ | H | O | H | OMe | OMe | CH | |
| I-1163 | H | OCH₂OPh | H | O | H | OMe | OMe | CH | |
| I-1164 | H | CH=NOH | H | O | H | OMe | OMe | CH | |
| I-1165 | H | CH=NOCH₂CH=CH₂ | H | O | H | OMe | OMe | CH | |
| I-1166 | H | CH=NOCH₂C≡CH | H | O | H | OMe | OMe | CH | |
| I-1167 | H | C(Me)=NOBn | H | O | H | OMe | OMe | CH | |
| I-1168 | H | C(Me)=NOPh | H | O | H | OMe | OMe | CH | |
| I-1169 | H | C(Bn)=NOMe | H | O | H | OMe | OMe | CH | |
| I-1170 | H | C(Ph)=NOMe | H | O | H | OMe | OMe | CH | |
| I-1171 | H | C(CF₃)=NOMe | H | O | H | OMe | OMe | CH | |
| I-1172 | H | COOCH₂CH₂Cl | H | O | H | OMe | OMe | CH | |
| I-1173 | H | COOCH₂CF₃ | H | O | H | OMe | OMe | CH | |
| I-1174 | H | Cl | 5-Cl | O | H | OMe | Me | N | |
| I-1175 | H | Cl | 5-OMe | O | H | OMe | OMe | CH | |
| I-1176 | H | Cl | 5-F | O | H | OMe | OMe | CH | |
| I-1177 | H | F | 5-Cl | O | H | OMe | OMe | CH | |
| I-1178 | H | F | 5-F | O | H | OMe | OMe | CH | |
| I-1179 | H | COOMe | 5-Cl | O | H | OMe | OMe | CH | |
| I-1180 | H | COOEt | 5-Cl | O | H | OMe | OMe | CH | |
| I-1181 | H | COOPr | 5-Cl | O | H | OMe | OMe | CH | |
| I-1182 | H | COOPr-i | 5-Cl | O | H | OMe | OMe | CH | |
| I-1183 | H | OMe | 5-COOMe | O | H | OMe | OMe | CH | |
| I-1184 | H | COOMe | 5-OMe | O | H | OMe | OMe | CH | |

TABLE 1-continued

| Comp. NO. | R¹ | R² | R³ | X | Y | A | B | Z | Mp. (°C.) |
|---|---|---|---|---|---|---|---|---|---|
| I-1185 | H | ON=CHMe | H | O | H | OMe | OMe | CH | |
| I-1186 | H | ON=CMe₂ | H | O | H | OMe | OMe | CH | |
| I-1187 | H | ON=CHBn | H | O | H | OMe | OMe | CH | |
| I-1188 | H | OCH₂CH₂F | H | O | H | OMe | Me | CH | |
| I-1189 | H | OCH₂CH₂F | H | O | H | OMe | Me | N | |
| I-1190 | H | H | 5-CN | O | H | OMe | OMe | CH | |
| I-1191 | H | H | 5-CF₃ | O | H | OMe | OMe | CH | |
| I-1192 | H | H | 5-COOMe | O | H | OMe | OMe | CH | |
| I-1193 | H | H | 5-COOEt | O | H | OMe | OMe | CH | |
| I-1194 | H | H | 5-COOPr | O | H | OMe | OMe | CH | |
| I-1195 | H | H | 5-COOPr-i | O | H | OMe | OMe | CH | |
| I-1196 | H | H | 5-COOCH₂CH₂Cl | O | H | OMe | OMe | CH | |
| I-1197 | H | H | 5-COOCH₂CH₂F | O | H | OMe | OMe | CH | |
| I-1198 | H | H | 5-COOCH₂CF₃ | O | H | OMe | OMe | CH | |
| I-1199 | H | H | 5-COOCH₂OMe | O | H | OMe | OMe | CH | |
| I-1200 | H | H | 5-CONMe₂ | O | H | OMe | OMe | CH | |
| I-1201 | H | H | 5-OCH₂CH₂F | O | H | OMe | OMe | CH | |
| I-1202 | H | H | 5-OCHF₂ | O | H | OMe | OMe | CH | |
| I-1203 | H | H | 5-OCH₂CF₃ | O | H | OMe | OMe | CH | |
| I-1204 | H | H | 5-OCH₂CH₂CH₂F | O | H | OMe | OMe | CH | |
| I-1205 | H | H | 5-OCH₂CH=CH₂ | O | H | OMe | OMe | CH | |
| I-1206 | H | H | 5-OCH₂C≡CH | O | H | OMe | OMe | CH | |
| I-1207 | H | H | 5-NO₂ | O | H | OMe | OMe | CH | |
| I-1208 | H | H | 5-SMe | O | H | OMe | OMe | CH | |
| I-1209 | H | H | 5-SEt | O | H | OMe | OMe | CH | |
| I-1210 | H | H | 5-SPr | O | H | OMe | OMe | CH | |
| I-1211 | H | H | 5-SPr-i | O | H | OMe | OMe | CH | |
| I-1212 | H | H | 5-SO₂Et | O | H | OMe | OMe | CH | |
| I-1213 | H | H | 5-SO₂Pr | O | H | OMe | OMe | CH | |
| I-1214 | H | H | 5-SO₂Pr-i | O | H | OMe | OMe | CH | |
| I-1215 | H | H | 5-SOEt | O | H | OMe | OMe | CH | |
| I-1216 | H | H | 5-Me | O | H | OMe | OMe | CH | |
| I-1217 | H | H | 5-Et | O | H | OMe | OMe | CH | |
| I-1218 | H | H | 5-Pr | O | H | OMe | OMe | CH | |
| I-1219 | H | H | 5-SO₂NMe₂ | O | H | OMe | OMe | CH | |
| I-1220 | H | H | 5-OCF₃ | O | H | OMe | OMe | CH | |
| I-1221 | H | H | 5-CH₂CF₃ | O | H | OMe | OMe | CH | |
| I-1222 | H | H | 5-CH₂CH=CH₂ | O | H | OMe | OMe | CH | |
| I-1223 | H | H | 5-COOMe | O | H | OMe | Me | CH | |
| I-1224 | H | H | 5-COOMe | O | H | OMe | Me | N | |
| I-1225 | H | H | 5-COOMe | O | H | OMe | OMe | N | |
| I-1226 | H | Cl | H | O | CH₃OCH₂ | OMe | OMe | CH | |
| I-1227 | H | Cl | H | O | H | OMe | NMe₂ | N | |
| I-1228 | H | Cl | H | O | H | OMe | NHMe | N | |
| I-1229 | H |  | H | O | H | Me | OMe | CH | |
| I-1230 | H |  | H | O | H | Me | OMe | N | |
| I-1231 | H | 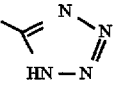 | H | O | H | OMe | OMe | CH | |
| I-1232 | H | 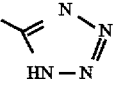 | H | O | H | OMe | OMe | CH | |
| I-1233 | H | 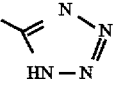 | H | O | H | Me | OMe | CH | |

TABLE 1-continued

[Structure [I]: pyrazole with R¹-N, fused benzene ring with R², R³, connected via SO₂NHC(=X)N(Y)- to a pyrimidine/triazine ring with A, B, Z]

| Comp. NO. | R¹ | R² | R³ | X | Y | A | B | Z | Mp. (°C.) |
|---|---|---|---|---|---|---|---|---|---|
| I-1234 | H | [triazole with HN-N, Me] | H | O | H | Me | OMe | N | |
| I-1235 | H | [triazole with Me-N-N] | H | O | H | OMe | OMe | CH | |
| I-1236 | H | [triazole with Me-N-N] | H | O | H | Me | OMe | CH | |
| I-1237 | H | [triazole with Me-N-N] | H | O | H | Me | OMe | N | |
| I-1238 | H | [triazole N-Me, N=N] | H | O | H | OMe | OMe | CH | |
| I-1239 | H | [triazole N-Me, N=N] | H | O | H | Me | OMe | CH | |
| I-1240 | H | [triazole N-Me, N=N] | H | O | H | Me | OMe | N | |
| I-1241 | H | —O—C₂H₄—O—* | | O | H | OMe | OMe | CH | |
| I-1242 | H | —O—C₂H₄—O—* | | O | H | Me | OMe | CH | |
| I-1243 | H | —O—C₂H₄—O—* | | O | H | Me | OMe | N | |
| I-1244 | H | —S—C₂H₄—S—* | | O | H | OMe | OMe | CH | |
| I-1245 | H | —S—C₂H₄—S—* | | O | H | Me | OMe | CH | |
| I-1246 | H | —S—C₂H₄—S—* | | O | H | Me | OMe | N | |
| I-1247 | H | —O—CH₂—O—* | | O | H | OMe | OMe | CH | |
| I-1248 | Me | Cl | H | O | CH₃OCH₂ | OMe | OMe | CH | |
| I-1249 | Me | Cl | H | O | H | OMe | NMe₂ | N | |
| I-1250 | Me | Cl | H | O | H | OMe | NHMe | N | |
| I-1251 | Me | ON=CHMe | H | O | H | OMe | OMe | CH | |
| I-1252 | Me | ON=CMe₂ | H | O | H | OMe | OMe | CH | |
| I-1253 | Me | ON=CHBn | H | O | H | OMe | OMe | CH | |
| I-1254 | Me | OCH₂CH₂F | H | O | H | OMe | Me | CH | |
| I-1255 | Me | OCH₂CH₂F | H | O | H | OMe | Me | N | |
| I-1256 | Me | F | H | O | H | NMe₂ | OCH₂CF₃ | N | 128–130 |
| I-1257 | Me | CO₂CH₂CH₂Cl | H | O | H | OMe | OMe | CH | |
| I-1258 | Me | CO₂CH₂CF₃ | H | O | H | OMe | OMe | CH | |
| I-1259 | Me | CO₂CH₂OMe | H | O | H | OMe | OMe | CH | |
| I-1260 | H | CO₂CH₂CH₂Cl | H | O | H | OMe | OMe | CH | |
| I-1261 | H | CO₂CH₂CF₃ | H | O | H | OMe | OMe | CH | |
| I-1262 | H | CO₂CH₂OMe | H | O | H | OMe | OMe | CH | |
| I-1263 | Et | CO₂Me | H | O | H | OMe | Me | CH | 198–200 |
| I-1264 | Et | CO₂Me | H | O | H | OMe | Me | N | 153–155 |
| I-1265 | Me | SO₂NMe₂ | H | O | H | OMe | Me | CH | 134–135 |
| I-1266 | Me | SO₂NMe₂ | H | O | H | OMe | Me | N | 253–255 |

TABLE 2

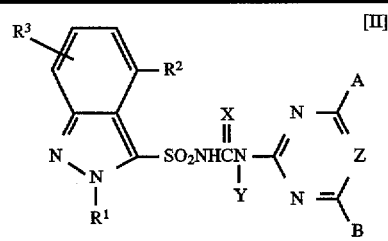

| Comp. No. | R¹ | R² | R³ | X | Y | A | B | Z | mp. (°C.) |
|---|---|---|---|---|---|---|---|---|---|
| II-1 | Me | Ph | H | O | H | OMe | OMe | CH | |
| II-2 | Me | Bn | H | O | H | OMe | OMe | CH | |
| II-3 | Me | SH | H | O | H | OMe | OMe | CH | |
| II-4 | Me | SMe | H | O | H | OMe | OMe | CH | |
| II-5 | Me | SEt | H | O | H | OMe | OMe | CH | 156–157 |
| II-6 | Me | SPr | H | O | H | OMe | OMe | CH | 143–145 |
| II-7 | Me | SO₂Me | H | O | H | OMe | OMe | CH | |
| II-8 | Me | SO₂Et | H | O | H | OMe | OMe | CH | 196–198 |
| II-9 | Me | SOMe | H | O | H | OMe | OMe | CH | |
| II-10 | Me | SO₂NHMe | H | O | H | OMe | OMe | CH | |
| II-11 | Me | SO₂NHOMe | H | O | H | OMe | OMe | CH | |
| II-12 | Me | SO₂NMe₂ | H | O | H | OMe | OMe | CH | 169–171 |
| II-13 | Me | SO₂NHBn | H | O | H | OMe | OMe | CH | |
| II-14 | Me | SO₂NHPh | H | O | H | OMe | OMe | CH | |
| II-15 | Me | SO₂NHCH₂CH=CH₂ | H | O | H | OMe | OMe | CH | |
| II-16 | Me | SO₂NHCH₂C≡CH | H | O | H | OMe | OMe | CH | |
| II-17 | H | Cl | H | O | H | OMe | OMe | CH | 191–193 |
| II-18 | Me | Cl | H | O | H | Me | Me | CH | 210–213 |
| II-19 | Me | Cl | 5-Cl | O | H | OMe | OMe | CH | 203–205 |
| II-20 | Et | Cl | H | O | H | OMe | OMe | CH | 174–175 |
| II-21 | Ph | Cl | H | O | H | OMe | OMe | CH | 221–223 |
| II-22 | Bn | Cl | H | O | H | OMe | OMe | CH | |
| II-23 | Me | H | H | O | H | OMe | OMe | CH | 199–202 |
| II-24 | Me | H | H | O | H | Me | Me | CH | 208–210 |
| II-25 | Me | H | H | O | H | OMe | Me | N | 172–174 |
| II-26 | Me | F | H | O | H | OMe | OMe | CH | 205–206 |
| II-27 | Me | Br | H | O | H | OMe | OMe | CH | 179–182 |
| II-28 | Me | Me | H | O | H | OMe | OMe | CH | 178–180 |
| II-29 | Me | CN | H | O | H | OMe | OMe | CH | 189–191 |
| II-30 | Me | CF₃ | H | O | H | OMe | OMe | CH | |
| II-31 | Me | Cl | H | O | H | OMe | Me | CH | 202–204 |
| II-32 | Me | Cl | H | O | H | OMe | Me | N | 170–172 |
| II-33 | Me | F | H | O | H | Me | Me | CH | 207–209 |
| II-34 | Me | F | H | O | H | OMe | Me | N | 178–180 |
| II-35 | Me | F | H | O | H | OMe | Me | CH | 185–187 |
| II-36 | Me | H | 5-Cl | O | H | OMe | OMe | CH | 215–216 |
| II-37 | Me | H | 5-Cl | O | H | Me | Me | CH | 192–194 |
| II-38 | Me | H | 5-Cl | O | H | OMe | Me | N | 176–178 |
| II-39 | Me | H | 6-Cl | O | H | OMe | OMe | CH | 210–212 |
| II-40 | Me | H | 6-Cl | O | H | Me | Me | CH | 217–220 |
| II-41 | Me | H | 6-Cl | O | H | OMe | Me | N | 181–183 |
| II-42 | Me | H | 7-Cl | O | H | OMe | OMe | CH | 223–225 |
| II-43 | Me | H | 7-Cl | O | H | OMe | Me | N | 167–169 |
| II-44 | Me | Cl | H | S | H | OMe | OMe | CH | |
| II-45 | Me | Cl | H | O | Me | OMe | OMe | CH | |
| II-46 | Me | COH | H | O | H | OMe | OMe | CH | |
| II-47 | Me | COMe | H | O | H | OMe | OMe | CH | |
| II-48 | Me | COEt | H | O | H | OMe | OMe | CH | |
| II-49 | Me | COPh | H | O | H | OMe | OMe | CH | |
| II-50 | Me | COCH₂CH=CH₂ | H | O | H | OMe | OMe | CH | |
| II-51 | Me | COCH₂C≡CH | H | O | H | OMe | OMe | CH | |
| II-52 | Me | COBn | H | O | H | OMe | OMe | CH | |
| II-53 | Me | NO₂ | H | O | H | OMe | OMe | CH | 155–157 |
| II-54 | Me | NH₂ | H | O | H | OMe | OMe | CH | 143–144 |
| II-55 | Me | NHMe | H | O | H | OMe | OMe | CH | |
| II-56 | Me | NMe₂ | H | O | H | OMe | OMe | CH | 183–185 |
| II-57 | Me | NHCOMe | H | O | H | OMe | OMe | CH | |
| II-58 | Me | NHCOPh | H | O | H | OMe | OMe | CH | |
| II-59 | Me | NHCOCH₂Cl | H | O | H | OMe | OMe | CH | |
| II-60 | Me | NHSO₂CH₃ | H | O | H | OMe | OMe | CH | |
| II-61 | Me | NHSO₂Ph | H | O | H | OMe | OMe | CH | |
| II-62 | Me | CO₂H | H | O | H | OMe | OMe | CH | |
| II-63 | Me | CO₂Me | H | O | H | OMe | OMe | CH | 179–181 |
| II-64 | Me | CO₂Et | H | O | H | OMe | OMe | CH | 181–182 |

TABLE 2-continued

[Structure II: pyrazole with R³ and R² substituents on fused benzene ring, -SO₂NHC(=X)N(Y)- linked to pyrimidine/triazine bearing A, B, and Z; R¹ on pyrazole N]

| Comp. No. | R¹ | R² | R³ | X | Y | A | B | Z | mp. (°C.) |
|---|---|---|---|---|---|---|---|---|---|
| II-65 | Me | CO₂Pr | H | O | H | OMe | OMe | CH | 188–190 |
| II-66 | Me | CO₂Pr-i | H | O | H | OMe | OMe | CH | 200–202 |
| II-67 | Me | CO₂Bu | H | O | H | OMe | OMe | CH | 189–190 |
| II-68 | Me | CO₂Pen | H | O | H | OMe | OMe | CH | |
| II-69 | Me | CO₂Bn | H | O | H | OMe | OMe | CH | |
| II-70 | Me | CO₂Ph | H | O | H | OMe | OMe | CH | |
| II-71 | Me | CO₂CH₂CH₂F | H | O | H | OMe | OMe | CH | |
| II-72 | Me | CO₂CH₂CH=CH₂ | H | O | H | OMe | OMe | CH | |
| II-73 | Me | CO₂CH₂C≡CH | H | O | H | OMe | OMe | CH | |
| II-74 | Me | CO₂Me | H | O | H | OCHF₂ | OCHF₂ | CH | |
| II-75 | Me | CO₂Et | H | O | H | OCHF₂ | OCHF₂ | CH | |
| II-76 | Me | CO₂Me | H | O | H | OMe | Cl | CH | |
| II-77 | Me | CO₂Me | H | O | H | OMe | Me | CH | |
| II-78 | Me | CO₂Me | H | O | H | OMe | Me | N | |
| II-79 | Me | CO₂Et | H | O | H | OMe | Me | N | |
| II-80 | Me | CO₂Me | H | O | H | OMe | OCHF₂ | CH | |
| II-81 | Me | CO₂Me | 5-F | O | H | OMe | OMe | CH | |
| II-82 | Et | CO₂Me | H | O | H | OMe | OMe | CH | 147–148 |
| II-83 | Bu | CO₂Me | H | O | H | OMe | OMe | CH | |
| II-84 | Bn | CO₂Me | H | O | H | OMe | OMe | CH | |
| II-85 | Ph | CO₂Me | H | O | H | OMe | OMe | CH | |
| II-86 | H | CO₂Et | H | O | H | OMe | OMe | CH | |
| II-87 | Me | CO₂Me | H | S | H | OMe | OMe | CH | |
| II-88 | Me | CO₂Et | H | S | H | OMe | OMe | CH | |
| II-89 | Me | CO₂Me | H | O | Me | OMe | OMe | CH | |
| II-90 | Me | OH | H | O | H | OMe | OMe | CH | 179–181 |
| II-91 | Me | OMe | H | O | H | OMe | OMe | CH | 162–165 |
| II-92 | Me | OEt | H | O | H | OMe | OMe | CH | 153–154 |
| II-93 | Me | OPr | H | O | H | OMe | OMe | CH | 119–120 |
| II-94 | Me | OPr-i | H | O | H | OMe | OMe | CH | 176–179 |
| II-95 | Me | OBu | H | O | H | OMe | OMe | CH | 184–186 |
| II-96 | Me | OBn | H | O | H | OMe | OMe | CH | 200–203 |
| II-97 | Me | OBn(4-Cl) | H | O | H | OMe | OMe | CH | |
| II-98 | Me | OBn(3-OMe) | H | O | H | OMe | OMe | CH | |
| II-99 | Me | OBn(2-Me) | H | O | H | OMe | OMe | CH | |
| II-100 | Me | OPh | H | O | H | OMe | OMe | CH | |
| II-101 | Me | OPh(4-Cl) | H | O | H | OMe | OMe | CH | |
| II-102 | Me | OPh(3-OMe) | H | O | H | OMe | OMe | CH | |
| II-103 | Me | OPh(2-Me) | H | O | H | OMe | OMe | CH | |
| II-104 | Me | OCH₂CH=CH₂ | H | O | H | OMe | OMe | CH | 133–136 |
| II-105 | Me | OCH₂C≡CH | H | O | H | OMe | OMe | CH | 182–183 |
| II-106 | Me | OCH₂CF₃ | H | O | H | OMe | OMe | CH | 165–170 |
| II-107 | Me | OCH₂CH₂OMe | H | O | H | OMe | OMe | CH | 139–141 |
| II-108 | Me | OCH₂CH₂OPh | H | O | H | OMe | OMe | CH | |
| II-109 | Me | OCOMe | H | O | H | OMe | OMe | CH | |
| II-110 | Me | OMe | H | O | H | OMe | Me | CH | 206–208 |
| II-111 | Me | OMe | H | O | H | OMe | Me | N | 198–201 |
| II-112 | Me | OMe | H | O | H | Me | Me | CH | 193–196 |
| II-113 | Me | OEt | H | O | H | OMe | Me | N | 179–181 |
| II-114 | Me | OEt | H | O | H | OMe | Me | CH | 174–175 |
| II-115 | Me | OEt | H | O | H | Me | Me | CH | 182–183 |
| II-116 | Me | CONH₂ | H | O | H | OMe | OMe | CH | |
| II-117 | Me | CONHMe | H | O | H | OMe | OMe | CH | |
| II-118 | Me | CONHEt | H | O | H | OMe | OMe | CH | |
| II-119 | Me | CONHPr | H | O | H | OMe | OMe | CH | |
| II-120 | Me | CONMe₂ | H | O | H | OMe | OMe | CH | 150–151 |
| II-121 | Me | CONEt₂ | H | O | H | OMe | OMe | CH | |
| II-122 | Me | CONHBn | H | O | H | OMe | OMe | CH | |
| II-123 | Me | CONHPh | H | O | H | OMe | OMe | CH | |
| II-124 | Me | CONHCH₂CH=CH₂ | H | O | H | OMe | OMe | CH | |
| II-125 | Me | CONHCH₂C≡CH | H | O | H | OMe | OMe | CH | |
| II-126 | Me | CONHOMe | H | O | H | OMe | OMe | CH | |
| II-127 | Me | H | 5-F | O | H | OMe | OMe | CH | 205–208 |

TABLE 2-continued

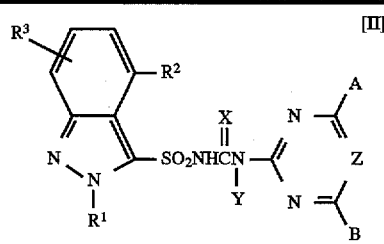

| Comp. No. | R¹ | R² | R³ | X | Y | A | B | Z | mp. (°C.) |
|---|---|---|---|---|---|---|---|---|---|
| II-128 | Me | H | 5-F | O | H | Me | Me | CH | 203–206 |
| II-129 | Me | H | 5-F | O | H | OMe | Me | CH | 186–189 |
| II-130 | Me | H | 5-F | O | H | OMe | Me | N | 175–179 |
| II-131 | H | COOMe | H | O | H | OMe | OMe | CH | 179–180 |
| II-132 | H | COOMe | H | O | H | OMe | Cl | CH | 193–194 |
| II-133 | H | Cl | H | O | H | OMe | Cl | CH | 178–181 |
| II-134 | Me | Cl | H | O | H | OMe | OMe | CH | 171–172 |
| II-135 | Me | SO₂NH₂ | H | O | H | OMe | OMe | CH | |
| II-136 | H | Br | H | O | H | OMe | OMe | CH | 190–193 |
| II-137 | Me | H | 5-OMe | O | H | OMe | OMe | CH | 178–181 |
| II-138 | Me | H | 5-OEt | O | H | OMe | OMe | CH | 188–189 |
| II-139 | Me | H | 5-OPr | O | H | OMe | OMe | CH | 197–198 |
| II-140 | Me | OCH(CF₃)Me | H | O | H | OMe | OMe | CH | 129–130 |
| II-141 | Me | OCH₂CH₂Cl | H | O | H | OMe | OMe | CH | 182–186 |
| II-142 | Me | OCH₂CH₂F | H | O | H | OMe | OMe | CH | 162–165 |
| II-143 | Me | OCH₂CH₂OEt | H | O | H | OMe | OMe | CH | 138–139 |
| II-144 | Me | OCH₂CH₂OPr-i | H | O | H | OMe | OMe | CH | 185–187 |
| II-145 | Me | OCH₂CH₂OBu | H | O | H | OMe | OMe | CH | 120–121 |
| II-146 | Me | OCH₂CH₂OBu-t | H | O | H | OMe | OMe | CH | 169–171 |
| II-147 | Me | OCH₂COOEt | H | O | H | OMe | OMe | CH | 163–165 |
| II-148 | Me | OCH₂CH₂NMe₂ | H | O | H | OMe | OMe | CH | 126–129 |
| II-149 | Me | SBu | H | O | H | OMe | OMe | CH | 156–158 |
| II-150 | Me | SPr-i | H | O | H | OMe | OMe | CH | 183–184 |
| II-151 | Me | SO₂Pr | H | O | H | OMe | OMe | CH | 202–204 |
| II-152 | Me | SO₂Bu | H | O | H | OMe | OMe | CH | 201–203 |
| II-153 | Me | SO₂Pr-i | H | O | H | OMe | OMe | CH | 185–187 |
| II-154 | Me | NHBn | H | O | H | OMe | OMe | CH | 167–168 |
| II-155 | Me | NEt₂ | H | O | H | OMe | OMe | CH | 173–175 |
| II-156 | Me | OMe | 5-Cl | O | H | OMe | OMe | CH | 211–212 |
| II-157 | Me | Br | H | O | H | OMe | Me | CH | 187–189 |
| II-158 | Et | Cl | H | O | H | OMe | Me | CH | 205–206 |
| II-159 | Ph | Cl | H | O | H | OMe | Me | CH | 215–217 |
| II-160 | Me | OPr | H | O | H | OMe | Me | CH | 174–175 |
| II-161 | Me | OBu | H | O | H | OMe | Me | CH | 169–171 |
| II-162 | Me | OPr-i | H | O | H | OMe | Me | CH | 157–159 |
| II-163 | Me | H | 5-OMe | O | H | OMe | Me | CH | 206–208 |
| II-164 | Me | H | 5-OEt | O | H | OMe | Me | CH | 174–176 |
| II-165 | Me | H | 5-OPr | O | H | OMe | Me | CH | 176–178 |
| II-166 | Me | OCH₂CF₃ | H | O | H | OMe | Me | CH | 150–153 |
| II-167 | Me | OCH(CF₃)Me | H | O | H | OMe | Me | CH | 112–114 |
| II-168 | Me | OCH₂CH₂OMe | H | O | H | OMe | Me | CH | 138–139 |
| II-169 | Me | OCH₂CH₂OEt | H | O | H | OMe | Me | CH | 160–163 |
| II-170 | Me | OCH₂CH₂OPr-i | H | O | H | OMe | Me | CH | 130–132 |
| II-171 | Me | OCH₂CH₂OBu | H | O | H | OMe | Me | CH | 104–106 |
| II-172 | Me | OCH₂CH₂OBu-t | H | O | H | OMe | Me | CH | 148–149 |
| II-173 | Me | OCH₂CH₂NMe₂ | H | O | H | OMe | Me | CH | 126–129 |
| II-174 | Me | SPr | H | O | H | OMe | Me | CH | 164–165 |
| II-175 | Me | CO₂Pr | H | O | H | OMe | Me | CH | 179–181 |
| II-176 | Me | CO₂Pr-i | H | O | H | OMe | Me | CH | 187–190 |
| II-177 | Me | CO₂Bu | H | O | H | OMe | Me | CH | 189–192 |
| II-178 | Me | NO₂ | H | O | H | OMe | Me | CH | 161–163 |
| II-179 | Me | CN | H | O | H | OMe | Me | CH | 195–197 |
| II-180 | Me | Br | H | O | H | OMe | Me | N | 172–174 |
| II-181 | Et | Cl | H | O | H | OMe | Me | N | 192–194 |
| II-182 | Me | OPr | H | O | H | OMe | Me | N | 176–177 |
| II-183 | Me | OBu | H | O | H | OMe | Me | N | 143–145 |
| II-184 | Me | OPr-i | H | O | H | OMe | Me | N | 155–156 |
| II-185 | Me | H | 5-OMe | O | H | OMe | Me | N | 171–174 |
| II-186 | Me | H | 5-OEt | O | H | OMe | Me | N | 180–182 |
| II-187 | Me | H | 5-OPr | O | H | OMe | Me | N | 168–170 |
| II-188 | Me | OCH₂CF₃ | H | O | H | OMe | Me | N | 168–170 |
| II-189 | Me | OCH₂CH₂OEt | H | O | H | OMe | Me | N | 168–170 |
| II-190 | Me | OCH₂CH₂OPr-i | H | O | H | OMe | Me | N | 153–155 |
| II-191 | Me | OCH₂CH₂OBu | H | O | H | OMe | Me | N | 121–123 |
| II-192 | Me | OCH₂CH₂OBu-t | H | O | H | OMe | Me | N | 161–162 |
| II-193 | Me | OCH₂CH₂NMe₂ | H | O | H | OMe | Me | N | 119–121 |

TABLE 2-continued

[Structure II: pyrazole fused to benzene ring with R³ and R² substituents, connected via -SO₂NHC(X)N(Y)- to a triazine/pyrimidine ring with substituents A, B, and Z; N-R¹ on pyrazole]

| Comp. No. | R¹ | R² | R³ | X | Y | A | B | Z | mp. (°C.) |
|---|---|---|---|---|---|---|---|---|---|
| II-194 | Me | SEt | H | O | H | OMe | Me | N | 160–162 |
| II-195 | Me | SPr | H | O | H | OMe | Me | N | 129–131 |
| II-196 | Me | NMe₂ | H | O | H | OMe | Me | N | 131–133 |
| II-197 | Me | CO₂Pr-i | H | O | H | OMe | Me | N | 190–191 |
| II-198 | Me | CO₂Bu | H | O | H | OMe | Me | N. | 179–181 |
| II-199 | Me | CN | H | O | H | OMe | Me | N | 196–197 |
| II-200 | Me | OMe | 5-Cl | O | H | OMe | Me | N | 201–203 |
| II-201 | Me | Cl | H | O | H | Cl | OMe | CH | 187–189 |
| II-202 | Et | Cl | H | O | H | Cl | OMe | CH | 206–208 |
| II-203 | Ph | Cl | H | O | H | Cl | OMe | CH | 202–204 |
| II-204 | Me | OMe | H | O | H | Cl | OMe | CH | 220–223 |
| II-205 | Me | OPr | H | O | H | Cl | OMe | CH | 140–141 |
| II-206 | Me | OBu | H | O | H | Cl | OMe | CH | 153–154 |
| II-207 | Me | H | 5-OMe | O | H | Cl | OMe | CH | 174–177 |
| II-208 | Me | OCH₂CF₃ | H | O | H | Cl | OMe | CH | 175–179 |
| II-209 | Me | SPr | H | O | H | Cl | OMe | CH | 165–167 |
| II-210 | Me | SBu | H | O | H | Cl | OMe | CH | 156–157 |
| II-211 | Me | SPr-i | H | O | H | Cl | OMe | CH | 177–179 |
| II-212 | Me | SO₂Pr-i | H | O | H | Cl | OMe | CH | 184–186 |
| II-213 | Me | NHBn | H | O | H | Cl | OMe | CH | 160–163 |
| II-214 | Me | NMe₂ | H | O | H | Cl | OMe | CH | 197–199 |
| II-215 | Et | Cl | H | O | H | Me | Me | CH | 229–231 |
| II-216 | Me | OPr | H | O | H | Me | Me | CH | 172–173 |
| II-217 | Me | OBu | H | O | H | Me | Me | CH | 148–149 |
| II-218 | Me | OPr-i | H | O | H | Me | Me | CH | 187–190 |
| II-219 | Me | NMe₂ | H | O | H | Me | Me | CH | 174–176 |
| II-220 | Me | OMe | H | O | H | OMe | OMe | N | 193–195 |
| II-221 | Me | H | 5-OEt | O | H | OMe | OMe | N | 169–170 |
| II-222 | Me | H | 5-OPr | O | H | OMe | OMe | N | 168–169 |
| II-223 | Me | OCH₂CH₂OBu | H | O | H | OMe | OMe | N | 132–133 |
| II-224 | Me | OCH₂CH₂OBu-t | H | O | H | OMe | OMe | N | 162–163 |
| II-225 | Me | NHMe | H | O | H | OMe | Me | CH | 164–165 |
| II-226 | Me | NHMe | H | O | H | OMe | Me | N | 173–175 |
| II-227 | Me | OMe | 5-Cl | O | H | OMe | Me | CH | 222–225 |
| II-228 | Me | OMe | 5-OMe | O | H | OMe | OMe | CH | 168–170 |
| II-229 | Me | OCHF₂ | H | O | H | OMe | OMe | CH | 179–181 |
| II-230 | Me | OCHF₂ | H | O | H | Me | OMe | CH | 195–197 |
| II-231 | Me | OCHF₂ | H | O | H | Me | OMe | N | 165–167 |
| II-232 | Me | OCH₂CHF₂ | H | O | H | OMe | OMe | CH | 178–180 |
| II-233 | Me | OCH₂CHF₂ | H | O | H | Me | OMe | CH | 180–182 |
| II-234 | Me | OCH₂CHF₂ | H | O | H | Me | OMe | N | 164–166 |
| II-235 | Me | OCH₂CH₂CF₃ | H | O | H | OMe | OMe | CH | |
| II-236 | Me | OCH₂CH₂CF₃ | H | O | H | Me | OMe | CH | |
| II-237 | Me | OCH₂CH₂CF₃ | H | O | H | Me | OMe | N | |
| II-238 | Me | OCH(CF₂CF₃)Me | H | O | H | OMe | OMe | CH | |
| II-239 | Me | OCH(CF₂CF₃)Me | H | O | H | Me | OMe | CH | |
| II-240 | Me | OCH(CF₂CF₃)Me | H | O | H | Me | OMe | N | |
| II-241 | Me | OCH₂CF₂CHF₂ | H | O | H | OMe | OMe | CH | |
| II-242 | Me | OCH₂CF₂CHF₂ | H | O | H | Me | OMe | CH | |
| II-243 | Me | OCH₂CF₂CHF₂ | H | O | H | Me | OMe | N | |
| II-244 | Me | OCH₂CF₂CF₃ | H | O | H | OMe | OMe | CH | |
| II-245 | Me | OCH₂CF₂CF₃ | H | O | H | Me | OMe | CH | |
| II-246 | Me | OCH₂CF₂CF₃ | H | O | H | Me | OMe | N | |
| II-247 | Me | OCH₂CHCl₂ | H | O | H | OMe | OMe | CH | |
| II-248 | Me | OCH₂CHCl₂ | H | O | H | Me | OMe | CH | |
| II-249 | Me | OCH₂CHCl₂ | H | O | H | Me | OMe | N | |
| II-250 | Me | OCF₂CH₂Cl | H | O | H | OMe | OMe | CH | |
| II-251 | Me | OCF₂CH₂Cl | H | O | H | Me | OMe | CH | |
| II-252 | Me | OCF₂CH₂Cl | H | O | H | Me | OMe | N | |
| II-253 | Me | OCF₂CHFCl | H | O | H | OMe | OMe | CH | |
| II-254 | Me | OCF₂CHFCl | H | O | H | Me | OMe | CH | |
| II-255 | Me | OCF₂CHFCl | H | O | H | Me | OMe | N | |
| II-256 | Me | OCF₃ | H | O | H | OMe | OMe | CH | |
| II-257 | Me | OCF₃ | H | O | H | Me | OMe | CH | |
| II-258 | Me | OCF₃ | H | O | H | Me | OMe | N | |
| II-259 | Me | OCH₂CH=CH—Cl | H | O | H | OMe | OMe | CH | 160–162 |

TABLE 2-continued

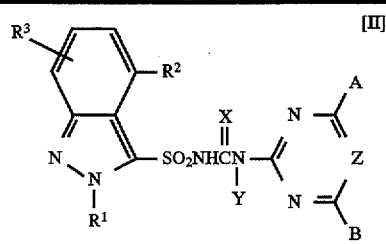

| Comp. No. | R¹ | R² | R³ | X | Y | A | B | Z | mp. (°C.) |
|---|---|---|---|---|---|---|---|---|---|
| II-260 | Me | OCH₂CH=CH—Cl | H | O | H | Me | OMe | CH | |
| II-261 | Me | OCH₂CH=CH—Cl | H | O | H | Me | OMe | N | |
| II-262 | Me | OCH₂CH=CCl₂ | H | O | H | OMe | OMe | CH | |
| II-263 | Me | OCH₂CH=CCl₂ | H | O | H | Me | OMe | CH | |
| II-264 | Me | OCH₂CH=CCl₂ | H | O | H | Me | OMe | N | |
| II-265 | Me | OCH₂C(Cl)=CH₂ | H | O | H | OMe | OMe | CH | 160–162 |
| II-266 | Me | OCH₂C(Cl)=CH₂ | H | O | H | Me | OMe | CH | |
| II-267 | Me | OCH₂C(Cl)=CH₂ | H | O | H | Me | OMe | N | |
| II-268 | Me | OCH₂C(Me)=CH₂ | H | O | H | OMe | OMe | CH | 163–164 |
| II-269 | Me | OCH₂C(Me)=CH₂ | H | O | H | Me | OMe | CH | |
| II-270 | Me | OCH₂C(Me)=CH₂ | H | O | H | Me | OMe | N | |
| II-271 | Me | OCH₂CH=CHMe | H | O | H | OMe | OMe | CH | |
| II-272 | Me | OCH₂CH=CHMe | H | O | H | Me | OMe | CH | |
| II-273 | Me | OCH₂CH=CHMe | H | O | H | Me | OMe | N | |
| II-274 | Me | OCH₂CH₂N₃ | H | O | H | OMe | OMe | CH | |
| II-275 | Me | OCH₂CH₂N₃ | H | O | H | Me | OMe | CH | |
| II-276 | Me | OCH₂CH₂N₃ | H | O | H | Me | OMe | N | |
| II-277 | Me | OCH₂OMe | H | O | H | OMe | OMe | CH | 165–167 |
| II-278 | Me | OCH₂OMe | H | O | H | Me | OMe | CH | |
| II-279 | Me | OCH₂OMe | H | O | H | Me | OMe | N | |
| II-280 | Me | OCH₂OEt | H | O | H | OMe | OMe | CH | 154–155 |
| II-281 | Me | OCH₂OEt | H | O | H | Me | OMe | CH | |
| II-282 | Me | OCH₂OEt | H | O | H | Me | OMe | N | |
| II-283 | Me | OCH₂OBn | H | O | H | OMe | OMe | CH | 162–164 |
| II-284 | Me | OCH₂OBn | H | O | H | Me | OMe | CH | |
| II-285 | Me | OCH₂OBn | H | O | H | Me | OMe | N | |
| II-286 | Me | OCH₂OCH₂CF₃ | H | O | H | OMe | OMe | CH | |
| II-287 | Me | OCH₂OCH₂CF₃ | H | O | H | Me | OMe | CH | |
| II-288 | Me | OCH₂OCH₂CF₃ | H | O | H | Me | OMe | N | |
| II-289 | Me | OCH₂OBu-t | H | O | H | OMe | OMe | CH | |
| II-290 | Me | OCH₂OBu-t | H | O | H | Me | OMe | CH | |
| II-291 | Me | OCH₂OBu-t | H | O | H | Me | OMe | N | |
| II-292 | Me | OCH₂OCH₂CH₂OMe | H | O | H | OMe | OMe | CH | |
| II-293 | Me | OCH₂OCH₂CH₂OMe | H | O | H | Me | OMe | CH | |
| II-294 | Me | OCH₂OCH₂CH₂OMe | H | O | H | Me | OMe | N | |
| II-295 | Me | OCH₂CN | H | O | H | OMe | OMe | CH | |
| II-296 | Me | OCH₂CN | H | O | H | Me | OMe | CH | |
| II-297 | Me | OCH₂CN | H | O | H | Me | OMe | N | |
| II-298 | Me | OCH₂COOMe | H | O | H | OMe | OMe | CH | |
| II-299 | Me | OCH₂COOMe | H | O | H | Me | OMe | CH | |
| II-300 | Me | OCH₂COOMe | H | O | H | Me | OMe | N | |
| II-301 | Me | OCH₂COOPr | H | O | H | OMe | OMe | CH | |
| II-302 | Me | OCH₂COOPr | H | O | H | Me | OMe | CH | |
| II-303 | Me | OCH₂COOPr | H | O | H | Me | OMe | N | |
| II-304 | Me | OCH₂COOPr-i | H | O | H | OMe | OMe | CH | |
| II-305 | Me | OCH₂COOPr-i | H | O | H | Me | OMe | CH | |
| II-306 | Me | OCH₂COOPr-i | H | O | H | Me | OMe | N | |
| II-307 | Me | OCH₂SMe | H | O | H | OMe | OMe | CH | |
| II-308 | Me | OCH₂SMe | H | O | H | Me | OMe | CH | |
| II-309 | Me | OCH₂SMe | H | O | H | Me | OMe | N | |
| II-310 | Me | OCH₂CH₂SMe | H | O | H | OMe | OMe | CH | |
| II-311 | Me | OCH₂CH₂SMe | H | O | H | Me | OMe | CH | |
| II-312 | Me | OCH₂CH₂SMe | H | O | H | Me | OMe | N | |
| II-313 | Me | SCF₃ | H | O | H | OMe | OMe | CH | |
| II-314 | Me | SCF₃ | H | O | H | Me | OMe | CH | |
| II-315 | Me | SCF₃ | H | O | H | Me | OMe | N | |
| II-316 | Me | SCH₂CH₂Cl | H | O | H | OMe | OMe | CH | |
| II-317 | Me | SCH₂CH₂Cl | H | O | H | Me | OMe | CH | |
| II-318 | Me | SCH₂CH₂Cl | H | O | H | Me | OMe | N | |
| II-319 | Me | SCH₂CH₂F | H | O | H | OMe | OMe | CH | |
| II-320 | Me | SCH₂CH₂F | H | O | H | Me | OMe | CH | |
| II-321 | Me | SCH₂CH₂F | H | O | H | Me | OMe | N | |
| II-322 | Me | SOEt | H | O | H | OMe | OMe | CH | |
| II-323 | Me | SOEt | H | O | H | Me | OMe | CH | |
| II-324 | Me | SOEt | H | O | H | Me | OMe | N | |
| II-325 | Me | SO₂NHOEt | H | O | H | OMe | OMe | CH | |

TABLE 2-continued

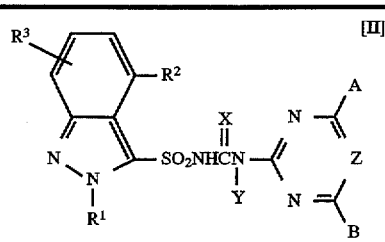

[II]

| Comp. No. | R¹ | R² | R³ | X | Y | A | B | Z | mp. (°C.) |
|---|---|---|---|---|---|---|---|---|---|
| II-326 | Me | SO₂NHOEt | H | O | H | Me | OMe | CH | |
| II-327 | Me | SO₂NHOEt | H | O | H | Me | OMe | N | |
| II-328 | Me | SO₂CH₂CH=CH₂ | H | O | H | OMe | OMe | CH | |
| II-329 | Me | SO₂CH₂CH=CH₂ | H | O | H | Me | OMe | CH | |
| II-330 | Me | SO₂CH₂CH=CH₂ | H | O | H | Me | OMe | N | |
| II-331 | Me | SO₂NEt₂ | H | O | H | OMe | OMe | CH | |
| II-332 | Me | SO₂NEt₂ | H | O | H | Me | OMe | CH | |
| II-333 | Me | SO₂NEt₂ | H | O | H | Me | OMe | N | |
| II-334 | Me | Et | H | O | H | OMe | OMe | CH | |
| II-335 | Me | Et | H | O | H | Me | OMe | CH | |
| II-336 | Me | Et | H | O | H | Me | OMe | N | |
| II-337 | Me | Pr | H | O | H | OMe | OMe | CH | |
| II-338 | Me | Pr | H | O | H | Me | OMe | CH | |
| II-339 | Me | Pr | H | O | H | Me | OMe | N | |
| II-340 | Me | Pr-i | H | O | H | OMe | OMe | CH | |
| II-341 | Me | Pr-i | H | O | H | Me | OMe | CH | |
| II-342 | Me | Pr-i | H | O | H | Me | OMe | N | |
| II-343 | Me | Bu | H | O | H | OMe | OMe | CH | |
| II-344 | Me | Bu | H | O | H | Me | OMe | CH | |
| II-345 | Me | Bu | H | O | H | Me | OMe | N | |
| II-346 | Me | Bu-t | H | O | H | OMe | OMe | CH | |
| II-347 | Me | Bu-t | H | O | H | Me | OMe | CH | |
| II-348 | Me | Bu-t | H | O | H | Me | OMe | N | |
| II-349 | Me | CH₂Cl | H | O | H | OMe | OMe | CH | |
| II-350 | Me | CH₂Cl | H | O | H | Me | OMe | CH | |
| II-351 | Me | CH₂Cl | H | O | H | Me | OMe | N | |
| II-352 | Me | CH₂F | H | O | H | OMe | OMe | CH | |
| II-353 | Me | CH₂F | H | O | H | Me | OMe | CH | |
| II-354 | Me | CH₂F | H | O | H | Me | OMe | N | |
| II-355 | Me | CH₂OMe | H | O | H | OMe | OMe | CH | |
| II-356 | Me | CH₂OMe | H | O | H | Me | OMe | CH | |
| II-357 | Me | CH₂OMe | H | O | H | Me | OMe | N | |
| II-358 | Me | CH₂CF₃ | H | O | H | OMe | OMe | CH | |
| II-359 | Me | CH₂CF₃ | H | O | H | Me | OMe | CH | |
| II-360 | Me | CH₂CF₃ | H | O | H | Me | OMe | N | |
| II-361 | Me | ◁ | H | O | H | OMe | OMe | CH | |
| II-362 | Me | ◁ | H | O | H | Me | OMe | CH | |
| II-363 | Me | ◁ | H | O | H | Me | OMe | N | |
| II-364 | Me | CH₂CH₂CF₃ | H | O | H | OMe | OMe | CH | |
| II-365 | Me | CH₂CH₂CF₃ | H | O | H | Me | OMe | CH | |
| II-366 | Me | CH₂CH₂CF₃ | H | O | H | Me | OMe | N | |
| II-367 | Me | CH₂CH=CH₂ | H | O | H | OMe | OMe | CH | |
| II-368 | Me | CH₂CH=CH₂ | H | O | H | Me | OMe | CH | |
| II-369 | Me | CH₂CH=CH₂ | H | O | H | Me | OMe | N | |
| II-370 | Me | CH₂C≡CH | H | O | H | OMe | OMe | CH | |
| II-371 | Me | CH₂C≡CH | H | O | H | Me | OMe | CH | |
| II-372 | Me | CH₂C≡CH | H | O | H | Me | OMe | N | |
| II-373 | Me | CH₂COOMe | H | O | H | OMe | OMe | CH | |
| II-374 | Me | CH₂COOMe | H | O | H | Me | OMe | CH | |
| II-375 | Me | CH₂COOMe | H | O | H | Me | OMe | N | |
| II-376 | Me | CH₂COOEt | H | O | H | OMe | OMe | CH | |
| II-377 | Me | CH₂COOEt | H | O | H | Me | OMe | CH | |
| II-378 | Me | CH₂COOEt | H | O | H | Me | OMe | N | |
| II-379 | Me | CH₂CN | H | O | H | OMe | OMe | CH | |
| II-380 | Me | CH₂CN | H | O | H | Me | OMe | CH | |

TABLE 2-continued

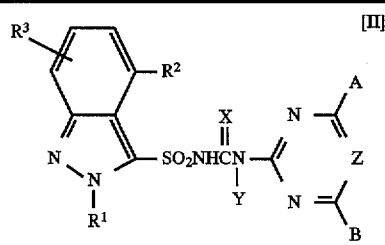

[II]

| Comp. No. | R¹ | R² | R³ | X | Y | A | B | Z | mp. (°C.) |
|---|---|---|---|---|---|---|---|---|---|
| II-381 | Me | CH₂CN | H | O | H | Me | OMe | N | |
| II-382 | Me | CH₂CONMe₂ | H | O | H | OMe | OMe | CH | |
| II-383 | Me | CH₂CONMe₂ | H | O | H | Me | OMe | CH | |
| II-384 | Me | CH₂CONMe₂ | H | O | H | Me | OMe | N | |
| II-385 | Me | CH₂SO₂NMe₂ | H | O | H | OMe | OMe | CH | |
| II-386 | Me | CH₂SO₂NMe₂ | H | O | H | Me | OMe | CH | |
| II-387 | Me | CH₂SO₂NMe₂ | H | O | H | Me | OMe | N | |
| II-388 | Me | CH₂NMe₂ | H | O | H | OMe | OMe | CH | |
| II-389 | Me | CH₂NMe₂ | H | O | H | Me | OMe | CH | |
| II-390 | Me | CH₂NMe₂ | H | O | H | Me | OMe | N | |
| II-391 | Me | CH=CH₂ | H | O | H | OMe | OMe | CH | |
| II-392 | Me | CH=CH₂ | H | O | H | Me | OMe | CH | |
| II-393 | Me | CH=CH₂ | H | O | H | Me | OMe | N | |
| II-394 | Me | CH=CHMe | H | O | H | OMe | OMe | CH | |
| II-395 | Me | CH=CHMe | H | O | H | Me | OMe | CH | |
| II-396 | Me | CH=CHMe | H | O | H | Me | OMe | N | |
| II-397 | Me | C≡CH | H | O | H | OMe | OMe | CH | |
| II-398 | Me | C≡CH | H | O | H | Me | OMe | CH | |
| II-399 | Me | C≡CH | H | O | H | Me | OMe | N | |
| II-400 | Me | C≡CMe | H | O | H | OMe | OMe | CH | |
| II-401 | Me | C≡CMe | H | O | H | Me | OMe | CH | |
| II-402 | Me | C≡CMe | H | O | H | Me | OMe | N | |
| II-403 | Me | CH=CH—COOMe | H | O | H | OMe | OMe | CH | |
| II-404 | Me | CH=CH—COOMe | H | O | H | Me | OMe | CH | |
| II-405 | Me | CH=CH—COOMe | H | O | H | Me | OMe | N | |
| II-406 | Me | CH(Me)COMe | H | O | H | OMe | OMe | CH | |
| II-407 | Me | CH(Me)COMe | H | O | H | Me | OMe | CH | |
| II-408 | Me | CH(Me)COMe | H | O | H | Me | OMe | N | |
| II-409 | Me | CH(Me)COEt | H | O | H | OMe | OMe | CH | |
| II-410 | Me | CH(Me)COEt | H | O | H | Me | OMe | CH | |
| II-411 | Me | CH(Me)COEt | H | O | H | Me | OMe | N | |
| II-412 | Me | CH(Et)COMe | H | O | H | OMe | OMe | CH | |
| II-413 | Me | CH(Et)COMe | H | O | H | Me | OMe | CH | |
| II-414 | Me | CH(Et)COMe | H | O | H | Me | OMe | N | |
| II-415 | Me | CH(Et)COEt | H | O | H | OMe | OMe | CH | |
| II-416 | Me | CH(Et)COEt | H | O | H | Me | OMe | CH | |
| II-417 | Me | CH(Et)COEt | H | O | H | Me | OMe | N | |
| II-418 | Me | CO—◁ | H | O | H | OMe | OMe | CH | |
| II-419 | Me | CO—◁ | H | O | H | Me | OMe | CH | |
| II-420 | Me | CO—◁ | H | O | H | Me | OMe | N | |
| II-421 | Me | COPr | H | O | H | OMe | OMe | CH | |
| II-422 | Me | COPr | H | O | H | Me | OMe | CH | |
| II-423 | Me | COPr | H | O | H | Me | OMe | N | |
| II-424 | Me | COPr-i | H | O | H | OMe | OMe | CH | |
| II-425 | Me | COPr-i | H | O | H | Me | OMe | CH | |
| II-426 | Me | COPr-i | H | O | H | Me | OMe | N | |
| II-427 | Me | CH=NOMe | H | O | H | OMe | OMe | CH | |
| II-428 | Me | CH=NOMe | H | O | H | Me | OMe | CH | |
| II-429 | Me | CH=NOMe | H | O | H | Me | OMe | N | |
| II-430 | Me | CH=NOEt | H | O | H | OMe | OMe | CH | |
| II-431 | Me | CH=NOEt | H | O | H | Me | OMe | CH | |
| II-432 | Me | CH=NOEt | H | O | H | Me | OMe | N | |
| II-433 | Me | C(Me)=NOMe | H | O | H | OMe | OMe | CH | |

TABLE 2-continued

[II]

| Comp. No. | R¹ | R² | R³ | X | Y | A | B | Z | mp. (°C.) |
|---|---|---|---|---|---|---|---|---|---|
| II-434 | Me | C(Me)=NOMe | H | O | H | Me | OMe | CH | |
| II-435 | Me | C(Me)=NOMe | H | O | H | Me | OMe | N | |
| II-436 | Me | C(Me)=NOEt | H | O | H | OMe | OMe | CH | |
| II-437 | Me | C(Me)=NOEt | H | O | H | Me | OMe | CH | |
| II-438 | Me | C(Me)=NOEt | H | O | H | Me | OMe | N | |
| II-439 | Me | C(Me)=NOPr | H | O | H | OMe | OMe | CH | |
| II-440 | Me | C(Me)=NOPr | H | O | H | Me | OMe | CH | |
| II-441 | Me | C(Me)=NOPr | H | O | H | Me | OMe | N | |
| II-442 | Me | C(Me)=NOCH$_2$CH$_2$Cl | H | O | H | OMe | OMe | CH | |
| II-443 | Me | C(Me)=NOCH$_2$CH$_2$Cl | H | O | H | Me | OMe | CH | |
| II-444 | Me | C(Me)=NOCH$_2$CH$_2$Cl | H | O | H | Me | OMe | N | |
| II-445 | Me | C(Me)=NOCH$_2$CH$_2$F | H | O | H | OMe | OMe | CH | |
| II-446 | Me | C(Me)=NOCH$_2$CH$_2$F | H | O | H | Me | OMe | CH | |
| II-447 | Me | C(Me)=NOCH$_2$CH$_2$F | H | O | H | Me | OMe | N | |
| II-448 | Me | NHEt | H | O | H | OMe | OMe | CH | |
| II-449 | Me | NHEt | H | O | H | Me | OMe | CH | |
| II-450 | Me | NHEt | H | O | H | Me | OMe | N | |
| II-451 | Me | NHPr | H | O | H | OMe | OMe | CH | |
| II-452 | Me | NHPr | H | O | H | Me | OMe | CH | |
| II-453 | Me | NHPr | H | O | H | Me | OMe | N | |
| II-454 | Me | NHCOOMe | H | O | H | OMe | OMe | CH | |
| II-455 | Me | NHCOOMe | H | O | H | Me | OMe | CH | |
| II-456 | Me | NHCOOMe | H | O | H | Me | OMe | N | |
| II-457 | Me | NHCOOEt | H | O | H | OMe | OMe | CH | |
| II-458 | Me | NHCOOEt | H | O | H | Me | OMe | CH | |
| II-459 | Me | NHCOOEt | H | O | H | Me | OMe | N | |
| II-460 | Me | NHCOOPh | H | O | H | OMe | OMe | CH | |
| II-461 | Me | NHCOOPh | H | O | H | Me | OMe | CH | |
| II-462 | Me | NHCOOPh | H | O | H | Me | OMe | N | |
| II-463 | Me | N(Me)SO$_2$Me | H | O | H | OMe | OMe | CH | |
| II-464 | Me | N(Me)SO$_2$Me | H | O | H | Me | OMe | CH | |
| II-465 | Me | N(Me)SO$_2$Me | H | O | H | Me | OMe | N | |
| II-466 | Me | N(Et)SO$_2$Me | H | O | H | OMe | OMe | CH | |
| II-467 | Me | N(Et)SO$_2$Me | H | O | H | Me | OMe | CH | |
| II-468 | Me | N(Et)SO$_2$Me | H | O | H | Me | OMe | N | |
| II-469 | Me | N(Me)SO$_2$Et | H | O | H | OMe | OMe | CH | |
| II-470 | Me | N(Me)SO$_2$Et | H | O | H | Me | OMe | CH | |
| II-471 | Me | N(Me)SO$_2$Et | H | O | H | Me | OMe | N | |
| II-472 | Me | N(Et)SO$_2$Et | H | O | H | OMe | OMe | CH | |
| II-473 | Me | N(Et)SO$_2$Et | H | O | H | Me | OMe | CH | |
| II-474 | Me | N(Et)SO$_2$Et | H | O | H | Me | OMe | N | |
| II-475 | Me | NHCOEt | H | O | H | OMe | OMe | CH | |
| II-476 | Me | NHCOEt | H | O | H | Me | OMe | CH | |
| II-477 | Me | NHCOEt | H | O | H | Me | OMe | N | |
| II-478 | Me | NHCOCF$_3$ | H | O | H | OMe | OMe | CH | |
| II-479 | Me | NHCOCF$_3$ | H | O | H | Me | OMe | CH | |
| II-480 | Me | NHCOCF$_3$ | H | O | H | Me | OMe | N | |
| II-481 | Me | N=CHMe | H | O | H | OMe | OMe | CH | |
| II-482 | Me | N=CHMe | H | O | H | Me | OMe | CH | |
| II-483 | Me | N=CHMe | H | O | H | Me | OMe | N | |
| II-484 | Me | N=CH—Ph | H | O | H | OMe | OMe | CH | |
| II-485 | Me | N=CH—Ph | H | O | H | Me | OMe | CH | |
| II-486 | Me | N=CH—Ph | H | O | H | Me | OMe | N | |
| II-487 | Me | N$_3$ | H | O | H | OMe | OMe | CH | |
| II-488 | Me | N$_3$ | H | O | H | Me | OMe | CH | |
| II-489 | Me | N$_3$ | H | O | H | Me | OMe | N | |
| II-490 | Me | I | H | O | H | OMe | OMe | CH | |
| II-491 | Me | I | H | O | H | Me | OMe | CH | |
| II-492 | Me | I | H | O | H | Me | OMe | N | |
| II-493 | Me | OCOEt | H | O | H | OMe | OMe | CH | |
| II-494 | Me | OCOEt | H | O | H | Me | OMe | CH | |
| II-495 | Me | OCOEt | H | O | H | Me | OMe | N | |
| II-496 | Me | OCOPr | H | O | H | OMe | OMe | CH | |
| II-497 | Me | OCOPr | H | O | H | Me | OMe | CH | |
| II-498 | Me | OCOPr | H | O | H | Me | OMe | N | |
| II-499 | Me | OCOPh | H | O | H | OMe | OMe | CH | |

TABLE 2-continued

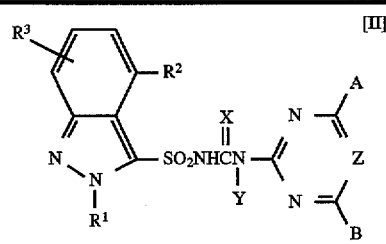

| Comp. No. | R¹ | R² | R³ | X | Y | A | B | Z | mp. (°C.) |
|---|---|---|---|---|---|---|---|---|---|
| II-500 | Me | OCOPh | H | O | H | Me | OMe | CH | |
| II-501 | Me | OCOPh | H | O | H | Me | OMe | N | |
| II-502 | Me | OCONMe₂ | H | O | H | OMe | OMe | CH | |
| II-503 | Me | OCONMe₂ | H | O | H | Me | OMe | CH | |
| II-504 | Me | OCONMe₂ | H | O | H | Me | OMe | N | |
| II-505 | Me | Cl | H | O | H | CF₃ | OMe | CH | |
| II-506 | Me | OPr-i | H | O | H | Cl | OMe | CH | |
| II-507 | Me | SEt | H | O | H | Me | OMe | CH | |
| II-508 | Me | SEt | H | O | H | Cl | OMe | CH | |
| II-509 | Me | SEt | H | O | H | Me | Me | CH | |
| II-510 | Me | SEt | H | O | H | OMe | OMe | N | |
| II-511 | Me | SBu | H | O | H | OMe | Me | CH | |
| II-512 | Me | SBu | H | O | H | OMe | Me | N | |
| II-513 | Me | SPr-i | H | O | H | OMe | Me | CH | |
| II-514 | Me | SPr-i | H | O | H | OMe | Me | N | |
| II-515 | Me | SOEt | H | O | H | OMe | OMe | N | |
| II-516 | Me | SO₂Et | H | O | H | OMe | Me | CH | |
| II-517 | Me | SO₂Et | H | O | H | OMe | Me | N | |
| II-518 | Me | SO₂Et | H | O | H | OMe | Cl | CH | |
| II-519 | Me | SO₂Pr | H | O | H | OMe | Me | CH | |
| II-520 | Me | SO₂Pr | H | O | H | OMe | Me | N | |
| II-521 | Me | SO₂Pr | H | O | H | OMe | Cl | CH | |
| II-522 | Me | SO₂Bu | H | O | H | OMe | Me | CH | |
| II-523 | Me | SO₂Bu | H | O | H | OMe | Me | N | |
| II-524 | Me | SO₂Bu | H | O | H | OMe | Cl | CH | |
| II-525 | Me | SO₂Pr-i | H | O | H | OMe | Me | CH | |
| II-526 | Me | SO₂Pr-i | H | O | H | OMe | Me | N | |
| II-527 | Me | COOPr | H | O | H | OMe | Me | N | |
| II-528 | Me | NO₂ | H | O | H | OMe | Cl | CH | |
| II-529 | Me | CONMe₂ | H | O | H | OMe | Me | CH | |
| II-530 | Me | Br | H | O | H | OMe | Cl | CH | |
| II-531 | Me | OCH₂—△ | H | O | H | OMe | OMe | CH | 156–158 |
| II-532 | Me | OCH₂—Bu-t | H | O | H | OMe | OMe | CH | 144–146 |
| II-533 | Me | OCH₂—Bu-t | H | O | H | Me | OMe | CH | 126–128 |
| II-534 | Me | OCH₂CH=CMe₂ | H | O | H | OMe | OMe | CH | 164–166 |
| II-535 | Me | OCH₂CH₂CH₂F | H | O | H | OMe | OMe | CH | 136–138 |
| II-536 | Me | OCH₂CH₂CH₂F | H | O | H | Me | OMe | CH | 173–175 |
| II-537 | Me | OCH₂CH₂CH₂F | H | O | H | Me | OMe | N | 160–163 |
| II-538 | Me | CH₂CH₂N₃ | H | O | H | OMe | OMe | CH | |
| II-539 | Me | CH₂CO—△ | H | O | H | OMe | OMe | CH | |
| II-540 | Me | COCF₃ | H | O | H | OMe | OMe | CH | |
| II-541 | Me | COOCH₂CH=CHCl | H | O | H | OMe | OMe | CH | |
| II-542 | Me | SO₂CF₃ | H | O | H | OMe | OMe | CH | |
| II-543 | Me | OCOCF₃ | H | O | H | OMe | OMe | CH | |
| II-544 | Me | OCH₂OPh | H | O | H | OMe | OMe | CH | |
| II-545 | Me | CH=NOH | H | O | H | OMe | OMe | CH | |
| II-546 | Me | CH=NOCH₂CH=CH₂ | H | O | H | OMe | OMe | CH | |
| II-547 | Me | CH=NOCH₂C≡CH | H | O | H | OMe | OMe | CH | |
| II-548 | Me | C(Me)=NOBn | H | O | H | OMe | OMe | CH | |
| II-549 | Me | C(Me)=NOPh | H | O | H | OMe | OMe | CH | |
| II-550 | Me | C(Bn)=NOMe | H | O | H | OMe | OMe | CH | |
| II-551 | Me | C(Ph)=NOMe | H | O | H | OMe | OMe | CH | |
| II-552 | Me | C(CF₃)=NOMe | H | O | H | OMe | OMe | CH | |
| II-553 | Me | COOCH₂CH₂Cl | H | O | H | OMe | OMe | CH | |
| II-554 | Me | COOCH₂CF₃ | H | O | H | OMe | OMe | CH | |
| II-555 | Me | Cl | 5-Cl | O | H | OMe | Me | N | |
| II-556 | Me | Cl | 5-OMe | O | H | OMe | OMe | CH | 197–199 |
| II-557 | Me | Cl | 5-F | O | H | OMe | OMe | CH | |

TABLE 2-continued

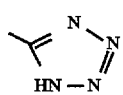

| Comp. No. | R¹ | R² | R³ | X | Y | A | B | Z | mp. (°C.) |
|---|---|---|---|---|---|---|---|---|---|
| II-558 | Me | F | 5-Cl | O | H | OMe | OMe | CH | |
| II-559 | Me | F | 5-F | O | H | OMe | OMe | CH | |
| II-560 | Me | COOMe | 5-Cl | O | H | OMe | OMe | CH | |
| II-561 | Me | COOEt | 5-Cl | O | H | OMe | OMe | CH | |
| II-562 | Me | COOPr | 5-Cl | O | H | OMe | OMe | CH | |
| II-563 | Me | COOPr-i | 5-Cl | O | H | OMe | OMe | CH | |
| II-564 | Me | OMe | 5-COOMe | O | H | OMe | OMe | CH | |
| II-565 | Me | COOMe | 5-OMe | O | H | OMe | OMe | CH | |
| II-566 | Me | H | 5-CN | O | H | OMe | OMe | CH | |
| II-567 | Me | H | 5-CF₃ | O | H | OMe | OMe | CH | |
| II-568 | Me | H | 5-COOMe | O | H | OMe | OMe | CH | |
| II-569 | Me | H | 5-COOEt | O | H | OMe | OMe | CH | |
| II-570 | Me | H | 5-COOPr | O | H | OMe | OMe | CH | |
| II-571 | Me | H | 5-COOPr-i | O | H | OMe | OMe | CH | |
| II-572 | Me | H | 5-COOCH₂CH₂Cl | O | H | OMe | OMe | CH | |
| II-573 | Me | H | 5-COOCH₂CH₂F | O | H | OMe | OMe | CH | |
| II-574 | Me | H | 5-COOCH₂CF₃ | O | H | OMe | OMe | CH | |
| II-575 | Me | H | 5-COOCH₂OMe | O | H | OMe | OMe | CH | |
| II-576 | Me | H | 5-CONMe₂ | O | H | OMe | OMe | CH | |
| II-577 | Me | H | 5-OCH₂CH₂F | O | H | OMe | OMe | CH | |
| II-578 | Me | H | 5-OCHF₂ | O | H | OMe | OMe | CH | |
| II-579 | Me | H | 5-OCH₂CF₃ | O | H | OMe | OMe | CH | |
| II-580 | Me | H | 5-OCH₂CH₂CH₂F | O | H | OMe | OMe | CH | |
| II-581 | Me | H | 5-OCH₂CH=CH₂ | O | H | OMe | OMe | CH | |
| II-582 | Me | H | 5-OCH₂C≡CH | O | H | OMe | OMe | CH | |
| II-583 | Me | H | 5-NO₂ | O | H | OMe | OMe | CH | |
| II-584 | Me | H | 5-SMe | O | H | OMe | OMe | CH | |
| II-585 | Me | H | 5-SEt | O | H | OMe | OMe | CH | |
| II-586 | Me | H | 5-SPr | O | H | OMe | OMe | CH | |
| II-587 | Me | H | 5-SPr-i | O | H | OMe | OMe | CH | |
| II-588 | Me | H | 5-SO₂Et | O | H | OMe | OMe | CH | |
| II-589 | Me | H | 5-SO₂Pr | O | H | OMe | OMe | CH | |
| II-590 | Me | H | 5-SO₂Pr-i | O | H | OMe | OMe | CH | |
| II-591 | Me | H | 5-SOEt | O | H | OMe | OMe | CH | |
| II-592 | Me | H | 5-Me | O | H | OMe | OMe | CH | |
| II-593 | Me | H | 5-Et | O | H | OMe | OMe | CH | |
| II-594 | Me | H | 5-Pr | O | H | OMe | OMe | CH | |
| II-595 | Me | H | 5-SO₂NMe₂ | O | H | OMe | OMe | CH | |
| II-596 | Me | H | 5-OCF₃ | O | H | OMe | OMe | CH | |
| II-597 | Me | H | 5-CH₂CF₃ | O | H | OMe | OMe | CH | |
| II-598 | Me | H | 5-CH₂CH=CH₂ | O | H | OMe | OMe | CH | |
| II-599 | Me | H | 5-COOMe | O | H | OMe | Me | CH | |
| II-600 | Me | H | 5-COOMe | O | H | OMe | Me | N | |
| II-601 | Me | H | 5-COOMe | O | H | OMe | OMe | N | |
| II-602 | Me | 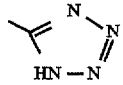 | H | O | H | OMe | OMe | CH | |
| II-603 | Me | 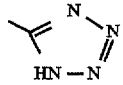 | H | O | H | Me | OMe | CH | |
| II-604 | Me | 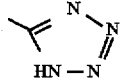 | H | O | H | Me | OMe | N | |
| II-605 | Me | 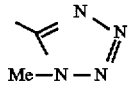 | H | O | H | OMe | OMe | CH | |

TABLE 2-continued

[Structure II: pyrazole fused benzene ring with R3, R2 substituents, N-R1, -SO2NHCN=C(X)-N(Y)- linked to pyrimidine/triazine with A, B, Z substituents]

| Comp. No. | R¹ | R² | R³ | X | Y | A | B | Z | mp. (°C.) |
|---|---|---|---|---|---|---|---|---|---|
| II-606 | Me | [Me-N-N=N-N= ring (tetrazole-like)] | H | O | H | Me | OMe | CH | |
| II-607 | Me | [Me-N-N=N-N= ring] | H | O | H | Me | OMe | N | |
| II-608 | Me | [N-N-Me, N=N ring] | H | O | H | OMe | OMe | CH | |
| II-609 | Me | [N-N-Me, N=N ring] | H | O | H | Me | OMe | CH | |
| II-610 | Me | [N-N-Me, N=N ring] | H | O | H | Me | OMe | N | |
| II-611 | Me | —O—C₂H₄—O—* | | O | H | OMe | OMe | CH | |
| II-612 | Me | —O—C₂H₄—O—* | | O | H | Me | OMe | CH | |
| II-613 | Me | —O—C₂H₄—O—* | | O | H | Me | OMe | N | |
| II-614 | Me | —S—C₂H₄—S—* | | O | H | OMe | OMe | CH | |
| II-615 | Me | —S—C₂H₄—S—* | | O | H | Me | OMe | CH | |
| II-616 | Me | —S—C₂H₄—S—* | | O | H | Me | OMe | N | |
| II-617 | Me | —O—CH₂—O—* | | O | H | OMe | OMe | CH | |
| II-618 | [2-pyridyl] | Cl | H | O | H | OMe | OMe | CH | |
| II-619 | [3-pyridyl] | Cl | H | O | H | OMe | OMe | CH | |
| II-620 | [4-pyridyl] | Cl | H | O | H | OMe | OMe | CH | |
| II-621 | COMe | Cl | H | O | H | OMe | OMe | CH | |
| II-622 | COEt | Cl | H | O | H | OMe | OMe | CH | |
| II-623 | COPr | Cl | H | O | H | OMe | OMe | CH | |
| II-624 | COPr-i | Cl | H | O | H | OMe | OMe | CH | |
| II-625 | COPh | Cl | H | O | H | OMe | OMe | CH | |
| II-626 | SO₂Me | Cl | H | O | H | OMe | OMe | CH | |
| II-627 | SO₂Et | Cl | H | O | H | OMe | OMe | CH | |
| II-628 | SO₂Ph | Cl | H | O | H | OMe | OMe | CH | |
| II-629 | COOMe | Cl | H | O | H | OMe | OMe | CH | |
| II-630 | COOEt | Cl | H | O | H | OMe | OMe | CH | |
| II-631 | COOPh | Cl | H | O | H | OMe | OMe | CH | |
| II-632 | CONMe₂ | Cl | H | O | H | OMe | OMe | CH | |
| II-633 | SO₂NMe₂ | Cl | H | O | H | OMe | OMe | CH | |
| II-634 | Ph | Cl | H | O | H | Me | OMe | N | |
| II-635 | CH₂OMe | Cl | H | O | H | OMe | OMe | CH | |
| II-636 | CH₂OBn | Cl | H | O | H | OMe | OMe | CH | |
| II-637 | CH₂CH₂F | Cl | H | O | H | OMe | OMe | CH | |

TABLE 2-continued

| Comp. No. | R¹ | R² | R³ | X | Y | A | B | Z | mp. (°C.) |
|---|---|---|---|---|---|---|---|---|---|
| II-638 | CH₂CH₂Cl | Cl | H | O | H | OMe | OMe | CH | |
| II-639 | CF₃ | Cl | H | O | H | OMe | OMe | CH | |
| II-640 | CH₂F | Cl | H | O | H | OMe | OMe | CH | |
| II-641 | CH₂CH=CH₂ | OMe | H | O | H | OMe | OMe | CH | |
| II-642 | COCF₃ | Cl | H | O | H | OMe | OMe | CH | |
| II-643 | ◁ | Cl | H | O | H | OMe | OMe | CH | |
| II-644 | Me | Cl | H | O | CH₃OCH₂ | OMe | OMe | CH | |
| II-645 | Me | Cl | H | O | H | OMe | NMe₂ | N | |
| II-646 | Me | Cl | H | O | H | OMe | NHMe | N | |
| II-648 | Me | ON=CHMe | H | O | H | OMe | OMe | CH | |
| II-649 | Me | ON=CMe₂ | H | O | H | OMe | OMe | CH | |
| II-650 | Me | ON=CHBn | H | O | H | OMe | OMe | CH | |
| II-651 | Me | OCH₂CH₂F | H | O | H | OMe | Me | CH | 167–170 |
| II-652 | Me | OCH₂CH₂F | H | O | H | OMe | Me | N | 167–169 |
| II-653 | Me | F | H | O | H | NMe₂ | OCH₂CF₃ | N | 108–112 |
| II-654 | Me | SO₂NMe₂ | H | O | H | OMe | Me | N | 191–193 |
| II-655 | Me | CO₂CH₂CH₂Cl | H | O | H | OMe | OMe | CH | |
| II-656 | Me | CO₂CH₂CF₃ | H | O | H | OMe | OMe | CH | |
| II-657 | Me | CO₂CH₂OMe | H | O | H | OMe | OMe | CH | |
| II-658 | H | CO₂CH₂CH₂Cl | H | O | H | OMe | OMe | CH | |
| II-659 | H | CO₂CH₂CF₃ | H | O | H | OMe | OMe | CH | |
| II-660 | H | CO₂CH₂OMe | H | O | H | OMe | OMe | CH | |

*R³ represents the 5-position.

The following processes may, for example, be mentioned as the processes for producing the compounds of the present invention. However, the processes are not limited to such specific processes.

Common processes for producing the compound [I] or [II] of the present invention are shown by the following Processes 1 to 3.

PROCESS 1

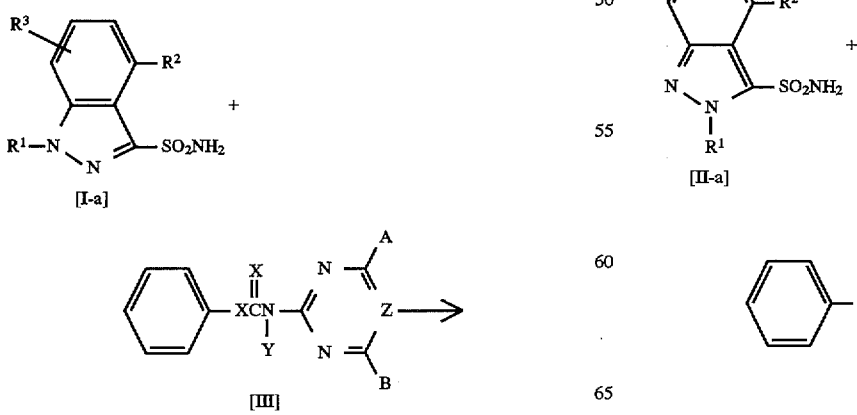

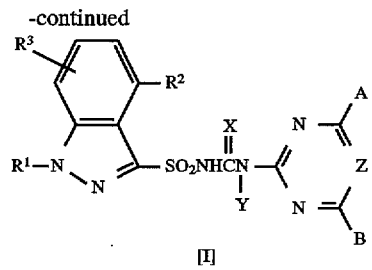

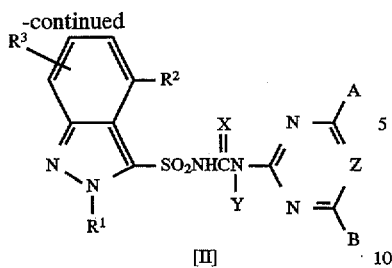

[II]

(wherein $R^1$, $R^2$, $R^3$, A, B, Z, X and Y have the same meanings as defined above.)

Namely, the compound of the present invention represented by the formula [I] or [II] can be produced by reacting an intermediate for its production of the present invention represented by the formula [I-a] or [II-a] (hereinafter referred to as an intermediate, and the process for its production will be described hereinafter) and a compound represented by the formula [III].

This reaction is usually conducted in a solvent or without solvent, if necessary, in the presence of a base. The range of the reaction temperature is a range from −20° C. to the boiling point of the solvent, and the range of the reaction time is a range of from 0.5 hour to 24 hours. With respect to the amounts of the compounds to be subjected to the reaction, the amounts of the compound represented by the formula [III] and the base are respectively independently from 1 to 1.5 equivalent relative to one equivalent of the intermediate represented by the formula [I-a] or [II-a].

As the solvent, an aromatic hydrocarbon such as benzene, xylene or toluene, a halogenated hydrocarbon such as chloroform, carbon tetrachloride, dichloroethane, chlorobenzene or dichlorobenzene, an ether such as diethyl ether, dioxane, tetrahydrofuran (THF), isopropyl ether (IPE) or diethylene glycol dimethyl ether, an alcohol such as methanol, ethanol or 2-propanol, an ester such as ethyl acetate or butyl acetate, a nitro compound such as nitromethane or nitrobenzene, a nitrile such as acetonitrile or isobutyronitrile, or an aprotic polar solvent such as formamide, N,N-dimethylformamide (DMF), N,N-dimethylacetamide (DMAC), dimethylsulfoxide (DMSO) or N-methylpyrrolidone (NMP), may, for example, be mentioned.

As the base, an organic base such as pyridine, triethylamine, 1,4-diazabicyclo[2.2.2]octane, 1,8-diazabicyclo[5.4.0]-7-undecene (DBU), N,N-diethylaniline or diethyl-methylamine, an inorganic base such as sodium hydroxide, potassium hydroxide, sodium carbonate, potassium carbonate or sodium hydride, or an alkali metal alkoxide such as sodium methoxide or sodium ethoxide, may, for example, be mentioned.

Further, the compound represented by the formula [III] can be produced by reacting a compound represented by the formula [IV] in Process 2 with phenyl chloroformate, phenyl chlorothio-O-formate or phenyl chlorodithioformate, in a proper solvent in the presence of a base.

PROCESS 2

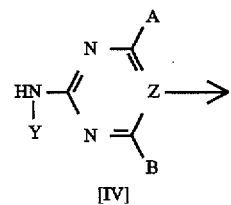

[I-b]

+

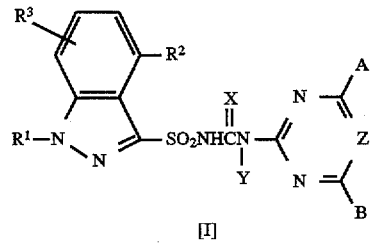

[IV]

→

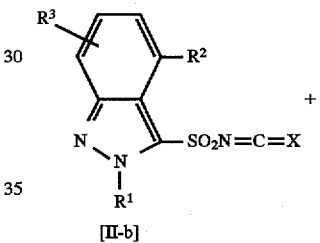

[I]

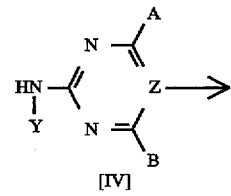

[II-b]

+

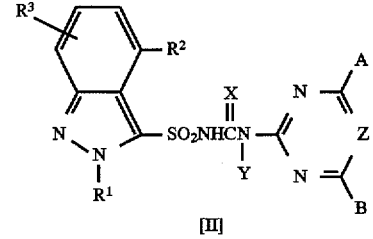

[IV]

→

[III]

(wherein $R^1$, $R^2$, $R^3$, A, B, X, Y and Z have the same meanings as defined above.)

The compound of the present invention represented by the formula [I] or [II] can be produced by reacting a compound represented by the formula [I-b] or [II-b] and a compound represented by the formula [IV]. The compound represented by the formula [I-b] or [II-b] can be produced by reacting an intermediate represented by the formula [I-a] or [II-a] with phosgene or thiophosgene in a suitable solvent.

This reaction is usually conducted in a solvent or without solvent, if necessary, in the presence of a base. The range of the reaction temperature, the range of the reaction time, and the solvent and the base to be used in the reaction are the same as in Process 1. With respect to the amounts of the compounds to be subjected to the reaction, the amounts of the compounds represented by the formula [IV] and the base are respectively independently from 1 to 1.5 equivalent relative to one equivalent of the compound represented by the formula [I-b] or [II-b].

PROCESS 3

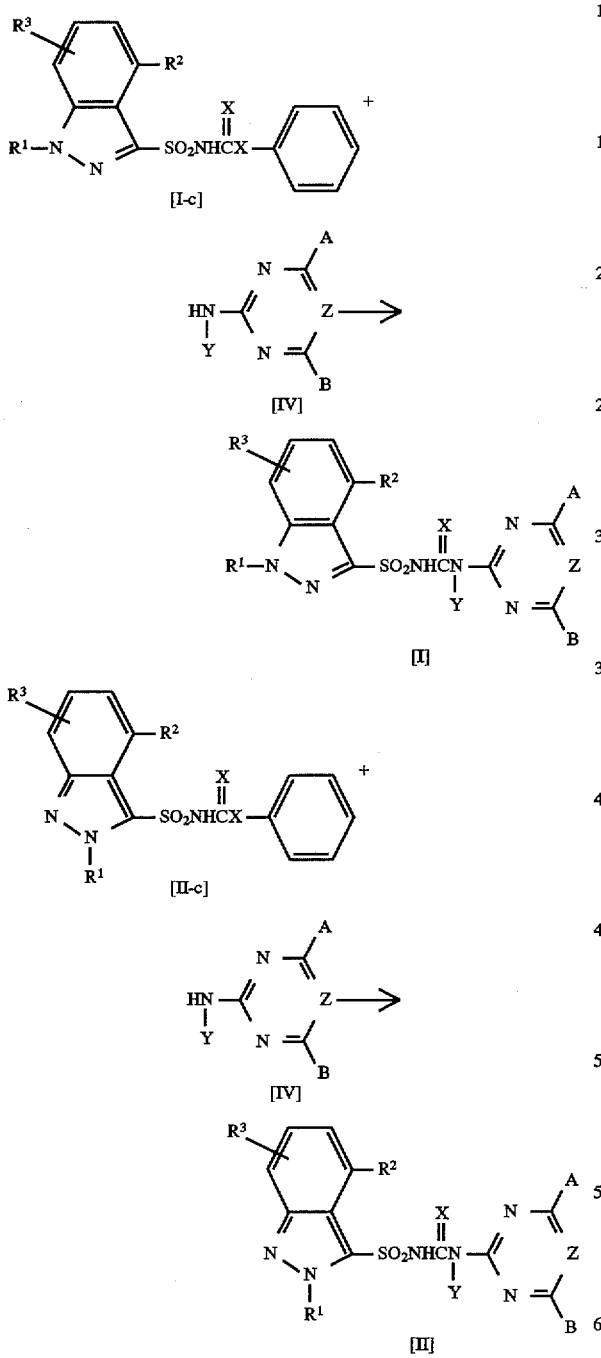

(wherein $R^1$, $R^2$, $R^3$, A, B, X, Y and Z have the same meanings as defined above.)

The compound of the present invention represented by the formula [I] or [II] can be produced by reacting a compound represented by the formula [I-c] or [II-c] and a compound of the formula [IV]. The compound represented by the formula [I-c] or [II-c] can be produced by reacting an intermediate represented by the formula [I-a] or [II-a] with phenyl chloroformate, phenyl chlorothio-O-formate or phenyl chlorodithioformate, in a suitable solvent in the presence of a base. It may also be produced by reacting a compound represented by the formula [I-b] or [II-b] with phenol or thiophenol.

This reaction is usually conducted in a solvent or without solvent, if necessary, in the presence of a base. The range of the reaction temperature, the range of the reaction time, and the solvent and the base to be used in the reaction are the same as in Process 1. With respect to the amounts of the compounds to be subjected to the reaction, the amounts of the compound represented by the formula [IV] and the base are respectively independently from 1 to 1.5 equivalent relative to one equivalent of the compound represented by the formula [I-c] or [II-c]. A process for producing an intermediate of the formula [I-a] useful for the production of the compound of the present invention will be shown by Process 1 For Producing An Intermediate, and a process for producing an intermediate of the formula [II-a] will be shown by Process 2 For Producing An Intermediate. However, the processes are not limited to such specific examples.

Process 1 For Producing An Intermediate Production of the formula [I-a]

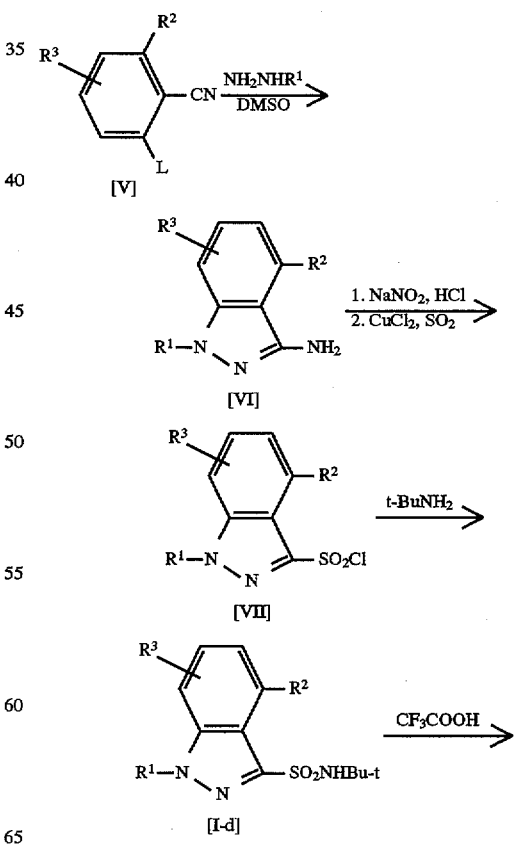

-continued

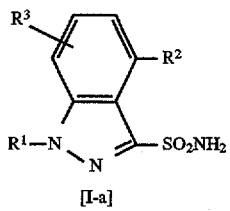

[I-a]

(wherein R¹ represents a hydrogen atom, an alkyl group, a benzyl group or a phenyl group, R² and R³ represent a hydrogen atom, an alkyl group, a halogen atom, a nitro group, an alkoxy group, a haloalkoxy group or a haloalkyl group, and L represents a halogen atom.)

Namely, a compound represented by the formula [V] is reacted with the corresponding hydrazine derivative, for example, in DMSO, to obtain a compound represented by the formula [VI]. Further, in concentrated hydrochloric acid, a diazonium salt is formed, and this is reacted with sulfurous acid gas in a solvent such as acetic acid in the presence of copper chloride to obtain a compound represented by the formula [VII]. This is reacted with excess t-butylamine to produce a compound represented by the formula [I-d]. Then, the t-butyl group is removed with excess trifluoroacetic acid to obtain an intermediate represented by the formula [I-a].

Process 2 For Producing An Intermediate Production of the formula [II-a]

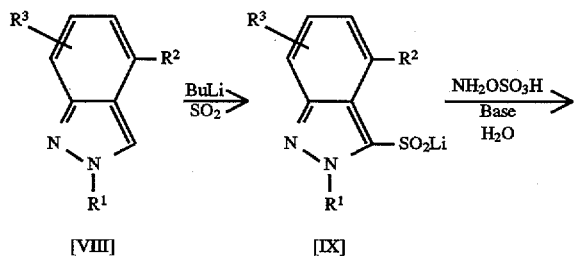

[VIII]               [IX]

-continued

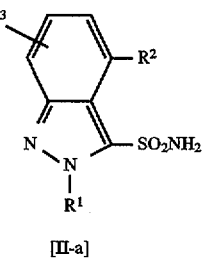

[II-a]

(wherein R¹ represents an alkyl group, a haloalkyl group, a benzyl group or a phenyl group, and R² and R³ represent a hydrogen atom, an alkyl group, a halogen atom, an alkoxy group, a phenyl group, a benzyl group or a haloalkoxy group.)

Namely, a compound represented by the formula [IX] can be produced by reacting a compound represented by the formula [VIII] with n-butyl lithium, for example, in ethyl ether, within a temperature range of from −40° to −20° C., followed by blowing in sulfurous acid gas. An intermediate represented by the formula [II-a] can be produced by adding an aqueous solution of the compound represented by the formula [IX] to an aqueous solution of a mixture of hydroxylamine-O-sulfonic acid and a base under cooling with ice.

In this reaction formula, the compound of the formula [VIII] can be produced by a method disclosed in a known literature such as [Liebigs Ann. Chem., 908 (1980)], [Org. Synth. Coll. Vol. V, 650], [J. Chem. Soc. Perkin Trans. II, 1695, (1975)], or [Org. Synth, Coll. Vol. V, 941].

The intermediate represented by the formula [I-a] or [II-a] can be produced also by the following process.

Process 3 For Producing An Intermediate Production of the formula [I-a] or [II-a]

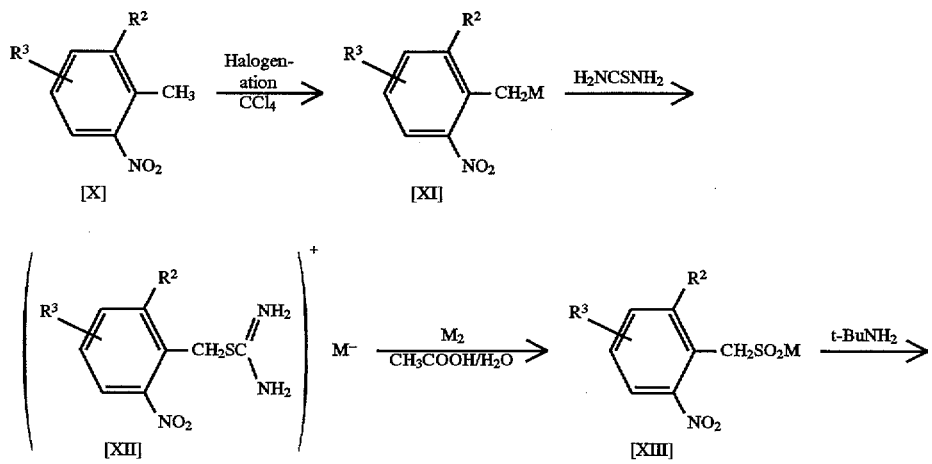

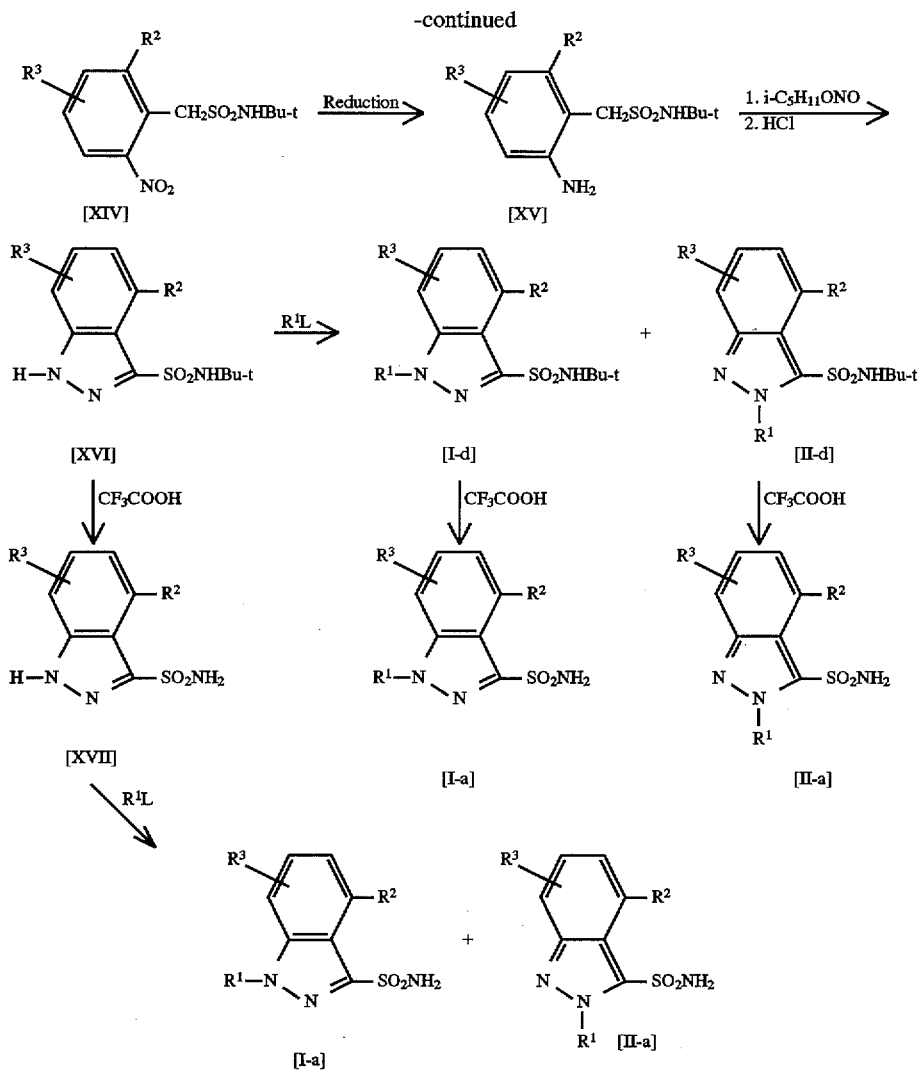

(wherein $R^1$ represents an alkyl group, a cycloalkyl group, a haloalkyl group, an alkoxyalkyl group, a benzyloxyalkyl group, a benzyl group, a dialkylaminocarbonyl group, an alkoxycarbonyl group, an alkylsulfonyl group, a phenylsulfonyl group, a dialkylaminosulfonyl group, a haloalkylcarbonyl group, an alkylcarbonyl group, a benzoyl group or an alkenyl group, $R^2$ or $R^3$ represents a hydrogen atom, a halogen atom, an alkoxy group, a haloalkoxy group, a haloalkyl group, an alkoxycarbonyl group, a phenyl group or a benzyl group, L represents a halogen atom, and M represents a bromine atom or a chlorine atom.)

Namely, a compound represented by the formula [X] is reacted with N-bromosuccinimide, N-chlorosuccinimide, or bromine or chlorine in carbon tetrachloride in the presence of a light and a radical reaction initiating agent to obtain a compound represented by the formula [XI]. The compound represented by the formula [XI] is reacted with thiourea to obtain a compound represented by the formula [XII]. The compound represented by the formula [XII] is reacted with chlorine or bromine in a mixed solution of acetic acid and water to obtain a compound represented by the formula [XIII]. Then, this compound is reacted with t-butylamine to obtain a compound represented by the formula [XIV]. The compound represented by the formula [XIV] is reduced to obtain a compound represented by the formula [XV]. The compound represented by the formula [XV] and isoamylnitrous acid are reacted, followed by reaction with hydrochloric acid to obtain a compound represented by the formula [XVI]. The compound represented by the formula [XVI] is reacted with e.g. an alkyl halide or a benzyl halide to obtain a compound represented by the formula [I-d] or [II-d].

The compound represented by the formula [XVI], [I-d] or [II-d] can be converted to a compound represented by the formula [XVII] and an intermediate represented by the formula [I-a] or [II-a], respectively, by removing the t-butyl group with trifluoroacetic acid, as shown in Process 1 For Producing An Intermediate.

Further, the compound represented by the formula [XVII] is reacted with $R^1L$ (wherein $R^1$ and L have the same meanings as defined above) to obtain intermediates of the formulas [I-a] and [II-a].

The intermediate represented by the formula [I-a] may be prepared by various processes depending upon the types of the substituents. However, it can be produced by the processes represented by the following Process 4 For Producing An Intermediate and Processes 5-1 to 5-3 For Producing An Intermediate.

Process 4 For Producing An Intermediate

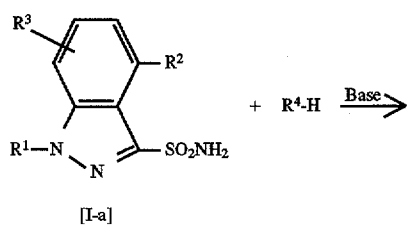

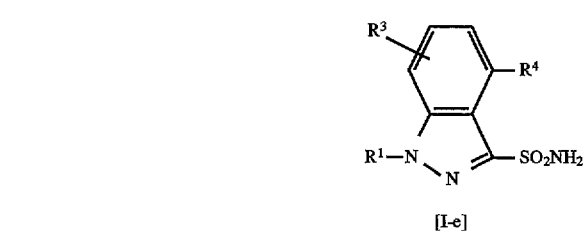

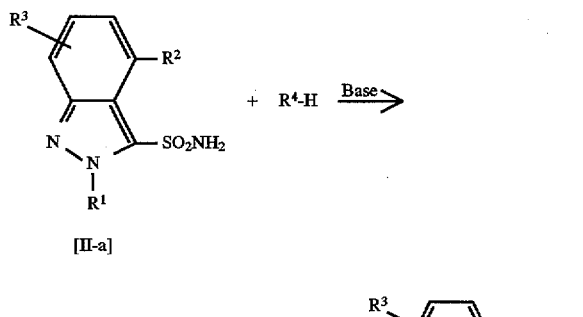

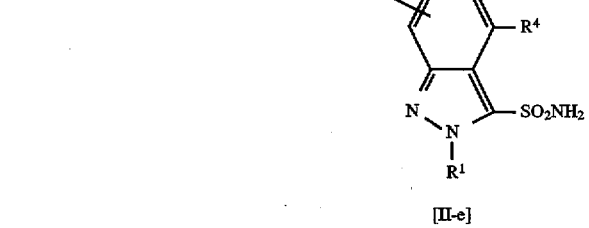

(wherein $R^1$ represents a hydrogen atom, an alkyl group, a benzyl group or a phenyl group, $R^2$ represents a halogen atom, preferably a fluorine atom, $R^3$ has the same meaning as defined above, and $R^4$ represents an alkoxy group, an alkoxyalkoxy group, a benzyloxy group, a cycloalkylalkoxy group, a haloalkoxy group, a dialkylaminoalkoxy group, an alkylthio group, an alkylamino group, a dialkylamino group or a benzylamino group.)

Namely, in this reaction, an intermediate represented by the formula [I-a] or [II-a] is reacted with a compound represented by the formula $R^4$-H (wherein $R^4$ has the same meaning as defined above) in a polar solvent such as DMSO, DMF, DMAC or NMP in the presence of a base such as sodium hydride, potassium hydride, potassium carbonate, potassium t-butoxide, sodium hydroxide or potassium hydroxide, to obtain an intermediate represented by the formula [I-e] or [II-e], respectively.

Process 5-1 For Producing An Intermediate

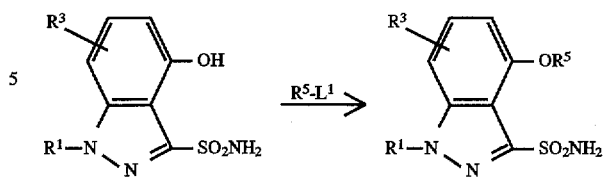

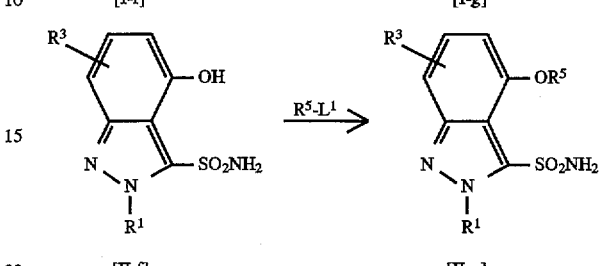

(wherein $R^1$ represents an alkyl group, a benzyl group or a phenyl group, $R^3$ has the same meaning as defined above, $R^5$ represents an alkyl group, a benzyl group, an alkenyl group, an alkynyl group, a haloalkenyl group, a haloalkyl group, an alkoxyalkyl group, an alkoxycarbonylalkyl group or a cyanoalkyl group, and $L^1$ represents a halogen atom, an alkylsulfonyloxy group, a haloalkylsulfonyloxy group or a benzenesulfonyloxy group which may be substituted.)

Namely, in this reaction formula, an intermediate represented by the formula [I-f] or [II-f] is reacted with a compound represented by the formula $R^5$-$L^1$ (wherein $R^5$ and $L^1$ have the same meanings as defined above) in a suitable solvent in the presence of a base, to obtain an intermediate represented by the formula [I-g] or [II-g], respectively.

The intermediate represented by the formula [I-f] or [II-f] can be produced by the following process.

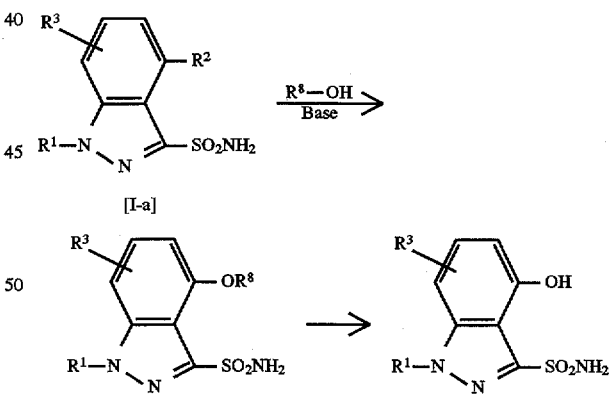

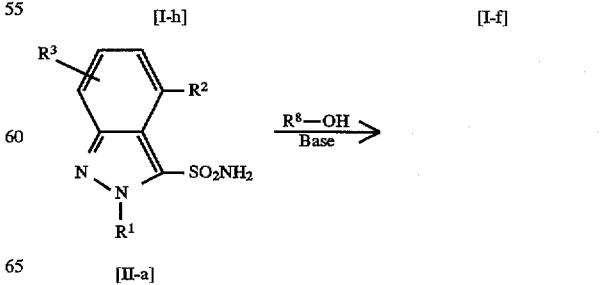

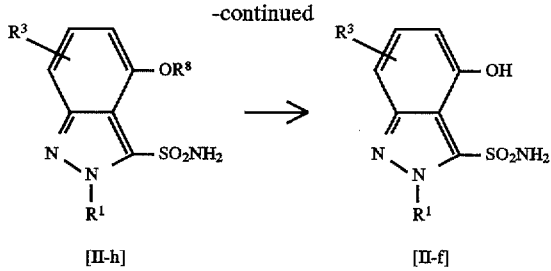

(wherein R¹ represents an alkyl group, a benzyl group or a phenyl group, R² represents a halogen atom, preferably a fluorine atom, R³ represents a hydrogen atom, a halogen atom, an alkyl group, a haloalkyl group, a haloalkoxy group or an alkoxy group, and $R^8$ represents an alkyl group, a benzyl group or a cycloalkyl group, preferably a cyclopropylmethyl group.)

Namely, in this reaction formula, an intermediate represented by the formula [I-a] or [II-a] is reacted with a compound of the formula $R^8$-OH (wherein $R^8$ has the same meaning as defined above) in a suitable solvent in the presence of a base, to obtain an intermediate represented by the formula [I-h] or [II-h], which is further subjected to removal of the protecting group to obtain an intermediate of the formula [I-f] or [II-f], respectively.

Process 5-2 For Producing An Intermediate (wherein R¹ represents an alkyl group, a benzyl group or a phenyl group, and R³ and $R^5$ have the same meanings as defined above.)

Namely, in this reaction formula, an intermediate represented by the formula [I-f] or [II-f] is subjected to a Mitsunobu reaction (as disclosed in Organic Reactions Vol. 42, p-335) using a compound represented by the formula $R^5$-OH (wherein $R^5$ has the same meaning as defined above) in a suitable solvent, to obtain an intermediate of the formula [I-g] or [II-g], respectively.

Process 5-3 For Producing an Intermediate

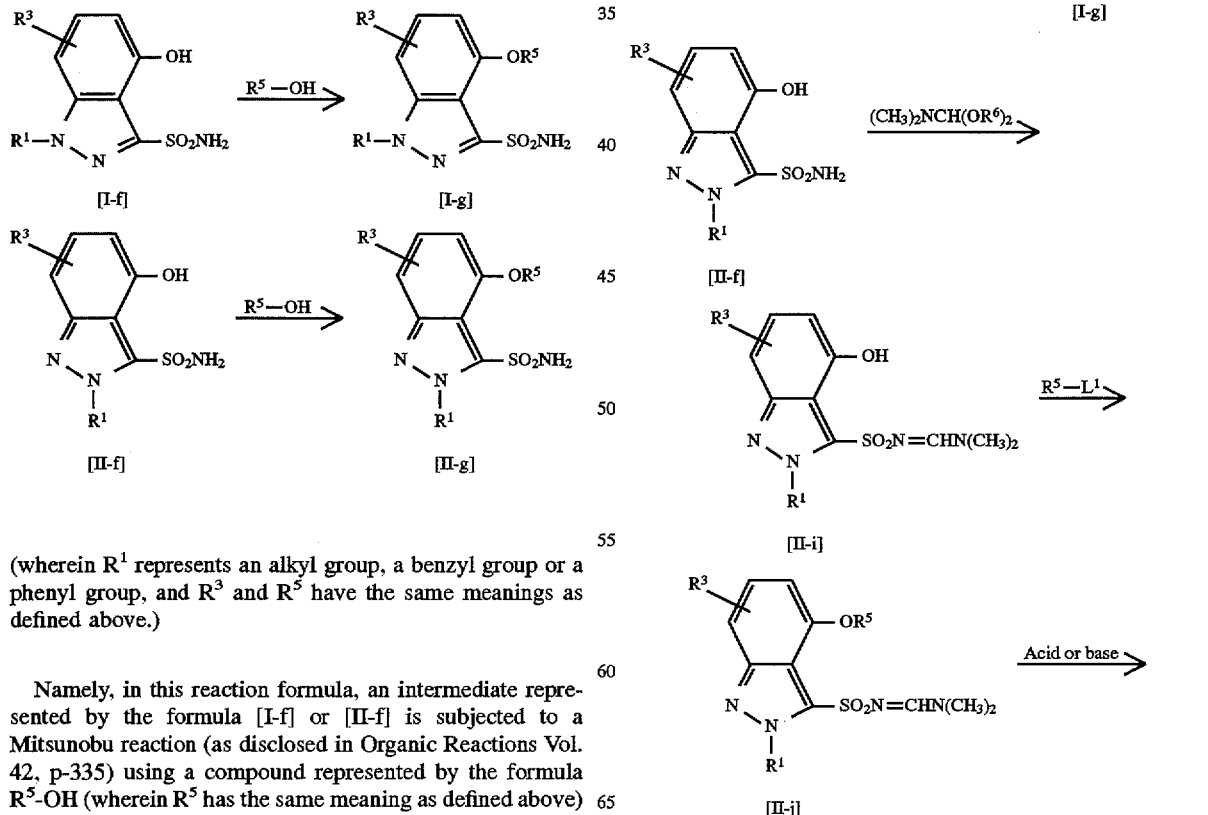

-continued

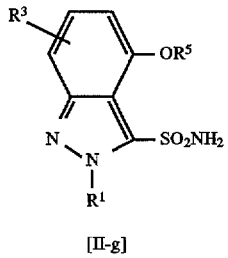

[II-g]

(wherein $R^1$ represents an alkyl group, a benzyl group or a phenyl group, $R^3$, $R^5$ and $L^1$ have the same meanings as defined above, and $R^6$ represents an alkyl group, preferably a methyl group.)

Namely, in this reaction formula, an intermediate represented by the formula [I-f] or [II-f] is reacted with acetal of DMF to obtain a compound represented by the formula [I-i] or [II-i], which is then reacted with a compound represented by the formula $R^5$-$L^1$ (wherein $R^5$ and $L^1$ have the same meanings as defined above) in a suitable solvent in the presence of a base to obtain a compound represented by the formula [I-j] or [II-j], which is then hydrolyzed with an acid or alkali to obtain an intermediate represented by the formula [I-g] or [II-g].

Now, specific compounds of the intermediate represented by the formula [I-a] or [II-a] will be listed in Table 3.

TABLE 3

| Intermediate No. | $R^1$ | $R^2$ | $R^3$ | mp. (°C.) |
|---|---|---|---|---|
| 1 | Me | Ph | H | |
| 2 | Me | Bn | H | |
| 3 | Me | SH | H | |
| 4 | Me | SMe | H | |
| 5 | Me | SEt | H | 223–225 |
| 6 | Me | SPr | H | 208–209 |
| 7 | Me | SO$_2$Me | H | |
| 8 | Me | SO$_2$Et | H | 271–273 |
| 9 | Me | SOMe | H | |
| 10 | Me | SO$_2$NHMe | H | |
| 11 | Me | SO$_2$NHOMe | H | |
| 12 | Me | SO$_2$NMe$_2$ | H | 248–252 |
| 13 | Me | SO$_2$NHBn | H | |
| 14 | Me | SO$_2$NHPh | H | |
| 15 | Me | SO$_2$NHCH$_2$CH=CH$_2$ | H | |
| 16 | Me | SO$_2$NHCH$_2$C≡CH | H | |
| 17 | H | Cl | H | 215–217 |
| 18 | Me | Cl | H | 268–270 |
| 19 | Me | Cl | 5-Cl | 283–285 |
| 20 | Et | Cl | H | 180–182 |
| 21 | Ph | Cl | H | |
| 22 | Bn | Cl | H | |
| 23 | Me | H | H | 178–180 |
| 24 | Me | F | H | 221–223 |
| 25 | Me | Br | H | 285–287 |
| 26 | Me | Me | H | |
| 27 | Me | CN | H | 274–281 |
| 28 | Me | CF$_3$ | H | |
| 29 | Me | H | 5-Cl | |
| 30 | Me | H | 6-Cl | |
| 31 | Me | H | 7-Cl | |

TABLE 3-continued

| Intermediate No. | $R^1$ | $R^2$ | $R^3$ | mp. (°C.) |
|---|---|---|---|---|
| 32 | Me | COH | H | |
| 33 | Me | COMe | H | |
| 34 | Me | COEt | H | |
| 35 | Me | COPh | H | |
| 36 | Me | CO$_2$CH$_2$CH=CH$_2$ | H | |
| 37 | Me | CO$_2$CH$_2$C≡CH | H | |
| 38 | Me | COBn | H | |
| 39 | Me | NO$_2$ | H | 249–251 |
| 40 | Me | NH$_2$ | H | |
| 41 | Me | NHMe | H | |
| 42 | Me | NMe$_2$ | H | |
| 43 | Me | NHCOMe | H | |
| 44 | Me | NHCOPh | H | |
| 45 | Me | NHCOCH$_2$Cl | H | |
| 46 | Me | NHSO$_2$CH$_3$ | H | |
| 47 | Me | NHSO$_2$Ph | H | |
| 48 | Me | CO$_2$H | H | |
| 49 | Me | CO$_2$Me | H | 233–234 |
| 50 | Me | CO$_2$Et | H | 193–195 |
| 51 | Me | CO$_2$Pr | H | 185–188 |
| 52 | Me | CO$_2$Pr-i | H | 219–220 |
| 53 | Me | CO$_2$Bu | H | 167–168 |
| 54 | Me | CO$_2$Pen | H | |
| 55 | Me | CO$_2$Bn | H | |
| 56 | Me | CO$_2$Ph | H | |
| 57 | Me | CO$_2$CH$_2$CH$_2$F | H | |
| 58 | Me | CO$_2$Me | 5-F | |
| 59 | Et | CO$_2$Me | H | |
| 60 | Bu | CO$_2$Me | H | |
| 61 | Bn | CO$_2$Me | H | |
| 62 | Ph | CO$_2$Me | H | |
| 63 | H | CO$_2$Et | H | |
| 64 | Me | OH | H | |
| 65 | Me | OMe | H | 268–270 |
| 66 | Me | OEt | H | 230–233 |
| 67 | Me | OPr | H | 210–212 |
| 68 | Me | OPr-i | H | 200–201 |
| 69 | Me | OBu | H | 203–205 |
| 70 | Me | OBn | H | |
| 71 | Me | OBn(4-Cl) | H | |
| 72 | Me | OBn(3-OMe) | H | |
| 73 | Me | OBn(2-Me) | H | |
| 74 | Me | OPh | H | |
| 75 | Me | OPh(4-Cl) | H | |
| 76 | Me | OPh(3-OMe) | H | |
| 77 | Me | OPh(2-Me) | H | |
| 78 | Me | OCH$_2$CH=CH$_2$ | H | |
| 79 | Me | OCH$_2$C≡CH | H | |
| 80 | Me | OCH$_2$CF$_3$ | H | |
| 81 | Me | OCH$_2$CH$_2$OMe | H | |
| 82 | Me | OCH$_2$CH$_2$OPh | H | |
| 83 | Me | OCOMe | H | |
| 84 | Me | CONH$_2$ | H | |
| 85 | Me | CONHMe | H | |
| 86 | Me | CONHEt | H | |
| 87 | Me | CONHPr | H | |
| 88 | Me | CONMe$_2$ | H | 274–275 |
| 89 | Me | CONEt$_2$ | H | |
| 90 | Me | CONHBn | H | |
| 91 | Me | CONHPh | H | |
| 92 | Me | CONHCH$_2$CH=CH$_2$ | H | |
| 93 | Me | CONHCH$_2$C≡CH | H | |
| 94 | Me | CONHOMe | H | |
| 95 | Me | H | 5-F | |
| 96 | Me | SO$_2$NH$_2$ | H | |
| 97 | Me | SPr-i | H | 228–231 |
| 98 | Me | OCH$_2$CH$_2$OEt | H | |
| 99 | Me | OCH$_2$CH$_2$OPr-i | H | |
| 100 | Me | OCH$_2$CH$_2$OBu | H | |
| 101 | Me | OCH$_2$CH$_2$OBu-t | H | |
| 102 | Me | OCH$_2$CH$_2$NMe$_2$ | H | |
| 103 | Me | OCH$_2$COOEt | H | |
| 104 | Me | OCH$_2$CH$_2$Cl | H | |

TABLE 3-continued

| Intermediate No. | R¹ | R² | R³ | mp. (°C.) |
|---|---|---|---|---|
| 105 | Me | OCH$_2$CH$_2$F | H | |
| 106 | Me | OCH$_2$OCH$_3$ | H | |
| 107 | Me | OCH(CF$_3$)Me | H | |
| 108 | Me | H | 5-OMe | |
| 109 | Me | H | 5-OEt | |
| 110 | Me | H | 5-OPr | |
| 111 | Et | CO$_2$Me | H | |
| 112 | Et | Br | H | |
| 113 | Me | OCHF$_2$ | H | |
| 114 | Me | SO$_2$Pr | H | 270–272 |
| 115 | Me | SO$_2$Pr-i | H | 260–263 |
| 116 | Me | SO$_2$Bu | H | 287–290 |
| 117 | Me | SBu | H | 187–189 |
| 118 | Me | OMe | 5-Cl | |
| 119 | Me | NHBn | H | |
| 120 | Me | OCH$_2$Bu-t | H | |
| 121 | Me | OCH$_2$CHF$_2$ | H | |
| 122 | H | NO$_2$ | H | >300 |
| 123 | H | Br | H | 183–186 |
| 124 | H | COOCH$_3$ | H | 243–247 |
| 125 | Me | H | 5-CO$_2$Me | 238–241 |

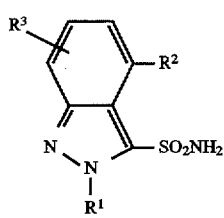

[II-a]

| Intermediate No. | R¹ | R² | R³ | mp. (°C.) |
|---|---|---|---|---|
| 126 | Me | Ph | H | |
| 127 | Me | Bn | H | |
| 128 | Me | SH | H | |
| 129 | Me | SMe | H | |
| 130 | Me | SEt | H | 145–147 |
| 131 | Me | SPr | H | |
| 132 | Me | SO$_2$Me | H | |
| 133 | Me | SO$_2$Et | H | 167–169 |
| 134 | Me | SOMe | H | |
| 135 | Me | SO$_2$NHMe | H | |
| 136 | Me | SO$_2$NHOMe | H | |
| 137 | Me | SO$_2$NMe$_2$ | H | 218–220 |
| 138 | Me | SO$_2$NHBn | H | |
| 139 | Me | SO$_2$NHPh | H | |
| 140 | Me | SO$_2$NHCH$_2$CH=CH$_2$ | H | |
| 141 | Me | SO$_2$NHCH$_2$C≡CH | H | |
| 142 | H | Cl | H | 215–217 |
| 143 | Me | Cl | H | 173–175 |
| 144 | Me | Cl | 5-Cl | |
| 145 | Et | Cl | H | 182–184 |
| 146 | Ph | Cl | H | 220–221 |
| 147 | Bn | Cl | H | |
| 148 | Me | H | H | 181–183 |
| 149 | Me | F | H | 151–152 |
| 150 | Me | Br | H | 182–183 |
| 151 | Me | Me | H | 149–151 |
| 152 | Me | CN | H | 227–228 |
| 153 | Me | CF$_3$ | H | |
| 154 | Me | H | 5-Cl | 186–188 |
| 155 | Me | H | 6-Cl | 206–207 |
| 156 | Me | H | 7-Cl | 175–177 |
| 157 | Me | COH | H | |
| 158 | Me | COMe | H | |
| 159 | Me | COEt | H | |
| 160 | Me | COPh | H | |
| 161 | Me | CO$_2$CH$_2$CH=CH$_2$ | H | |
| 162 | Me | CO$_2$CH$_2$C≡CH | H | |
| 163 | Me | COBn | H | |
| 164 | Me | NO$_2$ | H | 193–194 |
| 165 | Me | NH$_2$ | H | |
| 166 | Me | NHMe | H | 179–181 |
| 167 | Me | NMe$_2$ | H | 197–200 |
| 168 | Me | NHCOMe | H | |
| 169 | Me | NHCOPh | H | |
| 170 | Me | NHCOCH$_2$Cl | H | |
| 171 | Me | NHSO$_2$CH$_3$ | H | |
| 172 | Me | NHSO$_2$Ph | H | |
| 173 | Me | CO$_2$H | H | |
| 174 | Me | CO$_2$Me | H | 160–163 |
| 175 | Me | CO$_2$Et | H | 135–137 |
| 176 | Me | CO$_2$Pr | H | 130–132 |
| 177 | Me | CO$_2$Pr-i | H | 145–147 |
| 178 | Me | CO$_2$Bu | H | 113–114 |
| 179 | Me | CO$_2$Pen | H | |
| 180 | Me | CO$_2$Bn | H | |
| 181 | Me | CO$_2$Ph | H | |
| 182 | Me | CO$_2$CH$_2$CH$_2$F | H | |
| 183 | Me | CO$_2$Me | 5-F | |
| 184 | Et | CO$_2$Me | H | |
| 185 | Bu | CO$_2$Me | H | |
| 186 | Bn | CO$_2$Me | H | |
| 187 | Ph | CO$_2$Me | H | |
| 188 | H | CO$_2$Et | H | |
| 189 | Me | OH | H | 180–181 |
| 190 | Me | OMe | H | 265–268 |
| 191 | Me | OEt | H | 184–185 |
| 192 | Me | OPr | H | 186–188 |
| 193 | Me | OPr-i | H | 205–206 |
| 194 | Me | OBu | H | 152–154 |
| 195 | Me | OBn | H | |
| 196 | Me | OBn(4-Cl) | H | |
| 197 | Me | OBn(3-OMe) | H | |
| 198 | Me | OBn(2-Me) | H | |
| 199 | Me | OPh | H | |
| 200 | Me | OPh(4-Cl) | H | |
| 201 | Me | OPh(3-OMe) | H | |
| 202 | Me | OPh(2-Me) | H | |
| 203 | Me | OCH$_2$CH=CH$_2$ | H | 143–144 |
| 204 | Me | OCH$_2$C≡CH | H | 180–181 |
| 205 | Me | OCH$_2$CF$_3$ | H | 182–183 |
| 206 | Me | OCH$_2$CH$_2$OMe | H | 174–176 |
| 207 | Me | OCH$_2$CH$_2$OPh | H | |
| 208 | Me | OCOMe | H | |
| 209 | Me | CONH$_2$ | H | |
| 210 | Me | CONHMe | H | |
| 211 | Me | CONHEt | H | |
| 212 | Me | CONHPr | H | |
| 213 | Me | CONMe$_2$ | H | 267–270 |
| 214 | Me | CONEt$_2$ | H | |
| 215 | Me | CONHBn | H | |
| 216 | Me | CONHPh | H | |
| 217 | Me | CONHCH$_2$CH=CH$_2$ | H | |
| 218 | Me | CONHCH$_2$C≡CH | H | |
| 219 | Me | CONHOMe | H | |
| 220 | Me | H | 5-F | 174–175 |
| 221 | Me | SO$_2$NH$_2$ | H | |
| 222 | Me | SPr-i | H | 134–135 |
| 223 | Me | OCH$_2$CH$_2$OEt | H | 116–120 |
| 224 | Me | OCH$_2$CH$_2$OPr-i | H | 118–119 |
| 225 | Me | OCH$_2$CH$_2$OBu | H | 144–145 |
| 226 | Me | OCH$_2$CH$_2$OBu-t | H | 183–184 |
| 227 | Me | OCH$_2$CH$_2$NMe$_2$ | H | 184–187 |
| 228 | Me | OCH$_2$COOEt | H | 116–120 |
| 229 | Me | OCH$_2$CH$_2$Cl | H | 177–179 |
| 230 | Me | OCH$_2$CH$_2$F | H | 178–180 |
| 231 | Me | OCH$_2$OCH$_3$ | H | 163–165 |
| 232 | Me | OCH(CF$_3$)Me | H | 165–167 |
| 233 | Me | H | 5-OMe | 169–172 |
| 234 | Me | H | 5-OEt | 152–153 |
| 235 | Me | H | 5-OPr | 149–151 |
| 236 | Et | CO$_2$Me | H | 123–125 |
| 237 | Et | Br | H | |
| 238 | Me | OCHF$_2$ | H | 164–166 |
| 239 | Me | SO$_2$Pr | H | 176–178 |
| 240 | Me | SO$_2$Pr-i | H | 220–221 |

TABLE 3-continued

| Intermediate No. | R¹ | R² | R³ | mp. (°C.) |
|---|---|---|---|---|
| 241 | Me | SO₂Bu | H | 156–158 |
| 242 | Me | SBu | H | 162–164 |
| 243 | Me | OMe | 5-Cl | 161–163 |
| 244 | Me | NHBn | H | 189–191 |
| 245 | Me | OCH₂Bu-t | H | 207–208 |
| 246 | Me | OCH₂CHF₂ | H | 186–188 |
| 247 | Me | OCH₂CH₂CH₂F | H | 139–140 |
| 248 | Me | OMe | H | 138–140 |
| 249 | Me | Cl | H | 176–178 |
| 250 | Me | OCH₂OEt | H | 148–150 |
| 251 | Me | OCH₂C(CH₃)=CH₂ | H | 132–134 |
| 252 | Me | OCH₂CH=C(Me)₂ | H | 141–143 |
| 253 | Me | OCH₂CH=CHCl | H | 164–166 |
| 254 | Me | OCH₂—◁ | H | 139–141 |
| 255 | Me | OCH₂OBn | H | 156–158 |

BEST MODE FOR CARRYING OUT THE INVENTION

Now, the present invention will be specifically explained by describing the process for producing the intermediate and the process for producing the compound of the present invention as Preparation Examples.

PREPARATION EXAMPLE 1

Preparation of 1-methyl-4-fluoro-1H-indazole-3-sulfonamide (Intermediate No. 24)

75 g (539 mmol) of 2,6-difluorobenzonitrile was added to 300 ml of DMSO, and 33 g (716 mmol) of methylhydrazine was dropwise added thereto with stirring. The reaction proceeded exothermically, and the dropwise addition was continued while maintaining the temperature at a level of from 80° to 100° C. After returning to room temperature, the mixture was poured into a large excess amount of cool water, whereupon crystals were collected by filtration and dried in air to obtain 72 g (yield: 81%) of 3-amino-1-methyl-4-fluoro-1H-indazole (compound represented by the formula [VI]) (slightly yellow crystals).

Then, 70 g (424 mmol) of 3-amino-1-methyl-4-fluoro-1H-indazole was dissolved in 200 ml of acetic acid, and 140 ml of concentrated hydrochloric acid was added thereto. The mixture was vigorously stirred, and a solution having 33 g (478 mmol) of sodium nitrite dissolved in 60 ml of water, was gradually dropwise added thereto within a range of from −5° to −10° C. The diazonium salt solution thus obtained, was gradually dropwise added to a mixture having 17 g (100 mmol) of cupric chloride dihydrate added to a solution obtained by blowing sulfurous acid gas into 370 ml of acetic acid until saturation (120 g). After completion of the dropwise addition, stirring was continued for one hour at a temperature of not higher than 0° C., and then the mixture was poured into a large excess amount of cold water, whereupon crystals were collected by filtration and dried in air to obtain 70 g (yield: 66%) of 1-methyl-4-fluoro-1H-indazole-3-sulfonylchloride (compound represented by the formula [VII]) (slightly purple crystals).

Further, 13.9 g (56 mmol) of 1-methyl-4-fluoro-1H-indazole-3-sulfonylchloride in 50 ml of THF, was added to 12.9 g (177 mmol) of t-butylamine in 100 ml of THF, and the mixture was stirred at room temperature overnight. After completion of the reaction, the mixture was poured into a large excess amount of water, whereupon the crystals were collected by filtration and dried in air to obtain 15.9 g (yield: 99.6%) of 3-(N-t-butylsulfamoyl)-1-methyl-4-fluoro-1H-indazole (compound represented by the formula [I-d]) (slightly purple crystals).

15 g (53 mmol) of 3-(N-t-butylsulfamoyl)-1-methyl-4-fluoro-1H-indazole was added to 50 ml of trifluoroacetic acid, and the mixture was stirred overnight. After completion of the reaction, trifluoroacetic acid was distilled off under reduced pressure, and the residue was washed with n-hexane to obtain 10.5 g (yield: 86.8%) of 1-methyl-4-fluoro-1H-indazole-3-sulfonamide (slightly purple crystals). Melting point: 221°–223° C.

PREPARATION EXAMPLE 2

Preparation of 1-(1-methyl-4-fluoro-1H-indazole-3-sulfonyl)-3-(4,6-dimethoxypyrimidin-2-yl)urea (Compound No. I-26)

0.35 g (2.3 mmol) of DBU was added to a solution containing 0.5 g (2.3 mmol) of 1-methyl-4-fluoro-1H-indazole-3-sulfonamide obtained in Preparation Example 1 and 0.62 g (2.3 mmol) of phenyl (4,6-dimethoxypyrimidin-2-yl)carbamate in 20 ml of acetonitrile, and the mixture was stirred at room temperature for 12 hours. The mixture was poured into ice water and acidified with citric acid, whereupon the formed crystals were collected by filtration and washed with ice water, IPE and ethyl ether to obtain 0.49 g (yield: 52%) of the desired product (colorless needle like crystals). Melting point: 205°–209° C.

PREPARATION EXAMPLE 3-1

Preparation of methyl 2-bromomethyl-3-nitrobenzoate (compound represented by the formula [XI])

A suspension containing 98 g (0.5 mol) of methyl 2-methyl-3-nitrobenzoate, 100 g (0.56 mol) of N-bromosuccinimide and 1 g of benzoyl peroxide in carbon tetrachloride (800 ml), was refluxed for 3 days under irradiation with 500W. The suspension was cooled to room temperature and subjected to filtration, whereupon the filtrate was concentrated. To the residue, ethyl ether (200 ml) and IPE (200 ml) were added, whereupon the formed crystals were collected by filtration to obtain 121 g (yield: 88.3%) of the desired product. Melting point: 65°–67° C.

PREPARATION EXAMPLE 3-2

Preparation of S-(2-methoxycarbonyl-6-nitrobenzyl) thiouronium bromide (compound represented by the formula [XII]

In methanol (2 l), 207 g (0.76 mol) of the product from Preparation Example 3-1 and 57.6 g (0.76 mol) of thiourea were refluxed for 12 hours. After cooling, methanol was distilled off, and ethyl acetate (1 l) was added to the residue. The product was subjected to filtration. This product was used for the subsequent reaction without purification. The obtained amount: 246 g (yield: 93%)

PREPARATION EXAMPLE 3-3

Preparation of methyl 2-(t-butylaminosulfonylmethyl)-3-nitrobenzoate (compounds represented by the formulas [XIII] and [XIV])

110 g (0.32 mol) of the product from Preparation Example 3-2 in water (2 l) and acetic acid (1 l), was cooled to 5° C.

and chlorine was blown thereto for 4 hours at a temperature of from 5° to 10° C. And, the mixture was stirred at room temperature for one hour. Then, the product was collected by filtration and washed with ice water and then dissolved in 1 l of dichloromethane. To this solution, 54 g (0.74 mol) of t-butylamine was dropwise added at a temperature of from 0° to 5° C. Then, the mixture was stirred at room temperature for 2 hours. The organic layer was washed with water and then concentrated. IPE was added to the residue, followed by filtration to obtain 63 g (yield: 60.1%) of the desired product. This product was used for the subsequent reaction without purification.

PREPARATION EXAMPLE 3-4

Preparation of methyl 3-amino-2-(t-butylaminosulfonylmethyl)benzoate (compound represented by the formula [XV])

A solution containing 48 g (0.145 mol) of the product from Preparation Example 3-3 and 164 g (0.73 mol) of stannous chloride dihydrate in 300 ml of ethanol, was refluxed for 2 hours. After cooling, it was added to 2 l of ethyl acetate, and powdery sodium hydrogencarbonate (500 g) was gradually added thereto. The formed salt was collected by filtration and thoroughly washed with ethyl acetate. The organic layer was concentrated to obtain 35.9 g (yield: 82.4%) of the desired product. Melting point: 123°–125° C.

PREPARATION EXAMPLE 3-5

Preparation of methyl 3-(t-butylaminosulfonyl)-1H-indazole-4-carboxylate (compound represented by the formula [XVI])

A suspension containing 30 g (0.1 mol) from Preparation Example 3-4, 30.6 g (0.3 mol) of acetic anhydride and 10 g (0.102 mol) of potassium acetate in benzene (500 ml), was heated to 80° C., and at the same temperature, 17.6 g (0.15 mol) of isoamyl nitrite was dropwise added thereto. Further, the mixture was refluxed for 12 hours and then cooled, and the salt was filtered. The organic layer was concentrated, and methanol (500 ml) and 10% hydrochloric acid (20 ml) were added to the residue, and the mixture was refluxed for one hour. After distilling off methanol, water was added thereto, and the mixture was neutralized with an aqueous sodium hydrogencarbonate solution. The formed crystals were collected by filtration to obtain 29.3 g (yield: 94.1%) of the desired product. Melting point: 218°–220° C.

PREPARATION EXAMPLE 3-6

Preparation of methyl 3-(t-butylaminosulfonyl)-1-methyl-1H-indazole-4-carboxylate and methyl 3-(t-butylaminosulfonyl) 2-methyl-2H-indazole-4-carboxylate (compounds represented by the formulas [I-d] and [II-d])

6.8 g (48 mmol) of methyl iodide was added to a solution containing 10 g (32 mmol) of the product from Preparation Example 3-5 and 6.6 g (48 mmol) of potassium carbonate in methanol (200 ml), and the mixture was refluxed for 3 hours. Methanol was distilled off, and water was added to the residue, and the mixture was extracted with ethyl acetate. The organic layer was washed with water, dried over anhydrous magnesium sulfate, then concentrated and purified by silica gel column chromatography to obtain 5.9 g (yield: 56.8%; melting point: 189°–190° C.) of methyl 3-(t-butylaminosulfonyl)-1-methyl-1H-indazole-4-carboxylate and 2.1 g (yield: 19.8%; melting point: 147°–148° C.) of methyl 3-(t-butylaminosulfonyl) 2-methyl-2H-indazole-4-carboxylate.

PREPARATION EXAMPLE 4

Preparation of 2-methyl-2H-indazole-3-sulfonamide (Intermediate No. 148)

A solution containing 9.5 g (72 mmol) of 2-methyl-2H-indazole in 200 ml of ethyl ether, was cooled to −30° C., and 61.4 g (144 mmol) of n-butyl lithium (a 15% hexane solution) was dropwise added thereto. The mixture was stirred for one hour at the same temperature, and then an excess amount of sulfurous acid gas was blown thereinto for 3 hours at a temperature of not higher than −20° C. After completion of the reaction, the mixture was returned to room temperature, stirred for 12 hours and then diluted with ethyl ether. The product was subjected to filtration. The crystals were dried to obtain crude lithium 2-methyl-2H-indazole-3-sulfinate. This product was used for the subsequent reaction without purification. 48.8 g (430 mmol) of hydroxylamine-O-sulfonic acid was gradually added to a solution containing 17.2 g (430 mmol) of sodium hydroxide in water (300 ml) under cooling with ice (not higher than 10° C.). This solution was added all at once to a solution containing the crude lithium 2-methyl-2H-indazole-3-sulfinate previously prepared in water (100 ml), and then the mixture was stirred for 12 hours at room temperature. Formed crystals were collected by filtration to obtain 8.8 g (yield: 58%) of 2-methyl-2H-indazole-3-sulfonamide (slightly yellow granular crystals). Melting point: 181°–183° C.

PREPARATION EXAMPLE 5

Preparation of 1-(2-methyl-2H-indazole-3-sulfonyl)-3-(4,6-dimethoxypyrimidin-2-yl)urea (Compound No. II-23)

2.3 g (15 mmol) of DBU was added to a solution containing 3.2 g (15 mmol) of 2-methyl-2H-indazole-3-sulfonamide obtained in Preparation Example 4 and 4.1 g (15 mmol) of phenyl (4,6-dimethoxypyrimidin-2-yl) carbamate in acetonitrile (50 ml), and the mixture was stirred at room temperature for 12 hours. The mixture was poured into ice water and acidified with citric acid. Formed crystals were collected by filtration and washed with ice water, IPE and ethyl ether, to obtain 4.0 g (yield: 68%) of the desired product (colorless needle like crystals). Melting point: 199°–202° C.

PREPARATION EXAMPLE 6

Preparation of 4-methoxy-1-methyl-1H-indazole-3-sulfonamide (Intermediate No. 65)

A solution containing 5 g (21.8 mmol) of 4-fluoro-1-methyl-1H-indazole-3-sulfonamide and 12.6 g of sodium methoxide (a 28% methanol solution) (65 mmol) in DMSO (50 ml), was stirred at 130° C. for one hour. After confirming the disappearance of the starting material by thin layer chromatography (TLC), the mixture was poured into ice water and acidified with citric acid. Formed crystals were collected by filtration and washed with water and IPE to obtain 3.2 g (yield: 60.9%) of the desired product. Melting point: 268°–270° C.

PREPARATION EXAMPLE 7

Preparation of 4-ethylthio-2-methyl-2H-indazole-3-sulfonamide (Intermediate-No. 130)

4.8 g (77 mmol) of ethanethiol was added to a solution containing 8.6 g (77 mmol) of potassium t-butoxide in DMSO (70 ml), under cooling with ice, and 8 g (35 mmol) of 4-fluoro-2-methyl-2H-indazole-3-sulfonamide was further added thereto. This mixture was stirred at 120° C. for 2 hours. After confirming the disappearance of the starting material by TLC, treatment was conducted in the same manner as in Preparation Example 6 to obtain 6.8 g (yield: 72.5%) of the desired product. Melting: 145°–147° C.

PREPARATION EXAMPLE 8-1

Preparation of 4-cyclopropylmethoxy-2-methyl-2H-indazole-3-sulfonamide (Intermediate No. 254)

2.8 g (70 mmol) of 60% sodium hydride was suspended in 50 ml of DMSO, and 6 g (83 mmol) of cyclopropane methanol was dropwise added thereto. The mixture was stirred at room temperature for one hour, and then 5.4 g (24 mmol) of 4-fluoro-2-methyl-2H-indazole-3-sulfonamide was added thereto. The mixture was stirred at 130° C. for 3 hours. After the reaction, the mixture was poured into ice water, acidified with citric acid and extracted with ethyl acetate. The organic layer was washed with water and then concentrated. Formed crystals were collected by filtration, washed with IPE and then dried to obtain 5.8 g (yield: 90%) of the desired product. Melting point: 139°–141° C.

PREPARATION EXAMPLE 8-2

Preparation of 4-hydroxy-2-methyl-2H-indazole-3-sulfonamide (Intermediate No. 189)

A mixture comprising 62 g (221 mmol) of 4-cyclopropylmethoxy-2-methyl-2H-indazole-3-sulfonamide, 120 ml of acetic acid and 120 ml of concentrated hydrochloric acid, was stirred at 80° C. for one hour. After concentrating acetic acid.hydrochloric acid, the mixture was poured into ice water. Crystals were collected by filtration and washed with water. Further, the crystals were washed with IPE and dried to obtain 35.1 g (yield: 70%) of the desired product. Melting point: 180°–181° C.

PREPARATION EXAMPLE 8-3

Preparation of 4-allyloxy-2-methyl-2H-indazole-3-sulfonamide (Intermediate No. 203)

1.3 g of allyl bromide was added to a mixture comprising 5 g (22 mmol) of 4-hydroxy-2-methyl-2H-indazole-3-sulfonamide and 50 ml of a DMF solution of 1.9 g (22 mmol) of sodium hydrogencarbonate, and the mixture was stirred at room temperature for 12 hours. The mixture was poured into ice water, acidified with citric acid and extracted with ethyl acetate. The organic layer was washed, then concentrated and purified by column chromatography (hexane/ethyl acetate=2/1) to obtain 1.9 g (yield: 32.5%) of the desired product. Melting point: 143°–144° C.

PREPARATION EXAMPLE 9

Preparation of 4-(2-chloroethoxy-2-methyl-2H-indazole-3-sulfonamide (Intermediate No. 229) (Mitsunobu reaction)

3.8 g (22 mmol) of diethylazo dicarboxylate was added to a solution containing 5 g (22 mmol) of 4-hydroxy-2-methyl-2H-indazole-3-sulfonamide, 1.8 g (22 mmol) of 2-chloroethanol and 5.8 g (22 mmol) of triphenylphosphine in 50 ml of THF, and the mixture was stirred at room temperature for 20 hours. The mixture was poured into water and extracted with ethyl acetate. The organic layer was washed with water, then concentrated and purified by column chromatography (hexane/ethyl acetate=2/1) to obtain 1.66 g (yield: 26%) of the desired product. Melting point: 177°–179° C.

PREPARATION EXAMPLE 10-1

Preparation of $N^1$, $N^1$-dimethyl-$N^2$-[(4-hydroxy-2-methyl-2H-indazol-3-yl)sulfonyl]formamidine (compound represented by the formula [II-i])

21.3 g (174 mmol) of dimethylformamide dimethylacetal was dropwise added to a solution containing 33 g (145 mmol) of 4-hydroxy-2-methyl-2H-indazole-3-sulfonamide in 200 ml of acetonitrile, at room temperature. The mixture was stirred for one hour, then poured into ice water and extracted with ethyl acetate. The organic layer was washed with water, then concentrated and purified by column chromatography to obtain 35.2 g (yield: 86.3%) of the desired product. Melting point: 118°–119° C.

PREPARATION EXAMPLE 10-2

Preparation of $N^1$,$N^1$-dimethyl-$N^2$-{[4-(2-fluoroethoxy)-2-methyl-2H-indazol-3-yl]sulfonyl}formamidine (compound represented by the formula [II-j])

4.2 g (15 mmol) of $N^1$,$N^1$-dimethyl-$N^2$-[(4-hydroxy-2-methyl-2H-indazol-3-yl)sulfonyl]formamidine was added to a suspension containing 0.6 g (15 mmol) of 60% sodium hydride in 50 ml of DMF, and the mixture was stirred at room temperature for one hour. Further, 2 g (16 mmol) of 1-bromo-2-fluoroethane was added thereto, and the mixture was stirred at room temperature for 12 hours. The mixture was poured into ice water, and the formed crystals were collected by filtration and washed with water and IPE to obtain the desired product. This product was used for the subsequent reaction without purification. Obtained amount: 3.4 g (yield: 69.5%)

PREPARATION EXAMPLE 10-3

Preparation of 4-(2-fluoroethoxy)-2-methyl-2H-indazole-3-sulfonamide (Intermediate No. 230)

A mixture comprising 3.4 g of $N^1$,$N^1$-dimethyl-$N^2$-{[4-(2-fluoroethoxy)-2-methyl-2H-indazol-3-yl]sulfonyl}formamidine, 5 ml of concentrated hydrochloric acid and 50 ml of ethanol, was refluxed for 12 hours. Disappearance of the starting material was confirmed by TLC, and then ethanol was distilled off. Water was added to the residue, whereupon the formed crystals were collected by filtration and washed with water and IPE to obtain 2.4 g (yield: 85%) of the desired product. Melting point: 178°–180° C.

PREPARATION EXAMPLE 11

Preparation of 4-chloro-2-methyl-2H-indazole-3-sulfonamide (Intermediate No. 143)

36.1 g (0.24 mol) of 4-chloro-1H-indazole was added to a solution containing 28.4 g (0.7 mol) of sodium hydroxide in 500 ml of methanol, and 85.2 g (0.6 mol) of methyl iodide was dropwise added thereto. The mixture was heated and refluxed for 4 hours. Then, methanol was distilled off, and water was added to the residue, followed by extraction with dichloromethane. The organic layer was washed with water, dried and concentrated to obtain a mixture of 4-chloro-1- methyl-1H-indazole and 4-chloro-2-methyl-2H-indazole. This mixture was separated by silica gel column chromatography (ethyl acetate/hexane=4/1) to obtain 17.4 g (yield: 43.6%) of 4-chloro-2-methyl-2H-indazole (yellow liquid, refractive index (20° C.): 1.6095).

A solution containing 16 g (0.1 mol) of 4-chloro-2-methyl-2H-indazole in 300 ml of ethyl ether, was cooled to −30° C., and 85.4 g (0.2 mol) of n-butyl lithium (15% hexane solution) was dropwise added thereto. The mixture was stirred for one hour at the same temperature. Then, an excess amount of sulfurous acid gas was blown thereinto at a temperature of not higher than −20° C. for 3 hours. After completion of the reaction, the mixture was returned to room temperature and diluted with ethyl ether, and the product was subjected to filtration. Crystals were dried to obtain crude lithium 4-chloro-2-methyl-2H-indazole-3-sulfinate. This product was used for the subsequent reaction without purification.

45.2 g (0.4 mol) of hydroxylamine-O-sulfonic acid was gradually added to a solution containing 16 g (0.4 mol) of sodium hydroxide in water (300 ml) under cooling with ice (<10° C.). This solution was added all at once to a solution of the previously prepared crude lithium 4-chloro-2-methyl-2H-indazole-3-sulfinate in water (100 ml). The mixture was stirred at room temperature for 12 hours. Formed crystals were collected by filtration to obtain 17.1 g (yield: 69.8%) of the desired 4-chloro-2-methyl-2H-indazole-3-sulfonamide (slightly yellow granular crystals). Melting point: 173°–175° C.

PREPARATION EXAMPLE 12

Preparation of 1-(4-chloro-2-methyl-2H-indazole-3-sulfonyl)-3-(4,6-dimethoxypyrimidin-2-yl)urea (Compound No. II-134)

0.5 g (3.3 mmol) of DBU was added to a solution containing 0.8 g (3.3 mmol) of 4-chloro-2-methyl-2H-indazole-3-sulfonamide obtained in Preparation Example 11 and 0.9 g (3.3 mmol) of phenyl (4,6-dimethoxypyrimidin-2-yl)carbamate in acetonitrile (50 ml), and the mixture was stirred at room temperature for 12 hours. The mixture was poured into ice water and acidified with citric acid. Formed crystals were collected by filtration and sequentially washed with water, isopropyl ether and ethyl ether, to obtain 1.2 g (yield: 85%) of the desired product (colorless needle-like crystals). Melting point: 171°–172° C.

The herbicide of the present invention contains an indazolesulfonylurea derivative represented by the general formula [I] or [II] as an active ingredient.

For the compound of the present invention to be used as a herbicide, the compound of the present invention may be used by itself. However, it may be used in the form of a formulation such as a dust, a wettable powder, an emulsifiable concentrate, a microgranule or a granule by blending it with a carrier, a surfactant, a dispersant or an adjuvant which is commonly used for formulations.

The carrier to be used for such formulations, may, for example, be a solid carrier such as Zeeklite, talc, bentonite, clay, kaolin, diatomaceous earth, fine silica, vermiculite, calcium carbonate, slaked lime, silica sand, ammonium sulfate or urea, or a liquid carrier such as isopropyl alcohol, xylene, cyclohexane or methylnaphthalene.

As the surfactant and dispersant, a metal salt of alkylbenzenesulfonic acid, a metal salt of dinaphthylmethane disulfonic acid, a salt of alcohol-sulfuric acid ester, an alkylaryl sulfonate, a lignin sulfonate, a polyoxyethylene glycol ether, a polyoxyethylene alkylaryl ether or a polyoxyethylene sorbitol monoalkylate may, for example, be mentioned.

The adjuvant may, for example, be carboxymethyl cellulose, polyethylene glycol or gum arabic.

In practical use, the herbicide may be diluted to a suitable concentration before application, or may be directly applied.

The herbicide of the present invention may be used for application to foliage, soil or water surface. The blending proportion of the active ingredient is suitably selected as the case requires. However, in a case of a dust or a granule, the proportion of the active ingredient is selected suitably within a range of from 0.01 to 10% (by weight), preferably from 0.05 to 5% (by weight). In a case of an emulsifiable concentrate or a wettable powder, the proportion is selected suitably within a range of from 1 to 50% (by weight), preferably from 5 to 30% (by weight).

The dose of the herbicide of the present invention varies depending upon the type of the compound, the weeds to be controlled, the germination tendency, the environmental conditions and the type of the formulation to be used. However, in the case of a dust or a granule which is used by itself, the dose of the active ingredient is selected suitably within a range of from 0.1 g to 5 kg, preferably from 1 g to 1 kg, per 10 ares. In a case of an emulsifiable concentrate or a wettable powder which is used in a liquid state, the dose of the active ingredient is selected suitably within a range of from 0.1 to 50,000 ppm, preferably from 10 to 10,000 ppm.

Further, the compound of the present invention may be used in combination with an insecticide, a fungicide, other herbicide, a plant growth controlling agent, a fertilizer or the like, as the case requires.

Now, the formulation method will be described with reference to typical Formulation Examples. The compounds, types of the additives and blending ratios are not limited to such specific Examples and may be changed within wide ranges. In the following description, "parts" means "parts by weight".

FORMULATION EXAMPLE 1

(Wettable powder)

To 10 parts of Compound No. I-9 or II-26, 0.5 part of polyoxyethyleneoctylphenyl ether, 0.5 part of sodium β-naphthalene sulfonate-formalin condensate, 20 parts of diatomaceous earth and 69 parts of clay were mixed and pulverized to obtain a wettable powder.

FORMULATION EXAMPLE 2

(Wettable powder)

To 10 parts of Compound No. I-63 or II-134, 0.5 part of polyoxyethyleneoctylphenyl ether, 0.5 part of sodium β-naphthalene sulfonate-formalin condensate, 20 parts of diatomaceous earth, 5 parts of fine silica and 64 parts of clay were mixed and pulverized to obtain a wettable powder.

FORMULATION EXAMPLE 3

(Wettable powder)

To 10 parts of Compound No. I-134 or II-104, 0.5 part of polyoxyethyleneoctylphenyl ether, 0.5 part of sodium β-naphthalene sulfonate-formalin condensate, 20 parts of diatomaceous earth, 5 parts of fine silica and 64 parts of calcium carbonate, were mixed and pulverized to obtain a wettable powder.

FORMULATION EXAMPLE 4

(Emulsifiable concentrate)

To parts of Compound No. I-92 or II-64, 60 parts of a mixture comprising equal amounts of xylene and isophorone and 10 parts of a mixture comprising a polyoxyethylene sorbitol alkylate surfactant, a polyoxyethylenealkylaryl polymer and an alkylaryl sulfonate, were added, and the mixture was thoroughly stirred to obtain an emulsifiable concentrate.

FORMULATION EXAMPLE 5

(Granule)

10 Parts of Compound No. I-64 or II-142, 80 parts of a bulking agent comprising a 1:3 mixture of talc and bentonite, 5 parts of fine silica, 5 parts of a mixture comprising a polyoxyethylene sorbitol alkylate surfactant, a polyoxyethylenealkylaryl polymer and an alkylaryl sulfonate and 10 parts of water were mixed and thoroughly kneaded to obtain a paste, which was extruded from sieve apertures with a diameter of 0.7 mm. The extruded product was dried and then cut into a length of from 0.5 to 1 mm to obtain granules.

The compound of the present invention represented by the general formula [I] or [II] is capable of controlling annual weeds such as barnyardgrass (*Echinochloa oryzicola*), smallflower umbrella-plant (*Cyperus difformis*) and monochoria (*Monochoria vaginalis*) as well as perennial weeds such as Japanese ribbon wapato (*Sagittaria pygmaea*), arrowhead (*Sagittaria trifolia*), water nutgrass (*Cyperus serotinus*), water chestnut (*Eleocharis kuroguwai*), bulrush (*Scirpus juncoides*) and narrow-leaved arrowhead (*Alisma canaliculatum*), which germinate in paddy fields. Further, it exhibits excellent herbicidal effects against various weeds problematic in upland fields, including broadleaf weeds such as smartweed (*Polygonum lapathifolium*), green amaranth (*Amaranthus viridis*), lambsquater (*Chenopodium album*), goose grass (*Galium aparine*), chickweed (*Stellaria media*), velvetleaf (*Abtilon theophrasti*), prickly sida (*Sida spinosa*), hemp sesbania (*Sesbania exaltata*), morningglory (*Ipomoea* spp) and common cocklebur (*Xanthium strumarium*), perennial and annual syperaceous weeds such as purple nutsedge (*Cyperus rotundus*), yellow nutsedge (*Cyperus esculentus*), himekugu (*Cyperus brevifolius var. leiolepis*), annual sedge (*Cyperus microiria*) and rice flatsedge (*Cyperus iria*), and gramineous weeds such as barnyardgrass (*Echinochloa crus-galli*), goosegrass (*Eleusine indica*), greenfoxtail (*Setaria viridis*), annual bluegrass (*Poa annua*), johnsongrass (*Sorghum halepense*), water foxtail (*Alopecurus aequalis*) and wild oat (*Avena fatua*), over a wide range from the preemergence stage to the growing stage.

On the other hand, the herbicide of the present invention is highly safe to crop plants and exhibits particularly high safety to e.g. rice, wheat, barley, corn, grain sorghum and sugar beat.

Now, the effects of the compounds of the present invention will be described with reference to Test Examples.

TEST EXAMPLE 1

(Test on herbicidal effects by paddy field soil treatment)

In a plastic pot (surface area: 100 cm$^2$) filled with paddy field soil, barnyardgrass (Ec), monochoria (Mo) and bulrush (Sc) were sown after puddling and leveling, and flooded to a water depth of 3 cm. Next day, a wettable powder prepared in accordance with Formulation Example 1 was diluted with water and applied dropwise to the water surface. The dose was 100 g of the active ingredient per 10 ares. The plants were then cultured in a green house, and the evaluation of the herbicidal effects was conducted on the 21st day after the application in accordance with the standards as identified in Table 4. The results are shown in Table 5.

TABLE 4

| Index No. | Herbicidal effects (growth-controlling degree) or phytotoxicity |
|---|---|
| 5 | Herbicidal effect or phytotoxicity: at least 90% |
| 4 | Herbicidal effect or phytotoxicity: at least 70% and less than 90% |
| 3 | Herbicidal effect or phytotoxicity: at least 50% and less than 70% |
| 2 | Herbicidal effect or phytotoxicity: at least 30% and less than 50% |
| 1 | Herbicidal effect or phytotoxicity: at least 10 and less than 30% |
| 0 | Herbicidal effect or phytotoxicity: 0 to less than 10% |

TABLE 5

| Compound No. | Herbicidal effects Ec | Mo | Sc |
|---|---|---|---|
| I-5 | 5 | 5 | 5 |
| I-6 | 5 | 5 | 5 |
| I-8 | 5 | 5 | 5 |
| I-17 | 5 | 5 | 5 |
| I-18 | 5 | 5 | 5 |
| I-19 | 5 | 5 | 5 |
| I-20 | 5 | 5 | 5 |
| I-23 | 5 | 5 | 5 |
| I-25 | 5 | 5 | 5 |
| I-26 | 5 | 5 | 5 |
| I-27 | 5 | 5 | 5 |
| I-28 | 5 | 5 | 5 |
| I-29 | 5 | 5 | 5 |
| I-31 | 5 | 5 | 5 |
| I-32 | 5 | 5 | 5 |
| I-33 | 5 | 5 | 5 |
| I-34 | 5 | 5 | 5 |
| I-35 | 5 | 5 | 5 |
| I-63 | 5 | 5 | 5 |
| I-64 | 5 | 5 | 5 |
| I-65 | 5 | 5 | 5 |
| I-66 | 5 | 5 | 5 |
| I-67 | 5 | 5 | 5 |
| I-79 | 5 | 5 | 5 |
| I-91 | 5 | 5 | 5 |
| I-92 | 5 | 5 | 5 |
| I-93 | 5 | 5 | 5 |
| I-94 | 5 | 5 | 5 |
| I-95 | 5 | 5 | 5 |
| I-111 | 5 | 5 | 5 |
| I-114 | 5 | 5 | 5 |
| I-120 | 5 | 5 | 5 |
| I-131 | 5 | 5 | 5 |
| I-134 | 5 | 5 | 5 |
| I-136 | 5 | 5 | 5 |
| I-149 | 5 | 5 | 5 |
| I-150 | 5 | 5 | 5 |
| I-151 | 5 | 5 | 4 |
| I-153 | 5 | 5 | 5 |
| I-157 | 5 | 5 | 5 |
| I-158 | 5 | 5 | 5 |
| I-160 | 5 | 5 | 5 |
| I-161 | 5 | 5 | 5 |
| I-162 | 5 | 5 | 5 |
| I-174 | 5 | 5 | 5 |
| I-175 | 5 | 5 | 5 |
| I-176 | 5 | 5 | 5 |
| I-179 | 5 | 5 | 5 |
| I-180 | 5 | 5 | 5 |
| I-181 | 5 | 5 | 5 |

TABLE 5-continued

| Compound No. | Herbicidal effects | | |
|---|---|---|---|
| | Ec | Mo | Sc |
| I-182 | 5 | 5 | 5 |
| I-183 | 5 | 5 | 5 |
| I-184 | 5 | 5 | 5 |
| I-194 | 5 | 5 | 5 |
| I-204 | 5 | 5 | 5 |
| I-205 | 5 | 5 | 5 |
| I-216 | 5 | 5 | 5 |
| I-218 | 5 | 5 | 4 |
| I-322 | 5 | 5 | 5 |
| I-334 | 5 | 5 | 5 |
| I-337 | 5 | 5 | 5 |
| I-506 | 5 | 5 | 5 |
| I-507 | 5 | 5 | 5 |
| I-508 | 4 | 5 | 4 |
| I-513 | 5 | 5 | 5 |
| I-514 | 5 | 5 | 5 |
| I-516 | 5 | 5 | 5 |
| I-517 | 5 | 5 | 5 |
| I-518 | 5 | 5 | 5 |
| I-519 | 5 | 5 | 4 |
| I-520 | 3 | 5 | 5 |
| I-527 | 3 | 5 | 5 |
| I-530 | 5 | 5 | 5 |
| I-555 | 5 | 5 | 4 |
| I-641 | 5 | 5 | 5 |
| I-645 | 3 | 5 | 5 |
| I-906 | 3 | 5 | 5 |
| II-5 | 5 | 5 | 5 |
| II-6 | 5 | 5 | 5 |
| II-8 | 5 | 5 | 5 |
| II-17 | 5 | 5 | 5 |
| II-18 | 4 | 5 | 4 |
| II-19 | 5 | 5 | 5 |
| II-20 | 5 | 5 | 5 |
| II-23 | 5 | 5 | 5 |
| II-25 | 5 | 5 | 5 |
| II-26 | 5 | 5 | 5 |
| II-27 | 5 | 5 | 5 |
| II-28 | 5 | 5 | 5 |
| II-29 | 5 | 5 | 5 |
| II-31 | 5 | 5 | 5 |
| II-32 | 5 | 5 | 5 |
| II-33 | 5 | 5 | 5 |
| II-34 | 5 | 5 | 5 |
| II-35 | 5 | 5 | 5 |
| II-36 | 5 | 5 | 5 |
| II-38 | 5 | 5 | 5 |
| II-42 | 4 | 5 | 5 |
| II-53 | 5 | 5 | 5 |
| II-55 | 5 | 5 | 5 |
| II-63 | 5 | 5 | 5 |
| II-64 | 5 | 5 | 5 |
| II-65 | 5 | 5 | 5 |
| II-66 | 5 | 5 | 5 |
| II-67 | 5 | 5 | 5 |
| II-91 | 5 | 5 | 5 |
| II-92 | 5 | 5 | 5 |
| II-93 | 5 | 5 | 5 |
| II-94 | 5 | 5 | 5 |
| II-95 | 5 | 5 | 5 |
| II-104 | 5 | 5 | 5 |
| II-106 | 5 | 5 | 5 |
| II-107 | 5 | 5 | 5 |
| II-110 | 5 | 5 | 5 |
| II-111 | 5 | 5 | 5 |
| II-112 | 5 | 5 | 5 |
| II-113 | 5 | 5 | 5 |
| II-114 | 5 | 5 | 5 |
| II-115 | 5 | 5 | 5 |
| II-120 | 5 | 5 | 5 |
| II-127 | 5 | 5 | 5 |
| II-129 | 4 | 5 | 5 |
| II-130 | 5 | 5 | 5 |
| II-131 | 5 | 5 | 5 |
| II-132 | 3 | 5 | 5 |
| II-134 | 5 | 5 | 5 |
| II-136 | 3 | 5 | 5 |
| II-137 | 5 | 5 | 5 |
| II-141 | 5 | 5 | 5 |
| II-142 | 5 | 5 | 5 |
| II-143 | 5 | 5 | 5 |
| II-149 | 5 | 5 | 5 |
| II-150 | 5 | 5 | 5 |
| II-151 | 5 | 5 | 5 |
| II-153 | 5 | 5 | 5 |
| II-155 | 5 | 5 | 5 |
| II-156 | 5 | 5 | 5 |
| II-157 | 5 | 5 | 5 |
| II-158 | 5 | 5 | 5 |
| II-159 | 5 | 5 | 5 |
| II-160 | 5 | 5 | 5 |
| II-161 | 5 | 5 | 5 |
| II-162 | 5 | 5 | 5 |
| II-163 | 5 | 5 | 5 |
| II-166 | 5 | 5 | 5 |
| II-168 | 5 | 5 | 5 |
| II-169 | 5 | 5 | 5 |
| II-174 | 5 | 5 | 5 |
| II-175 | 5 | 5 | 5 |
| II-176 | 5 | 5 | 5 |
| II-177 | 5 | 5 | 5 |
| II-178 | 5 | 5 | 5 |
| II-179 | 5 | 5 | 5 |
| II-180 | 5 | 5 | 5 |
| II-181 | 5 | 5 | 5 |
| II-182 | 5 | 5 | 5 |
| II-183 | 5 | 5 | 5 |
| II-184 | 5 | 5 | 5 |
| II-185 | 5 | 5 | 5 |
| II-188 | 5 | 5 | 5 |
| II-189 | 5 | 5 | 5 |
| II-194 | 5 | 5 | 5 |
| II-195 | 5 | 5 | 5 |
| II-197 | 5 | 5 | 5 |
| II-198 | 5 | 5 | 5 |
| II-199 | 5 | 5 | 5 |
| II-200 | 5 | 5 | 5 |
| II-202 | 4 | 5 | 5 |
| II-204 | 5 | 5 | 5 |
| II-208 | 5 | 5 | 5 |
| II-215 | 5 | 5 | 5 |
| II-220 | 5 | 5 | 5 |
| II-225 | 5 | 5 | 5 |
| II-227 | 5 | 5 | 5 |
| II-531 | 5 | 5 | 5 |

TEST EXAMPLE 2

(Test on herbicidal effects by upland field soil treatment)

In a plastic pot (surface area: 120 cm$^2$) filled with upland field soil, pale smartweed (Pc), slender amaranth (Am), common lambsquarters (Ch) and rice flatsedge (Ci) were sown and covered with soil. A wettable powder prepared in accordance with Formulation Example 1 was diluted with water and applied uniformly to the soil surface by a small-sized sprayer in an amount of 100 l/10 ares so as to apply 100 g of the active ingredient per 10 ares. The plants were then cultured in a green house, and the evaluation of the herbicidal effects was conducted on the 21st day after the application in accordance with the standards as identified in Table 4. The results are shown in Table 6.

TABLE 6

| Compound No. | Herbicidal effects | | | |
|---|---|---|---|---|
| | Po | Am | Ch | Ci |
| I-5 | 5 | 5 | 5 | 5 |
| I-6 | 5 | 5 | 5 | 5 |
| I-8 | 5 | 5 | 5 | 5 |
| I-17 | 5 | 5 | 5 | 5 |
| I-18 | 5 | 5 | 5 | 5 |
| I-19 | 5 | 5 | 5 | 5 |
| I-20 | 5 | 5 | 5 | 5 |
| I-23 | 5 | 5 | 5 | 5 |
| I-25 | 5 | 5 | 5 | — |
| I-26 | 5 | 5 | 5 | — |
| I-27 | 5 | 5 | 5 | 5 |
| I-28 | 5 | 5 | 5 | 5 |
| I-29 | 5 | 5 | 5 | — |
| I-31 | 5 | 5 | 5 | — |
| I-32 | 5 | 5 | 5 | 5 |
| I-33 | 5 | 5 | 5 | 5 |
| I-34 | 5 | 5 | 5 | 5 |
| I-35 | 5 | 5 | 5 | 5 |
| I-53 | 5 | 5 | 5 | 5 |
| I-63 | 5 | 5 | 5 | 5 |
| I-64 | 5 | 5 | 5 | 5 |
| I-65 | 5 | 5 | 5 | 5 |
| I-66 | 5 | 5 | 5 | 5 |
| I-67 | 5 | 5 | 5 | 5 |
| I-79 | 5 | 5 | 5 | 5 |
| I-91 | 5 | 5 | 5 | 5 |
| I-92 | 5 | 5 | 5 | 5 |
| I-93 | 5 | 5 | 5 | 5 |
| I-94 | 5 | 5 | 5 | 5 |
| I-95 | 5 | 5 | 5 | 5 |
| I-110 | 5 | 5 | 5 | 5 |
| I-111 | 5 | 5 | 5 | 5 |
| I-112 | 5 | 5 | 5 | 5 |
| I-113 | 5 | 5 | 5 | 5 |
| I-114 | 5 | 5 | 5 | 5 |
| I-120 | 5 | 5 | 5 | 5 |
| I-131 | 5 | 5 | 5 | 5 |
| I-134 | 5 | 5 | 5 | 5 |
| I-136 | 5 | 5 | 5 | 5 |
| I-149 | 5 | 5 | 5 | 5 |
| I-150 | 5 | 5 | 5 | 5 |
| I-151 | 5 | 5 | 5 | 5 |
| I-152 | 5 | 5 | 4 | 5 |
| I-153 | 5 | 5 | 5 | 5 |
| I-157 | 5 | 5 | 5 | 5 |
| I-158 | 5 | 5 | 5 | 5 |
| I-160 | 5 | 5 | 5 | 5 |
| I-161 | 5 | 5 | 5 | 5 |
| I-162 | 5 | 5 | 5 | 5 |
| I-174 | 5 | 5 | 5 | 5 |
| I-175 | 5 | 5 | 5 | 5 |
| I-176 | 5 | 5 | 5 | — |
| I-177 | 5 | 5 | 5 | — |
| I-178 | 5 | 5 | 5 | 5 |
| I-179 | 5 | 5 | 5 | — |
| I-180 | 5 | 5 | 5 | 5 |
| I-181 | 5 | 5 | 5 | 5 |
| I-182 | 5 | 5 | 5 | 5 |
| I-183 | 5 | 5 | 4 | 5 |
| I-184 | 5 | 5 | 5 | 5 |
| I-194 | 5 | 5 | 5 | 5 |
| I-198 | 5 | 5 | 5 | 5 |
| I-199 | 5 | 5 | 5 | 5 |
| I-204 | 5 | 5 | 5 | 5 |
| I-205 | 5 | 5 | 4 | 5 |
| I-209 | 5 | 5 | 4 | 5 |
| I-212 | 5 | 5 | 5 | 5 |
| I-216 | 5 | 5 | 5 | 5 |
| I-218 | 4 | 5 | 4 | 5 |
| I-322 | 5 | 5 | 5 | — |
| I-334 | 5 | 5 | 5 | — |
| I-337 | 5 | 5 | 5 | — |
| I-506 | 5 | 5 | 5 | 5 |
| I-507 | 5 | 5 | 5 | 5 |
| I-508 | 5 | 5 | 5 | 5 |

TABLE 6-continued

| Compound No. | Herbicidal effects | | | |
|---|---|---|---|---|
| | Po | Am | Ch | Ci |
| I-509 | 5 | 5 | 4 | 5 |
| I-511 | 5 | 5 | 5 | 4 |
| I-513 | 5 | 5 | 5 | 5 |
| I-514 | 5 | 5 | 5 | 4 |
| I-516 | 5 | 5 | 5 | 5 |
| I-517 | 4 | 5 | 4 | 5 |
| I-518 | 5 | 5 | 5 | 5 |
| I-519 | 5 | 5 | 5 | 5 |
| I-520 | 5 | 5 | 5 | 5 |
| I-521 | 5 | 5 | 5 | 5 |
| I-525 | 5 | 5 | 5 | 5 |
| I-526 | 4 | 5 | 4 | 5 |
| I-527 | 5 | 5 | 5 | 5 |
| I-528 | 5 | 5 | 5 | 5 |
| I-529 | 4 | 5 | 5 | 5 |
| I-530 | 5 | 5 | 5 | 5 |
| I-555 | 5 | 5 | 5 | 5 |
| I-641 | 5 | 5 | 5 | 5 |
| I-645 | 5 | 5 | 5 | 5 |
| I-761 | 4 | 5 | 4 | — |
| I-905 | 5 | 5 | 5 | — |
| I-906 | 5 | 5 | 5 | — |
| II-5 | 5 | 5 | 5 | 5 |
| II-6 | 5 | 5 | 4 | 5 |
| II-8 | 5 | 5 | 5 | 5 |
| II-17 | 5 | 5 | 5 | 5 |
| II-19 | 5 | 5 | 5 | 5 |
| II-20 | 5 | 5 | 5 | 5 |
| II-23 | 5 | 5 | 5 | 5 |
| II-25 | 5 | 5 | 4 | 5 |
| II-26 | 5 | 5 | 5 | 5 |
| II-27 | 5 | 5 | 5 | 5 |
| II-28 | 5 | 5 | 5 | 5 |
| II-29 | 5 | 5 | 5 | — |
| II-31 | 5 | 5 | 5 | 5 |
| II-32 | 5 | 5 | 5 | 5 |
| II-34 | 5 | 5 | 5 | 5 |
| II-35 | 5 | 5 | 5 | 5 |
| II-36 | 5 | 5 | 5 | 5 |
| II-38 | 5 | 5 | 4 | 5 |
| II-53 | 5 | 5 | 5 | — |
| II-55 | 5 | 5 | 4 | 5 |
| II-56 | 5 | 5 | 5 | 5 |
| II-63 | 5 | 5 | 5 | 5 |
| II-64 | 5 | 5 | 5 | 5 |
| II-65 | 5 | 5 | 5 | — |
| II-66 | 5 | 5 | 5 | — |
| II-67 | 5 | 5 | 5 | — |
| II-90 | 4 | 5 | 5 | — |
| II-91 | 5 | 5 | 5 | 5 |
| II-92 | 5 | 5 | 5 | 5 |
| II-93 | 5 | 5 | 4 | 5 |
| II-95 | 4 | 5 | 4 | 5 |
| II-96 | 5 | 5 | 4 | 5 |
| II-104 | 5 | 5 | 5 | — |
| II-105 | 4 | 5 | 5 | — |
| II-106 | 5 | 5 | 5 | 5 |
| II-107 | 5 | 5 | 5 | 5 |
| II-110 | 5 | 5 | 5 | 5 |
| II-111 | 5 | 5 | 5 | 5 |
| II-113 | 5 | 5 | 5 | 5 |
| II-114 | 5 | 5 | 5 | 5 |
| II-115 | 5 | 5 | 4 | 4 |
| II-120 | 5 | 5 | 5 | 5 |
| II-127 | 5 | 5 | 5 | 5 |
| II-130 | 5 | 5 | 4 | 5 |
| II-131 | 5 | 5 | 5 | 5 |
| II-134 | 5 | 5 | 5 | 5 |
| II-136 | 5 | 5 | 5 | 5 |
| II-137 | 5 | 5 | 5 | — |
| II-138 | 5 | 5 | 5 | — |
| II-139 | 5 | 5 | 5 | — |
| II-140 | 5 | 5 | 4 | — |
| II-141 | 5 | 5 | 5 | — |
| II-142 | 5 | 5 | 5 | — |

TABLE 6-continued

| Compound No. | Herbicidal effects | | | |
|---|---|---|---|---|
| | Po | Am | Ch | Ci |
| II-143 | 5 | 5 | 5 | — |
| II-144 | 5 | 5 | 5 | — |
| II-145 | 5 | 5 | 5 | — |
| II-146 | 5 | 5 | 5 | 5 |
| II-149 | 5 | 5 | 4 | 5 |
| II-150 | 5 | 5 | 5 | 5 |
| II-155 | 5 | 5 | 5 | 5 |
| II-156 | 4 | 5 | 5 | 5 |
| II-157 | 5 | 5 | 5 | 5 |
| II-158 | 5 | 5 | 5 | 5 |
| II-160 | 5 | 5 | 5 | 5 |
| II-161 | 4 | 5 | 5 | 5 |
| II-162 | 5 | 5 | 5 | 5 |
| II-163 | 5 | 5 | 4 | 5 |
| II-164 | 5 | 5 | 5 | 5 |
| II-166 | 5 | 5 | 5 | 5 |
| II-167 | 4 | 5 | 5 | 5 |
| II-168 | 5 | 5 | 5 | 5 |
| II-169 | 5 | 5 | 5 | 5 |
| II-170 | 4 | 5 | 5 | 5 |
| II-172 | 5 | 5 | 5 | 5 |
| II-174 | 5 | 5 | 5 | 5 |
| II-175 | 5 | 5 | 5 | — |
| II-176 | 5 | 5 | 5 | — |
| II-177 | 5 | 5 | 5 | — |
| II-178 | 5 | 5 | 5 | — |
| II-179 | 5 | 5 | 5 | — |
| II-180 | 5 | 5 | 5 | 5 |
| II-181 | 5 | 5 | 5 | 5 |
| II-182 | 5 | 5 | 5 | 5 |
| II-183 | 5 | 5 | 4 | 5 |
| II-184 | 5 | 5 | 5 | 5 |
| II-185 | 5 | 5 | 5 | — |
| II-188 | 5 | 5 | 5 | 5 |
| II-189 | 5 | 5 | 5 | 5 |
| II-191 | 5 | 5 | 5 | — |
| II-195 | 5 | 5 | 5 | 4 |
| II-197 | 5 | 5 | 5 | — |
| II-198 | 5 | 5 | 5 | — |
| II-199 | 5 | 5 | 5 | — |
| II-200 | 5 | 5 | 5 | — |
| II-204 | 5 | 5 | 4 | 5 |
| II-207 | 5 | 5 | 4 | — |
| II-219 | 4 | 5 | 5 | 5 |
| II-220 | 5 | 5 | 5 | — |
| II-223 | 5 | 5 | 5 | — |
| II-225 | 5 | 5 | 5 | 5 |
| II-226 | 5 | 5 | 5 | 5 |
| II-227 | 5 | 5 | 5 | — |
| II-531 | 5 | 5 | 5 | — |

TEST EXAMPLE 3

(Test on herbicidal effects by upland field foliage treatment)

In a plastic pot (surface area: 120 cm$^2$) filled with upland field soil, pale smartweed (Po), slender amaranth (Am), common lambsquarters (Ch) and rice flatsedge (Ci) were sown and covered with soil and were cultured in a green house for 2 weeks. A wettable powder prepared in accordance with Formulation Example 1 was diluted with water and applied onto the entire foliages of the plants from above by a small-sized sprayer in an amount of 100 l/10 ares so as to apply 100 g of the active ingredient per 10 ares. The plants were then cultured in the green house, and the evaluation of the herbicidal effects was conducted on the 14th day after the treatment in accordance with the standards as identified in Table 4. The results are shown in Table 7.

TABLE 7

| Compound No. | Herbicidal effects | | | |
|---|---|---|---|---|
| | Po | Am | Ch | Ci |
| I-5 | 5 | 5 | 5 | 5 |
| I-6 | 5 | 5 | 5 | 5 |
| I-8 | 5 | 5 | 5 | 5 |
| I-17 | 5 | 5 | 5 | 5 |
| I-18 | 5 | 5 | 5 | 5 |
| I-19 | 5 | 5 | 5 | 5 |
| I-20 | 5 | 5 | 5 | 5 |
| I-23 | 5 | 5 | 5 | 5 |
| I-25 | 5 | 5 | 5 | 5 |
| I-26 | 5 | 5 | 5 | 5 |
| I-27 | 5 | 5 | 5 | 5 |
| I-28 | 5 | 5 | 5 | 5 |
| I-29 | 5 | 5 | 5 | 5 |
| I-31 | 5 | 5 | 5 | 5 |
| I-32 | 5 | 5 | 5 | 5 |
| I-33 | 5 | 5 | 5 | 5 |
| I-34 | 5 | 5 | 5 | 5 |
| I-35 | 5 | 5 | 5 | 5 |
| I-53 | 5 | 5 | 5 | 5 |
| I-63 | 5 | 5 | 5 | 5 |
| I-64 | 5 | 5 | 5 | 5 |
| I-65 | 5 | 5 | 5 | 5 |
| I-66 | 5 | 5 | 5 | 5 |
| I-67 | 5 | 5 | 5 | 5 |
| I-79 | 5 | 5 | 5 | 5 |
| I-91 | 5 | 5 | 5 | 5 |
| I-92 | 5 | 5 | 5 | 5 |
| I-93 | 5 | 5 | 5 | 5 |
| I-94 | 5 | 5 | 5 | 5 |
| I-95 | 5 | 5 | 5 | 5 |
| I-111 | 5 | 5 | 5 | 5 |
| I-112 | 5 | 5 | 5 | 5 |
| I-113 | 5 | 5 | 5 | 5 |
| I-114 | 5 | 5 | 5 | 5 |
| I-120 | 5 | 5 | 5 | 5 |
| I-131 | 5 | 5 | 5 | 5 |
| I-134 | 5 | 5 | 5 | 5 |
| I-136 | 5 | 5 | 4 | 4 |
| I-149 | 4 | 5 | 4 | 5 |
| I-150 | 5 | 5 | 5 | 5 |
| I-151 | 5 | 5 | 5 | 5 |
| I-157 | 5 | 5 | 5 | 5 |
| I-158 | 5 | 5 | 5 | 5 |
| I-160 | 5 | 5 | 5 | 5 |
| I-161 | 5 | 5 | 5 | 5 |
| I-162 | 5 | 5 | 5 | 5 |
| I-174 | 5 | 5 | 5 | 5 |
| I-175 | 5 | 5 | 5 | 5 |
| I-176 | 5 | 5 | 5 | 5 |
| I-177 | 4 | 4 | 5 | 5 |
| I-178 | 5 | 5 | 5 | 5 |
| I-179 | 5 | 5 | 5 | 5 |
| I-180 | 5 | 5 | 5 | 5 |
| I-181 | 5 | 5 | 5 | 5 |
| I-182 | 5 | 5 | 5 | 5 |
| I-183 | 5 | 5 | 5 | 4 |
| I-184 | 5 | 5 | 5 | 5 |
| I-194 | 5 | 5 | 5 | 5 |
| I-204 | 5 | 5 | 5 | 5 |
| I-205 | 5 | 5 | 5 | 5 |
| I-206 | 5 | 5 | 5 | 4 |
| I-209 | 4 | 5 | 5 | 4 |
| I-211 | 4 | 5 | 5 | 4 |
| I-212 | 4 | 5 | 5 | 4 |
| I-216 | 5 | 5 | 5 | 5 |
| I-218 | 5 | 5 | 4 | 4 |
| I-322 | 5 | 5 | 5 | 5 |
| I-324 | 4 | 5 | 4 | 5 |
| I-334 | 5 | 5 | 4 | 5 |
| I-337 | 5 | 5 | 5 | 5 |
| I-506 | 4 | 5 | 4 | 5 |
| I-507 | 5 | 5 | 5 | 5 |
| I-508 | 5 | 5 | 5 | 5 |
| I-509 | 5 | 5 | 5 | 5 |
| I-511 | 4 | 5 | 5 | 4 |

TABLE 7-continued

| Compound No. | Herbicidal effects | | | |
|---|---|---|---|---|
| | Po | Am | Ch | Ci |
| I-513 | 5 | 5 | 5 | 5 |
| I-514 | 5 | 5 | 5 | 4 |
| I-516 | 5 | 5 | 5 | 5 |
| I-517 | 5 | 5 | 4 | 5 |
| I-518 | 5 | 5 | 5 | 5 |
| I-520 | 5 | 5 | 5 | 5 |
| I-525 | 5 | 5 | 5 | 5 |
| I-526 | 5 | 5 | 5 | 4 |
| I-527 | 5 | 5 | 5 | 5 |
| I-528 | 5 | 5 | 5 | 5 |
| I-530 | 5 | 5 | 5 | 5 |
| I-555 | 5 | 5 | 5 | 5 |
| I-641 | 5 | 5 | 5 | 5 |
| II-5 | 5 | 5 | 5 | 5 |
| II-6 | 4 | 5 | 5 | 5 |
| II-8 | 5 | 5 | 4 | 5 |
| II-17 | 5 | 5 | 4 | 5 |
| II-19 | 5 | 5 | 5 | 5 |
| II-20 | 5 | 5 | 5 | 5 |
| II-23 | 5 | 5 | 5 | 5 |
| II-25 | 5 | 5 | 5 | 5 |
| II-26 | 5 | 5 | 5 | 5 |
| II-27 | 5 | 5 | 5 | 5 |
| II-28 | 5 | 5 | 5 | 5 |
| II-29 | 5 | 5 | 5 | 5 |
| II-31 | 5 | 5 | 4 | 5 |
| II-32 | 5 | 5 | 5 | 5 |
| II-34 | 5 | 5 | 5 | 5 |
| II-35 | 5 | 5 | 5 | 5 |
| II-38 | 5 | 5 | 4 | 5 |
| II-53 | 5 | 5 | 5 | 5 |
| II-55 | 5 | 5 | 5 | 5 |
| II-56 | 5 | 5 | 5 | 5 |
| II-63 | 5 | 5 | 5 | 5 |
| II-64 | 5 | 5 | 5 | 5 |
| II-65 | 5 | 5 | 5 | 5 |
| II-66 | 5 | 5 | 5 | 5 |
| II-67 | 5 | 5 | 5 | 5 |
| II-91 | 5 | 5 | 5 | 5 |
| II-92 | 5 | 5 | 5 | 5 |
| II-93 | 5 | 5 | 5 | 5 |
| II-94 | 5 | 5 | 5 | 5 |
| II-104 | 5 | 5 | 5 | 5 |
| II-105 | 5 | 5 | 5 | 5 |
| II-106 | 5 | 5 | 5 | 5 |
| II-107 | 5 | 5 | 5 | 5 |
| II-110 | 5 | 5 | 5 | 5 |
| II-111 | 5 | 5 | 5 | 5 |
| II-112 | 5 | 5 | 5 | 5 |
| II-113 | 5 | 5 | 5 | 5 |
| II-114 | 5 | 5 | 5 | 5 |
| II-115 | 5 | 5 | 4 | 5 |
| II-120 | 5 | 5 | 5 | 5 |
| II-129 | 5 | 5 | 5 | 5 |
| II-130 | 5 | 5 | 5 | 5 |
| II-131 | 5 | 5 | 5 | 5 |
| II-134 | 5 | 5 | 5 | 5 |
| II-136 | 5 | 5 | 4 | 4 |
| II-140 | 5 | 5 | 5 | 5 |
| II-141 | 4 | 5 | 4 | 5 |
| II-142 | 5 | 5 | 5 | 5 |
| II-143 | 5 | 5 | 5 | 5 |
| II-146 | 5 | 5 | 4 | 5 |
| II-149 | 5 | 5 | 5 | 5 |
| II-150 | 5 | 5 | 5 | 5 |
| II-153 | 5 | 5 | 4 | 4 |
| II-154 | 5 | 5 | 5 | 4 |
| II-155 | 5 | 5 | 5 | 5 |
| II-157 | 5 | 5 | 5 | 5 |
| II-158 | 5 | 5 | 4 | 5 |
| II-160 | 5 | 5 | 5 | 5 |
| II-162 | 5 | 5 | 5 | 5 |
| II-166 | 5 | 5 | 5 | 5 |
| II-167 | 5 | 5 | 5 | 5 |
| II-168 | 5 | 5 | 5 | 5 |
| II-169 | 5 | 5 | 5 | 5 |
| II-170 | 4 | 5 | 5 | 5 |
| II-174 | 5 | 5 | 4 | 5 |
| II-175 | 5 | 4 | 5 | 5 |
| II-176 | 5 | 5 | 5 | 5 |
| II-178 | 5 | 5 | 5 | 5 |
| II-179 | 5 | 5 | 5 | 5 |
| II-180 | 5 | 5 | 5 | 5 |
| II-181 | 5 | 5 | 5 | 5 |
| II-182 | 5 | 5 | 5 | 5 |
| II-183 | 5 | 5 | 4 | 5 |
| II-184 | 5 | 5 | 5 | 5 |
| II-188 | 5 | 5 | 5 | 5 |
| II-189 | 5 | 5 | 4 | 5 |
| II-192 | 4 | 5 | 4 | 5 |
| II-194 | 5 | 5 | 5 | 5 |
| II-195 | 5 | 5 | 5 | 5 |
| II-196 | 4 | 5 | 4 | 5 |
| II-197 | 5 | 5 | 5 | 5 |
| II-199 | 5 | 5 | 5 | 5 |
| II-204 | 5 | 5 | 5 | 5 |
| II-218 | 5 | 5 | 5 | 4 |
| II-219 | 4 | 5 | 5 | 4 |
| II-220 | 5 | 5 | 4 | 5 |
| II-225 | 5 | 5 | 5 | 5 |
| II-226 | 5 | 5 | 5 | 5 |
| II-531 | 5 | 5 | 5 | 5 |

TEST EXAMPLE 4

(Test on crop plant selectivity by paddy field soil treatment)

In a 1/10,000a plastic pot, paddy field soil was filled, irrigated, paddled and leveled. Then, barnyardgrass (Ec), monochoria (Mo) and bulrush (Sc) were sown at a depth of 0.5 cm. Further, two seedlings of rice (Or) of 2 leaf stage was transplanted at a transplantation depth of 2 cm. Then, the pot was flooded to a water depth of 3 cm. Next day, a prescribed amount of the active ingredient ($g^{ai}/10a$) of a wettable powder prepared in accordance with Formulation Example 1 was diluted with water and applied dropwise to the water surface. The plants were then cultured in a green house, and the evaluation of the herbicidal effects and phytotoxicity was conducted on the 28th day after the application in accordance with the standards as identified in Table 4. The results are shown in Table 8.

TABLE 8

| Compound No. | Dose (gai 10a) | Herbicidal effects | | | Phytotoxicity |
|---|---|---|---|---|---|
| | | Eo | Mo | Sc | Or |
| I-17 | 25 | 4 | 5 | 5 | 0 |
| I-157 | 6.3 | 5 | 5 | 5 | 1 |
| I-161 | 25 | 5 | 5 | 5 | 0 |
| I-174 | 25 | 5 | 5 | 4 | 1 |
| I-216 | 25 | 4 | 5 | 4 | 2 |
| II-19 | 25 | 5 | 5 | 5 | 0 |
| | 6.3 | 5 | 5 | 5 | 0 |
| II-23 | 25 | 4 | 5 | 5 | 0 |
| II-26 | 25 | 5 | 5 | 5 | 1 |
| | 6.3 | 5 | 5 | 5 | 0 |
| | 1.6 | 5 | 5 | 4 | 0 |
| II-27 | 25 | 5 | 5 | 5 | 0 |
| | 6.3 | 5 | 5 | 5 | 0 |
| II-29 | 6.3 | 5 | 5 | 5 | 1 |

TABLE 8-continued

| Compound No. | Dose (gai 10a) | Herbicidal effects | | | Phytotoxicity |
|---|---|---|---|---|---|
| | | Eo | Mo | Sc | Or |
| | 1.6 | 3 | 5 | 5 | 0 |
| II-31 | 6.3 | 5 | 5 | 5 | 1 |
| | 1.6 | 5 | 5 | 5 | 0 |
| II-35 | 25 | 5 | 5 | 5 | 1 |
| | 6.3 | 5 | 5 | 5 | 0 |
| II-36 | 25 | 5 | 5 | 5 | 0 |
| II-53 | 25 | 5 | 5 | 5 | 0 |
| II-64 | 25 | 5 | 5 | 5 | 0 |
| | 6.3 | 5 | 5 | 5 | 0 |
| II-65 | 25 | 5 | 5 | 5 | 0 |
| | 6.3 | 5 | 5 | 5 | 0 |
| II-66 | 25 | 5 | 5 | 5 | 1 |
| | 6.3 | 5 | 5 | 5 | 0 |
| II-92 | 25 | 5 | 5 | 5 | 2 |
| | 6.3 | 5 | 5 | 5 | 0 |
| | 1.6 | 5 | 5 | 5 | 0 |
| II-93 | 25 | 5 | 5 | 5 | 1 |
| | 6.3 | 5 | 5 | 5 | 0 |
| II-94 | 25 | 5 | 5 | 5 | 1 |
| | 6.3 | 5 | 5 | 5 | 0 |
| II-104 | 25 | 5 | 5 | 5 | 0 |
| | 6.3 | 5 | 5 | 5 | 0 |
| II-114 | 6.3 | 5 | 5 | 5 | 1 |
| | 1.6 | 5 | 5 | 5 | 0 |
| II-127 | 25 | 5 | 5 | 5 | 1 |
| | 6.3 | 3 | 5 | 5 | 0 |
| II-134 | 25 | 5 | 5 | 5 | 0 |
| | 6.3 | 5 | 5 | 5 | 0 |
| II-137 | 25 | 5 | 5 | 5 | 2 |
| | 6.3 | 5 | 5 | 5 | 0 |
| | 1.6 | 5 | 5 | 5 | 0 |
| II-141 | 25 | 5 | 5 | 5 | 1 |
| | 6.3 | 5 | 5 | 4 | 0 |
| II-142 | 6.3 | 5 | 5 | 5 | 0 |
| | 1.6 | 5 | 5 | 5 | 0 |
| II-157 | 25 | 5 | 5 | 5 | 0 |
| | 6.3 | 5 | 5 | 5 | 0 |
| II-160 | 25 | 5 | 5 | 5 | 0 |
| | 6.3 | 5 | 5 | 5 | 0 |
| II-162 | 25 | 5 | 5 | 5 | 1 |
| | 6.3 | 5 | 5 | 5 | 0 |
| II-166 | 1.6 | 5 | 5 | 5 | 0 |
| II-178 | 25 | 5 | 5 | 5 | 0 |
| | 6.3 | 4 | 5 | 4 | 0 |
| II-208 | 25 | 5 | 5 | 5 | 0 |
| | 6.3 | 4 | 5 | 4 | 0 |
| II-531 | 25 | 5 | 5 | 5 | 0 |
| | 6.3 | 5 | 5 | 4 | 0 |
| Comparative compound A | 25 | 5 | 5 | 5 | 5 |
| | 6.3 | 5 | 5 | 4 | 5 |
| | 1.6 | 3 | 4 | 2 | 5 |

Comparative compound A: Disclosed in Japanese Unexamined Patent Publication No. 95091/1992 (Compound No. 1)

TEST EXAMPLE 5

(Test on crop plant selectivity by upland field soil treatment)

In a plastic pot (surface area: 600 cm²) filled with upland field soil, seeds or tubers of wheat (Tr), corn (Ze), grain sorghum (Gs), pale smartweed (Po), slender amaranth (Am), common lambsquarters (Ch), velvetleaf (Ab), morningglory (Ip), cocklebur (Xa) and purple nutsedge (CR) were planted and covered with soil. Next day, a prescribed amount of the active ingredient (g$^{ai}$/10a) of a wettable powder prepared in accordance with Formulation Example 1 was diluted with water and applied uniformly to the soil surface by a small-sized sprayer in an amount of 100 l per 10 ares. The plants were then cultured in a green house, and the evaluation of the herbicidal effects was conducted on the 21st day after the application in accordance with the standards as identified in Table 4. The results are shown in Table 9.

TABLE 9

| Compound No. | Dose (gai 10a) | Herbicidal effects | | | | | | | Phytotoxicity | | |
|---|---|---|---|---|---|---|---|---|---|---|---|
| | | Po | Am | Ch | Ab | Ip | Xa | CR | Tr | Ze | Gs |
| II-19 | 25 | 5 | 5 | 5 | 5 | 5 | 5 | 2 | 0 | 1 | 0 |
| II-23 | 25 | 5 | 5 | 5 | 5 | 5 | 5 | 5 | 0 | 3 | 1 |
| | 6.3 | 4 | 5 | 4 | 5 | 5 | 5 | 5 | 0 | 3 | 0 |
| II-26 | 25 | 5 | 5 | 5 | 5 | 5 | 5 | — | 1 | 4 | 3 |
| | 6.3 | 5 | 5 | 4 | 4 | 4 | 4 | 4 | 0 | 3 | 1 |
| II-28 | 25 | 5 | 5 | 5 | 5 | 5 | 5 | — | 0 | 1 | 0 |
| | 6.3 | 5 | 5 | 4 | 4 | 4 | 4 | 4 | 0 | 0 | 0 |
| II-29 | 25 | 5 | 5 | 5 | 5 | 5 | 5 | 5 | 0 | 3 | 3 |
| | 6.3 | 5 | 5 | 5 | 5 | 5 | 5 | 5 | 0 | 1 | 1 |
| II-35 | 6.3 | 5 | 5 | 5 | 4 | 4 | 4 | 5 | 0 | 1 | 0 |
| II-53 | 25 | 5 | 5 | 5 | 5 | 5 | 5 | 5 | 1 | 2 | 1 |
| | 6.3 | 5 | 5 | 5 | 5 | 5 | 5 | 4 | 0 | 0 | 0 |
| II-63 | 25 | 5 | 5 | 5 | 5 | 5 | 5 | 5 | 0 | 5 | 3 |
| | 6.3 | 5 | 5 | 5 | 5 | 5 | 5 | 5 | 0 | 3 | 2 |
| II-64 | 6.3 | 5 | 5 | 5 | 5 | 5 | 5 | 5 | 0 | 1 | 3 |
| | 1.6 | 5 | 5 | 3 | 5 | 5 | 5 | 5 | 0 | 0 | 0 |
| II-65 | 25 | 5 | 5 | 5 | 5 | 5 | 5 | 5 | 1 | 1 | 4 |
| | 6.3 | 5 | 5 | 5 | 4 | 4 | 5 | 5 | 0 | 0 | 3 |
| II-66 | 25 | 5 | 5 | 5 | 5 | 5 | 5 | 5 | 0 | 4 | 4 |
| | 6.3 | 5 | 5 | 5 | 5 | 4 | 5 | 5 | 0 | 1 | 3 |
| II-91 | 6.3 | 5 | 5 | 5 | 5 | 5 | 5 | 5 | 0 | 4 | 1 |
| II-104 | 25 | 5 | 5 | 5 | 5 | 5 | 5 | 5 | 0 | 4 | 3 |
| | 6.3 | 5 | 5 | 4 | 4 | 5 | 4 | 5 | 0 | 1 | 3 |
| II-107 | 25 | 5 | 5 | 5 | 5 | 5 | 5 | 5 | 0 | 4 | 4 |
| | 6.3 | 5 | 5 | 4 | 3 | 5 | 5 | 5 | 0 | 3 | 3 |
| II-134 | 25 | 5 | 5 | 5 | 5 | 5 | 5 | 5 | 1 | 1 | 1 |
| | 6.3 | 5 | 5 | 5 | 5 | 5 | 5 | 5 | 0 | 0 | 0 |
| II-137 | 25 | 5 | 5 | 5 | 5 | 5 | 5 | 5 | 0 | 4 | 2 |
| | 6.3 | 5 | 5 | 5 | 4 | 5 | 5 | 5 | 0 | 3 | 1 |
| II-142 | 25 | 5 | 5 | 5 | 5 | 5 | 5 | 5 | 1 | 4 | 4 |
| | 6.3 | 5 | 5 | 5 | 5 | 5 | 5 | 5 | 0 | 3 | 3 |
| II-157 | 25 | 5 | 5 | 5 | 5 | 5 | 5 | 4 | 2 | 4 | 0 |
| | 6.3 | 5 | 5 | 5 | 3 | 5 | 3 | 3 | 0 | 1 | 0 |
| II-168 | 25 | 5 | 5 | 5 | 5 | 5 | 5 | 4 | 1 | 4 | 4 |
| | 6.3 | 5 | 5 | 5 | 4 | 4 | 5 | 3 | 0 | 3 | 3 |
| II-215 | 25 | 5 | 5 | 5 | 4 | 5 | 5 | 5 | 1 | 2 | 1 |

TEST EXAMPLE 5

(Test on crop plant selectivity by upland field foliage treatment)

In a plastic pot (surface area: 600 cm²) filled with upland field soil, seeds or tubers of wheat (Tr), corn (Ze), grain sorghum (Gs), pale smartweed (Po), slender amaranth (Am), common lambsquarters (Ch), velvetleaf (Ab), morningglory (Ip), cocklebur (Xa) and purple nutsedge (CR) were planted, covered with soil and cultured in a green house for 2 weeks. Then, a prescribed amount of the active ingredient (g$^{ai}$/10a) of a wettable powder prepared in accordance with Formulation Example 1 was diluted with water and applied onto the entire foliages of the plants from above by a small-sized sprayer in an amount of 100 l per 10 ares. The plants were then cultured in a green house, and the evaluation of the herbicidal effects was conducted on the 14th day after the treatment in accordance with the standards as identified in Table 4. The results are shown in Table 10.

TABLE 10

| Compound No. | Dose (gai 10a) | Herbicidal effects |||||| Phytotoxicity |||
|---|---|---|---|---|---|---|---|---|---|---|
| | | Po | Am | Ch | Ab | Ip | Xa | CR Tr | Ze | Gs |
| I-20 | 6.3 | 5 | 5 | 5 | 5 | 5 | 5 | 3 1 | 3 | 3 |
| I-23 | 25 | 5 | 5 | 5 | 5 | 5 | 5 | 2 0 | 4 | 3 |
| | 6.3 | 5 | 5 | 5 | 5 | 5 | 5 | 0 0 | 3 | 3 |
| I-26 | 1.6 | 5 | 5 | 5 | 5 | 5 | 5 | 1 4 | 4 | 4 |
| I-27 | 6.3 | 5 | 5 | 5 | 5 | 5 | 5 | 3 1 | 3 | 3 |
| | 1.6 | 5 | 5 | 4 | 5 | 5 | 5 | 1 0 | 3 | 3 |
| I-28 | 25 | 5 | 5 | 5 | 5 | 5 | 5 | 2 1 | 3 | 3 |
| | 6.3 | 5 | 5 | 4 | 5 | 4 | 5 | 1 0 | 3 | 3 |
| I-53 | 25 | 5 | 5 | 5 | 5 | 5 | 5 | 3 1 | 3 | 3 |
| | 6.3 | 5 | 5 | 5 | 5 | 5 | 5 | 1 0 | 3 | 2 |
| I-66 | 25 | 5 | 5 | 5 | 5 | 5 | 5 | 2 1 | 3 | — |
| I-176 | 25 | 5 | 5 | 5 | 5 | 5 | 5 | 3 1 | 3 | 3 |
| | 6.3 | 5 | 5 | 5 | 5 | 5 | 4 | ·2 0 | 3 | 3 |
| I-194 | 25 | 5 | 5 | 4 | 5 | 5 | 5 | 3 0 | 4 | 4 |
| I-204 | 25 | 5 | 5 | 4 | 5 | 5 | 5 | — 1 | 4 | 4 |
| | 6.3 | 4 | 5 | 4 | 5 | 5 | 5 | — 0 | 4 | 3 |
| I-337 | 25 | 5 | 5 | 5 | 5 | 5 | 5 | 4 1 | 4 | 3 |
| | 6.3 | 4 | 5 | 5 | 5 | 5 | 5 | 4 0 | 3 | 3 |
| I-516 | 25 | 4 | 5 | 5 | 5 | 5 | 5 | 2 0 | 4 | 3 |
| II-20 | 25 | 5 | 5 | 5 | 5 | 5 | 5 | 5 0 | 4 | 3 |
| | 6.3 | 5 | 5 | 5 | 5 | 5 | 5 | 0 4 | 3 | |
| II-26 | 25 | 5 | 5 | 5 | 5 | 5 | 5 | 5 0 | 3 | 1 |
| | 6.3 | 5 | 5 | 5 | 5 | 5 | 5 | 5 0 | 2 | 1 |
| II-27 | 25 | 5 | 5 | 5 | 5 | 5 | 5 | 2 0 | 0 | 0 |
| | 6.3 | 5 | 5 | 5 | 5 | 5 | 5 | 1 0 | 0 | 0 |
| II-28 | 25 | 5 | 5 | 5 | 5 | 5 | 5 | — 1 | 3 | 3 |
| | 6.3 | 5 | 5 | 5 | 5 | 5 | 5 | 5 0 | 2 | 2 |
| II-31 | 25 | 5 | 5 | 5 | 5 | 5 | 5 | 5 1 | 1 | 1 |
| | 6.3 | 5 | 5 | 4 | 5 | 5 | 5 | 5 0 | 1 | 1 |
| II-64 | 25 | 5 | 5 | 5 | 5 | 5 | 5 | 4 0 | 0 | 3 |
| | 6.3 | 5 | 5 | 5 | 5 | 5 | 5 | 4 0 | 0 | 2 |
| II-93 | 25 | 5 | 5 | 5 | 5 | 5 | 5 | 5 1 | 1 | 3 |
| | 6.3 | 5 | 5 | 5 | 5 | 5 | 5 | 5 0 | 1 | 3 |
| II-104 | 100 | 5 | 5 | 5 | 5 | 5 | 5 | 5 0 | 0 | 3 |
| | 25 | 5 | 5 | 5 | 5 | 5 | 5 | 4 0 | 0 | 3 |
| II-127 | 25 | 5 | 5 | 4 | 5 | 5 | 5 | 5 0 | 4 | 1 |
| II-134 | 25 | 5 | 5 | 5 | 5 | 5 | 5 | 5 0 | 0 | 0 |
| | 6.3 | 5 | 5 | 4 | 5 | 5 | 5 | 5 0 | 0 | 0 |
| II-150 | 25 | 5 | 5 | 4 | 5 | 5 | 5 | — 0 | 1 | 3 |
| II-157 | 25 | 5 | 5 | 5 | 5 | 5 | 5 | — 0 | 0 | 2 |
| | 6.3 | 5 | 5 | 4 | 5 | 5 | 5 | — 0 | 0 | 1 |
| II-168 | 25 | 5 | 5 | 5 | 5 | 5 | 5 | 4 1 | 4 | 3 |
| | 6.3 | 5 | 5 | 4 | 5 | 5 | 5 | 3 0 | 2 | 3 |
| II-180 | 25 | 5 | 5 | 5 | 5 | 5 | 5 | — 0 | 0 | 1 |
| | 6.3 | 5 | 5 | 4 | 5 | 5 | 5 | — 0 | 0 | 1 |
| II-181 | 25 | 5 | 5 | 5 | 5 | 5 | 5 | 5 1 | 3 | 2 |
| | 6.3 | 5 | 5 | 5 | 5 | 5 | 5 | 4 0 | 1 | 1 |

We claim:

1. An indazolesulfonylurea derivative represented by the general formula:

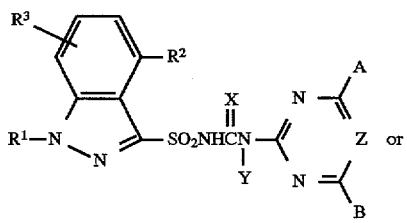

[I]

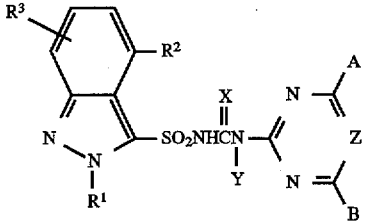

[II]

{wherein $R^1$ is a hydrogen atom, an alkyl group, a cycloalkyl group, a haloalkyl group, an alkoxyalkyl group, a benzyloxyalkyl group, a benzyl group, a phenyl group, a pyridyl group, a dialkylaminocarbonyl group, an alkoxycarbonyl group, an alkylsulfonyl group, a phenylsulfonyl group, a dialkylaminosulfonyl group, a haloalkylcarbonyl group, an alkylcarbonyl group, a benzoyl group or an alkenyl group, $R^2$ and $R^3$ are the same or different and represent a hydrogen atom, a halogen atom, an alkyl group, a cycloalkyl group, an alkenyl group, an alkoxycarbonylalkenyl group, an alkynyl group, a haloalkyl group, an alkoxyalkyl group, an alkoxycarbonylalkyl group, an alkylcarbonylalkyl group, a cycloalkylcarbonylalkyl group, a cyanoalkyl group, a dialkylaminocarbonylalkyl group, a dialkylaminoalkyl group, a dialkylaminosulfonylalkyl group, an azidoalkyl group, a benzyl group, a phenyl group, a nitro group, a cyano group, an azide group, an amino group, a monoalkylamino group, a dialkylamino group, a benzylamino group, an alkylcarbonylamino group which may be substituted by a halogen atom, a benzoylamino group, an alkoxycarbonylamino group, a phenoxycarbonylamino group, an alkylsulfonylamino group wherein the amino group may be substituted by an alkyl group, a phenylsulfonylamino group wherein the amino group may be substituted by an alkyl group, an alkylideneamino group, a benzylideneamino group, a tetrazolyl group which may be substituted, a group represented by the formula —$COR^4$ (wherein $R^4$ is a hydrogen atom, a hydroxyl group, an alkyl group, a cycloalkyl group, a haloalkyl group, an alkenyl group, an alkynyl group, a benzyl group, a phenyl group, an alkoxy group, a haloalkoxy group, an alkoxyalkoxy group, an alkenyloxy group, a haloalkenyloxy group, an alkynyloxy group, a benzyloxy group or a phenoxy group), a group represented by the formula —$C(O)NR^5R^6$ (wherein $R^5$ and $R^6$ are the same or different and represent a hydrogen atom, an alkyl group, an alkenyl group, an alkynyl group, a benzyl group, a phenyl group or an alkoxy group), a group represented by the formula —$SR^7$ (wherein $R^7$ is a hydrogen atom, an alkyl group or a haloalkyl group), a group represented by the formula —$SO_2NR^5R^6$ (wherein $R^5$ and $R^6$ have the same meanings as defined above), a group represented by the formula —$S(O)_nR^8$ (wherein n represents an integer of 1 or 2, and $R^8$ represents an alkyl group, an alkenyl group or a haloalkyl group), a group represented by the formula —$OR^9$ [wherein $R^9$ is a hydrogen atom, an alkyl group, a cycloalkylalkyl group, an alkenyl group, an alkynyl group, a benzyl group (said group may be substituted by a halogen atom, an alkyl group or an alkoxy group), a haloalkyl group, a haloalkenyl group, a phenyl group (said group may be substituted by a halogen atom, an alkyl group or an alkoxy group), an alkoxyalkyl group, an alkoxyalkoxyalkyl group, a haloalkoxyalkyl group, a benzyloxyalkyl group, a phenoxyalkyl group, an alkylthioalkyl group, a dialkylaminoalkyl group, an azidoalkyl group, an alkylcarbonyl group, a haloalkylcarbonyl group, a benzoyl group, a dialkylaminocarbonyl group, a cyanoalkyl group, an alkylideneamino group, a dialkylideneamino group, a benzylideneamino group or an alkoxycarbonylalkyl group], or the formula —C(=NOR$^{10}$)R$^{11}$ (wherein R$^{10}$ represents a hydrogen atom, an alkyl group, an alkenyl group, an alkynyl group, a benzyl group, a haloalkyl group or a phenyl group, and R$^{11}$ represents a hydrogen atom, an alkyl group, a benzyl group, a haloalkyl group or a phenyl group), R$^2$ and R$^3$ may together form a ring with an alkyl group which may contain a hereto atom, A and B are the same or different and represent an alkyl group, a haloalkyl group, an alkoxy group, a monoalkylamino group, a dialkylamino group, a halogen atom or a haloalkoxy group, Z represents a nitrogen atom, X represents an oxygen atom or a sulfur atom, and Y represents a hydrogen atom, an alkyl group or an alkoxyalkyl group.

2. An indazolesulfonylurea derivative represented by the general formula:

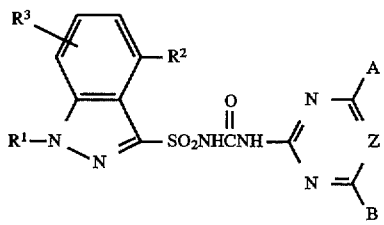

[I]

(wherein R$^1$ is a hydrogen atom, an alkyl group or an alkenyl group, R$^2$ and R$^3$ are the same or different and represent a hydrogen atom, a halogen atom, an alkyl group, an alkoxy group, a haloalkoxy group, an alkylthio group, an alkylsulfinyl group, an alkylsulfonyl group, an alkoxycarbonyl group, a dialkylaminocarbonyl group, a nitro group or a cyano group, A and B are the same or different and represent an alkyl group, an alkoxy group or a halogen atom, and Z is a nitrogen atom).

3. An indazolesulfonylurea derivative represented by the general formula:

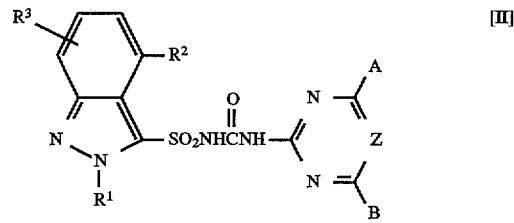

[II]

(wherein R$^1$ is a hydrogen atom, an alkyl group or a phenyl group, R$^2$ and R$^3$ are the same or different and represent a hydrogen atom, a halogen atom, an alkyl group, a hydroxyl group, an alkoxy group, a haloalkenyloxy group, an alkoxycarbonylalkoxy group, a cycloalkylalkoxy group, a dialkylaminoalkoxy group, a alkoxyalkoxy group, a haloalkoxy group, an alkynyloxy group, an alkenyloxy group, an alkylthio group, an alkylsulfonyl group, an alkoxycarbonyl group, a dialkylaminocarbonyl group, a nitro group, a cyano group, a monoalkylamino group, a dialkylamino group or a benzylamino group, A and Z are the same or different and represent an alkyl group, an alkoxy group or a halogen atom, and B represents a nitrogen atom).

4. A herbicidal composition comprising:

an indazolesulfonylurea as defined in claim 1 and an inert carrier.

* * * * *